US011284833B2

(12) United States Patent
Mhajna

(10) Patent No.: US 11,284,833 B2
(45) Date of Patent: Mar. 29, 2022

(54) SYSTEMS AND METHODS FOR MATERNAL UTERINE ACTIVITY DETECTION

(71) Applicant: NUVO GROUP LTD., Tel Aviv (IL)

(72) Inventor: Muhammad Mhajna, Tel Aviv (IL)

(73) Assignee: Nuvo Group Ltd., Tel Aviv (IL)

( * ) Notice: Subject to any disclaimer, the term of this patent is extended or adjusted under 35 U.S.C. 154(b) by 0 days.

(21) Appl. No.: 17/168,771

(22) Filed: Feb. 5, 2021

(65) Prior Publication Data
US 2021/0236046 A1 Aug. 5, 2021

Related U.S. Application Data

(60) Provisional application No. 62/970,447, filed on Feb. 5, 2020.

(51) Int. Cl.
| | | |
|---|---|---|
| *A61B 5/00* | (2006.01) | |
| *A61B 5/352* | (2021.01) | |
| *A61B 5/316* | (2021.01) | |
| *A61B 5/256* | (2021.01) | |
| *A61B 5/344* | (2021.01) | |
| *A61B 5/279* | (2021.01) | |

(52) U.S. Cl.
CPC ............ *A61B 5/4356* (2013.01); *A61B 5/352* (2021.01); *A61B 5/7207* (2013.01); *A61B 5/7225* (2013.01); *A61B 5/7282* (2013.01); *A61B 5/256* (2021.01); *A61B 5/279* (2021.01); *A61B 5/316* (2021.01); *A61B 5/344* (2021.01); *A61B 2562/0204* (2013.01)

(58) Field of Classification Search
CPC ...................................................... A61B 5/033
See application file for complete search history.

(56) References Cited

U.S. PATENT DOCUMENTS

2012/0071744 A1* 3/2012 Euliano, II ............. A61B 5/033
600/382

* cited by examiner

*Primary Examiner* — Jacqueline Cheng
*Assistant Examiner* — Tho Q Tran
(74) *Attorney, Agent, or Firm* — Greenberg Traurig, LLP

(57) ABSTRACT

A method includes receiving acoustic inputs; generating signal channels from the acoustic inputs; pre-processing data in the signal channels; extracting S1-S2 peaks from the pre-processed data; removing artifacts and outliers from the S1-S2 peaks; generating S1-S2 signal channels based on the S1-S2 peaks in the pre-processed signal channels; selecting two or more of the S1-S2 signal channels; and combining the selected two or more S1-S2 signal channels to produce an acoustic uterine monitoring signal.

17 Claims, 43 Drawing Sheets

Signal after resampling

SYSTEMS AND METHODS FOR MATERNAL UTERINE ACTIVITY DETECTION

CROSS-REFERENCE TO RELATED APPLICATION

This application is a Section 111(a) application relating to and claiming the benefit of commonly-owned, U.S. Provisional Patent Application No. 62/970,447, filed on Feb. 5, 2020 and entitled "SYSTEMS AND METHODS FOR MATERNAL UTERINE ACTIVITY DETECTION," the contents of which are incorporated herein by reference in their entirety.

FIELD OF THE INVENTION

The invention relates generally to monitoring of expectant mothers. More particularly, the invention relates to analysis of sensed acoustic data to produce computed representations of uterine activity, such as uterine contractions.

BACKGROUND

A uterine contraction is a temporary process during which the muscles of the uterus are shortened and the space between muscle cells decreases. These structural changes in the muscle cause an increase in uterine cavity pressure to allow pushing the fetus downward in a lower position towards delivery. During a uterine contraction, the structure of myometrial cells (i.e., cells of the uterus) changes and the uterine wall becomes thicker. FIG. 1A shows an illustration of a relaxed uterus, in which the muscular wall of the uterus is relaxed. FIG. 1B shows an illustration of a contracted uterus, in which the muscular wall of the uterus contracts and pushes the fetus against the cervix.

Uterine contractions are monitored to evaluate the progress of labor. Typically, the progress of labor is monitored through the use of two sensors: a tocodynamometer, which is a strain gauge-based sensor positioned on the abdomen of an expectant mother, and an ultrasound transducer, which is also positioned on the abdomen. The signals of the tocodynamometer are used to provide a tocograph ("TOCO"), which is analyzed to identify uterine contractions, while the signals of the ultrasound transducer are used to detect fetal heart rate, maternal heart rate, and fetal movement. However, these sensors can be uncomfortable to wear, and can produce unreliable data when worn by obese expectant mothers.

SUMMARY

In some embodiments, the present invention provides a specifically programmed computer system, including at least the following components: a non-transient memory, electronically storing computer-executable program code; and at least one computer processor that, when executing the program code, becomes a specifically programmed computing processor that is configured to perform at least the following operations: receiving a plurality of bio-potential signals collected at a plurality of locations on the abdomen of a pregnant mother; detecting R-wave peaks in the bio-potential signals; extracting maternal electrocardiogram ("ECG") signals from the bio-potential signals; determining R-wave amplitudes in the maternal ECG signals; creating an R-wave amplitude signal for each of the maternal ECG signals; calculating an average of all the R-wave amplitude signals; and normalizing the average to produce an electrical uterine monitoring ("EUM") signal. In some embodiments, the operations also include identifying at least one uterine contraction based on a corresponding at least one peak in the EUM signal.

In some embodiments, the present invention provides a method including receiving a plurality of bio-potential signals collected at a plurality of locations on the abdomen of a pregnant mother; detecting R-wave peaks in the bio-potential signals; extracting maternal ECG signals from the bio-potential signals; determining R-wave amplitudes in the maternal ECG signals; creating an R-wave amplitude signal for each of the maternal ECG signals; calculating an average of all the R-wave amplitude signals; and normalizing the average to produce an EUM signal. In some embodiments, the method also includes identifying at least one uterine contraction based on a corresponding at least one peak in the EUM signal.

In an embodiment, a computer-implemented method receiving, by at least one computer processor, a plurality of raw bio-potential inputs, wherein each of the raw bio-potential inputs being received from a corresponding one of a plurality of electrodes, wherein each of the plurality of electrodes is positioned so as to measure a respective one of the raw bio-potential inputs of a pregnant human subject; generating, by the at least one computer processor, a plurality of signal channels from the plurality of raw-bio-potential inputs, wherein the plurality of signal channels includes at least three signal channels; pre-processing, by the at least one computer processor, respective signal channel data of each of the signal channels to produce a plurality of pre-processed signal channels, wherein each of the pre-processed signal channels includes respective pre-processed signal channel data; extracting, by the at least one computer processor, a respective plurality of R-wave peaks from the pre-processed signal channel data of each of the pre-processed signal channels to produce a plurality of R-wave peak data sets, wherein each of the R-wave peak data sets includes a respective plurality of R-wave peaks; removing, by the at least one computer processor, from the plurality of R-wave peak data sets, at least one of: (a) at least one signal artifact or (b) at least one outlier data point, wherein the at least one signal artifact is one of an electromyography artifact or a baseline artifact; replacing, by the at least one computer processor, the at least one signal artifact, the at least one outlier data point, or both, with at least one statistical value determined based on a corresponding one of the R-wave peak data sets from which the at least one signal artifact, the at least one outlier data point, or both was removed; generating, by the at least one computer processor, a respective R-wave signal data set for a respective R-wave signal channel at a predetermined sampling rate based on each respective R-wave peak data set to produce a plurality of R-wave signal channels; selecting, by the at least one computer processor, at least one first selected R-wave signal channel and at least one second selected R-wave signal channel from the plurality of R-wave channels based on at least one correlation between (a) the respective R-wave signal data set of at least one first particular R-wave signal channel and (b) the respective R-wave signal data set of at least one second particular R-wave signal channel; generating, by the at least one computer processor, electrical uterine monitoring data representative of an electrical uterine monitoring signal based on at least the respective R-wave signal data set of the first selected R-wave signal channel and the respective R-wave signal data set of the second selected R-wave signal channel.

In an embodiment, a computer-implemented method also includes sharpening, by the at least one computer processor, the electrical uterine monitoring data to produce a sharpened electrical uterine monitoring signal. In an embodiment, the sharpening step is omitted if the electrical uterine monitoring data is calculated based on a selected one of the electrical uterine monitoring signal channels that is a corrupted electrical uterine signal monitoring channel. In an embodiment, a computer-implemented method also includes post-processing the sharpened electrical monitoring signal data to produce a post-processed electrical uterine monitoring signal. In an embodiment, the sharpening step includes identifying a set of peaks in the electrical uterine monitoring signal data; determining a prominence of each of the peaks; removing, from the set of peaks, peaks having a prominence that is less than at least one threshold prominence value; calculating a mask based on remaining peaks of the set of peaks; smoothing the mask based on a moving average window to produce a smoothed mask; and adding the smoothed mask to the electrical uterine monitoring signal data to produce the sharpened electrical uterine monitoring signal data. In an embodiment, the at least one threshold prominence value includes at least one threshold prominence value selected from the group consisting of an absolute prominence value and a relative prominence value calculated based on a maximal prominence of the peaks in the set of peaks. In an embodiment, the mask includes zero values outside areas of the remaining peaks and nonzero values inside areas of the remaining peaks, wherein the nonzero values are calculated based on a Gaussian function In an embodiment, the at least one filtering step of the pre-processing step includes applying at least one filter selected from the group consisting of a DC removal filter, a powerline filter, and a high pass filter.

In an embodiment, the extracting step includes receiving a set of maternal ECG peaks for the pregnant human subject; and identifying R-wave peaks in each of the pre-processed signal channels within a predetermined time window before and after each of the maternal ECG peaks in the set of maternal ECG peaks as the maximum absolute value in each of the pre-processed signal channels within the predetermined time window.

In an embodiment, the step of removing at least one of a signal artifact or an outlier data point includes removing at least one electromyography artifact by a process including identifying at least one corrupted peak in one of the plurality of R-wave peaks data sets based on the at least one corrupted peak having an inter-peaks root mean square value that is greater than a threshold; and replacing the corrupted peak with a median value, wherein the median value is either a local median or a global median.

In an embodiment, the step of removing at least one of a signal artifact or an outlier data point includes removing at least one baseline artifact by a process including: identifying a change point in R-wave peaks in one of the plurality of R-wave peaks data sets; subdividing the one of the plurality of R-wave peaks data sets into a first portion located prior to the change point and a second portion located subsequent to the change point; determining a first root-mean-square value for the first portion; determining a second root-mean-square value for the second portion; determining an equalization factor based on the first root-mean-square value and the second root-mean-square value; and modifying the first portion by multiplying R-wave peaks in the first portion by the equalization factor.

In an embodiment, the step of removing at least one of a signal artifact or an outlier point includes removing at least one outlier in accordance with a Grubbs test for outliers.

In an embodiment, the step of generating a respective R-wave data set based on each respective R-wave peak data set includes interpolating between the R-wave peaks of each respective R-wave peak data set, and wherein the interpolating between the R-wave peaks includes interpolating using an interpolation algorithm that is selected from the group consisting of a cubic spline interpolation algorithm and a shape-preserving piecewise cubic interpolation algorithm.

In an embodiment, the step of selecting at least one first one of the R-wave signal channels and at least one second one of the R-wave signal channels includes selecting candidate R-wave signal channels from the R-wave signal channels based on a percentage of prior intervals in which each of the R-wave signal channels experienced contact issues; grouping the selected candidate R-wave signal channels into a plurality of couples, wherein each of the couples includes two of the selected candidate R-wave channels that are independent from one another; calculating a correlation value of each of the couples; and selecting, as the selected at least one first one of the R-wave signal channels and the selected at least one second one of the R-wave signal channels, the candidate R-wave signal channels of at least one of the couples based on the at least one of the couples having a correlation value that exceeds a threshold correlation value.

In an embodiment, the step of calculating the electrical uterine monitoring signal includes calculating a signal that is a predetermined percentile of the selected at least one first one of the R-wave signal channels and the selected at least one second one of the R-wave signal channels. In an embodiment, the predetermined percentile is an $80^{th}$ percentile.

In an embodiment, the statistical value is one of a local median, a global median, or a mean.

In some embodiments, computer-implemented method includes receiving, by at least one computer processor, a plurality of raw acoustic inputs, wherein each of the raw acoustic inputs being received from a corresponding one of a plurality of acoustic sensors, and wherein each of the plurality of acoustic sensors is positioned so as to measure a respective one of the raw acoustic inputs of a pregnant human subject; generating, by the at least one computer processor, a plurality of signal channels from the plurality of raw acoustic inputs, wherein the plurality of signal channels includes at least three signal channels; pre-processing, by the at least one computer processor, respective signal channel data of each of the signal channels to produce a plurality of pre-processed signal channels, wherein each of the pre-processed signal channels includes respective pre-processed signal channel data; extracting, by the at least one computer processor, a respective plurality of S1-S2 peaks from the pre-processed signal channel data of each of the pre-processed signal channels to produce a plurality of S1-S2 peak data sets, wherein each of the S1-S2 peak data sets includes a respective plurality of S1-S2 peaks; removing, by the at least one computer processor, from the plurality of S1-S2 peak data sets, at least one of: (a) at least one signal artifact or (b) at least one outlier data point, wherein the at least one signal artifact is one of a movement-related artifact or a baseline artifact; replacing, by the at least one computer processor, the at least one signal artifact, the at least one outlier data point, or both, with at least one statistical value determined based on a corresponding one of the S1-S2 peak data sets from which the at least one signal artifact, the at least one outlier data point, or both was removed, to produce a plurality of interpolated S1-S2 peak data sets; generating, by the at least one computer processor, a respective S1-S2 signal data set for a respective S1-S2 signal channel at a predetermined sampling rate based on each respective interpolated S1-S2 peak data set to produce a plurality of S1-S2 signal channels; selecting, by the at least one computer processor, at least one first selected S1-S2 signal channel and at least one second selected S1-S2 signal channel from the plurality of S1-S2 signal channels based on at least one correlation between (a) a respective S1-S2 signal data set of at least one first particular S1-S2 signal channel and (b) a respective S1-S2 signal data set of at least one second particular S1-S2 signal channel; and generating, by the at least one computer processor, acoustic uterine monitoring data representative of an acoustic uterine monitoring signal based on at least the respective S1-S2 signal data set of the first selected S1-S2 signal channel and the respective S1-S2 signal data set of the second selected S1-S2 signal channel.

In some embodiments, the computer-implemented method also includes sharpening, by the at least one computer processor, the acoustic uterine monitoring data to produce a sharpened acoustic uterine monitoring signal. In some embodiments, the computer-implemented method also includes determining, by the at least one computer processor, whether the acoustic uterine monitoring data is calculated based on based on a selected one of the acoustic uterine monitoring signal channels that is a corrupted acoustic uterine monitoring signal channel, wherein the step of sharpening, by the at least one computer processor, the acoustic uterine monitoring data is omitted if the acoustic uterine monitoring data is calculated based on the selected one of the acoustic uterine monitoring signal channels that is the corrupted acoustic uterine signal monitoring channel. In some embodiments, the computer-implemented method also includes post-processing the sharpened acoustic monitoring signal data to produce a post-processed acoustic uterine monitoring signal. In some embodiments, the step of sharpening, by the at least one computer processor, the acoustic uterine monitoring data includes: identifying a set of peaks in the acoustic uterine monitoring signal data; determining a prominence of each of the peaks; removing, from the set of peaks, peaks having a prominence that is less than at least one threshold prominence value; calculating a mask based on remaining peaks of the set of peaks; smoothing the mask based on a moving average window to produce a smoothed mask; and adding the smoothed mask to the acoustic uterine monitoring signal data to produce the sharpened acoustic uterine monitoring signal data. In some embodiments, the at least one threshold prominence value includes at least one threshold prominence value selected from a group consisting of an absolute prominence value and a relative prominence value calculated based on a maximal prominence of the peaks in the set of peaks. In some embodiments, the mask includes zero values outside areas of the remaining peaks and nonzero values inside areas of the remaining peaks, wherein the nonzero values are calculated based on a Gaussian function.

In some embodiments, the at least one filtering step of the pre-processing step includes applying at least one filter selected from a group consisting of a DC removal filter, a powerline filter, and a high pass filter.

In some embodiments, the step of extracting, by the at least one computer processor, the respective plurality of S1-S2 peaks includes: receiving a set of maternal ECG peaks for the pregnant human subject; and identifying S1-S2 peaks in each of the pre-processed signal channels within a predetermined time window before and after each of the maternal ECG peaks in the set of maternal ECG peaks as a maximum absolute value in each of the pre-processed signal channels within the predetermined time window.

In some embodiments, the step of removing at least one of a signal artifact or an outlier data point includes removing at least one movement artifact by a process including: identifying at least one corrupted peak in one of the plurality of S1-S2 peak data sets based on the at least one corrupted peak having an inter-peaks root mean square value that is greater than a threshold; and replacing the corrupted peak with a median value, wherein the median value is either a local median or a global median.

In some embodiments, the step of removing at least one of a signal artifact or an outlier data point includes removing at least one baseline artifact by a process including: identifying a change point in S1-S2 peaks in one of the plurality of S1-S2 peak data sets; subdividing the one of the plurality of S1-S2 peak data sets into a first portion located prior to the change point and a second portion located subsequent to the change point; determining a first root-mean-square value for the first portion; determining a second root-mean-square value for the second portion; determining an equalization factor based on the first root-mean-square value and the second root-mean-square value; and modifying the first portion by multiplying S1-S2 peaks in the first portion by the equalization factor.

In some embodiments, the step of removing at least one of a signal artifact or an outlier point includes removing at least one outlier in accordance with a Grubbs test for outliers.

In some embodiments, the step of generating a respective S1-S2 data set based on each respective S1-S2 peak data set includes interpolating between the S1-S2 peaks of each respective S1-S2 peak data set, and the interpolating between the S1-S2 peaks includes interpolating using an interpolation algorithm that is selected from a group consisting of a cubic spline interpolation algorithm and a shape-preserving piecewise cubic interpolation algorithm.

In some embodiments, the step of selecting at least one first one of the S1-S2 signal channels and at least one second one of the S1-S2 signal channels from the plurality of S1-S2 signal channels includes: identifying contact issues in each of the plurality of S1-S2 signal channels; determining a percentage of prior intervals in which each of the plurality of S1-S2 signal channels experienced contact issues; selecting candidate S1-S2 signal channels from the plurality of S1-S2 signal channels based on the percentage of prior intervals in which each of the plurality of S1-S2 signal channels experienced contact issues; grouping the selected candidate S1-S2 signal channels into a plurality of couples, wherein each of the couples includes two of the selected candidate S1-S2 channels that are independent from one another; calculating a correlation value of each of the couples; identifying at least one of the couples having a correlation value that exceeds a threshold correlation value; selecting, as the selected at least one first one of the S1-S2 signal channels, the first candidate S1-S2 signal channel of each of the identified at least one of the couples; and selecting, as the selected at least one second one of the S1-S2 signal channels, the second candidate S1-S2 signal channel of each of the identified at least one of the couples.

In some embodiments, the step of calculating the acoustic uterine monitoring signal includes calculating the acoustic uterine monitoring signal that is, at each point in time, a predetermined percentile of all of the selected at least one first one of the S1-S2 signal channels and the selected at least one second one of the S1-S2 signal channels at that point in time. In some embodiments, the predetermined percentile is an 80th percentile.

In some embodiments, the statistical value is one of a local median, a global median, or a mean.

DETAILED DESCRIPTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on." Ranges discussed herein are inclusive (e.g., a range of "between 0 and 2" includes the values 0 and 2 as well as all values therebetween).

As used herein the term "contact region" encompasses the contact area between the skin of a pregnant human subject and cutaneous contact i.e. the surface area through which current flow can pass between the skin of the pregnant human subject and the cutaneous contact.

In some embodiments, the present invention provides a method for extracting a tocograph-like signal from bio-potential data, that is, data describing electrical potential recorded at points on a person's skin through the use of cutaneous contacts, commonly called electrodes. In some embodiments, the present invention provides a method for detecting uterine contractions from bio-potential data. In some embodiments, bio-potential data is obtained through the use of non-contact electrodes positioned against or in the vicinity of desired points on a person's body.

In some embodiments, the present invention provides a system for detecting, recording and analyzing cardiac electrical activity data from a pregnant human subject. In some embodiments, a plurality of electrodes configured to detect fetal electrocardiogram signals is used to record the cardiac activity data. In some embodiments, a plurality of electrodes configured to detect fetal electrocardiogram signals and a plurality of acoustic sensors are used to record the cardiac activity data.

Figure 3:
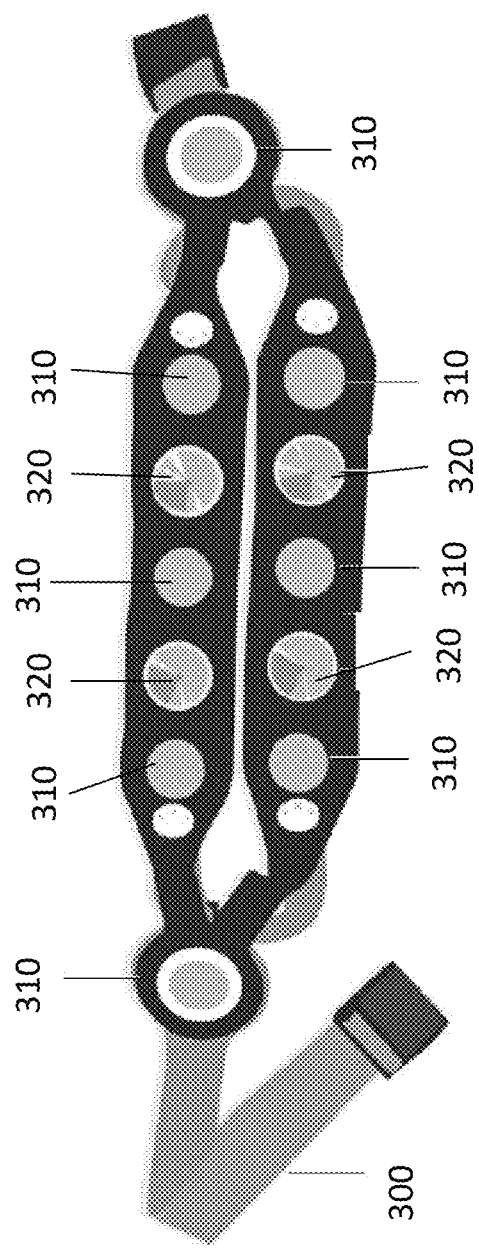
FIG. 3 shows an exemplary garment including a plurality of bio-potential sensors, which may be used to sense data that is to be analyzed in accordance with the exemplary method of FIG. 2.
Figure 4B:
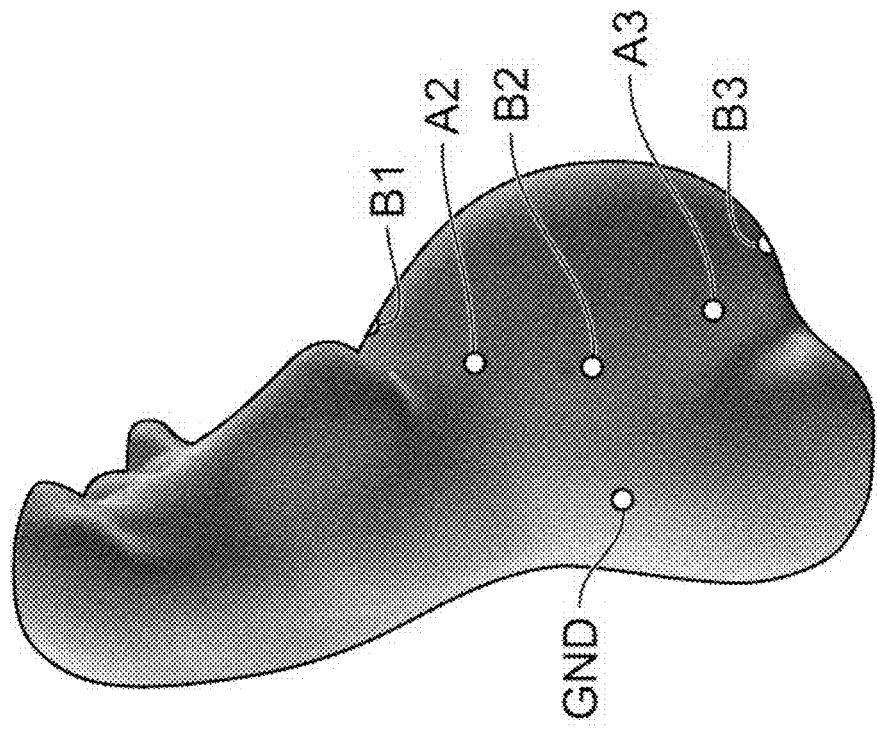
FIG. 4B shows a side view of the positions of the ECG sensor pairs on the abdomen of a pregnant woman according to some embodiments of the present invention.
Figure 4A:
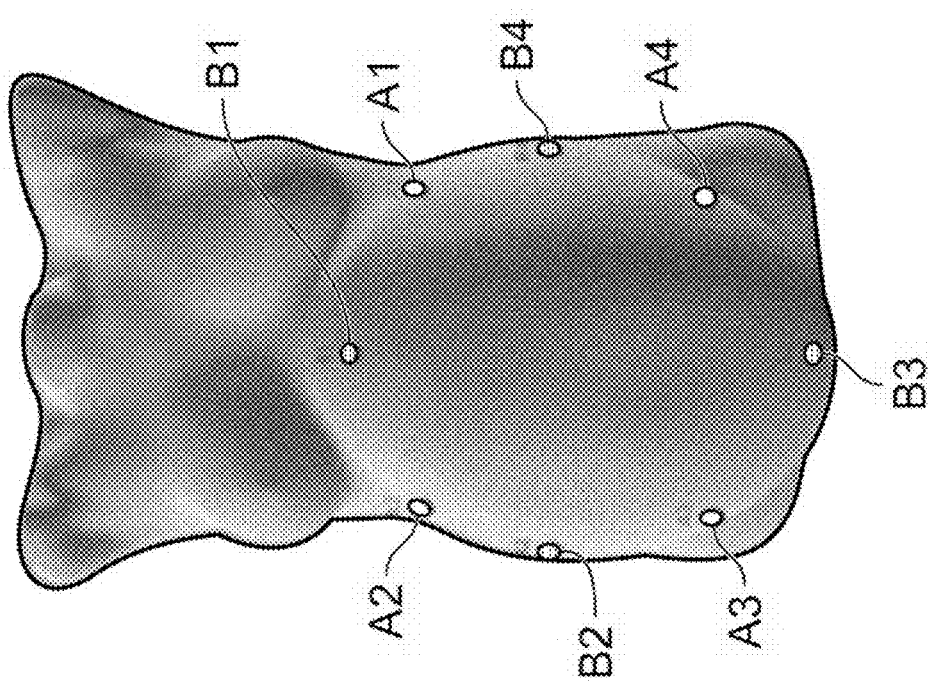
FIG. 4A shows a front view of the positions of ECG sensor pairs on the abdomen of a pregnant woman according to some embodiments of the present invention.

In some embodiments, a plurality of electrodes configured to detect fetal electrocardiogram signals are attached to the abdomen of the pregnant human subject. In some embodiments, the plurality of electrodes configured to detect fetal electrocardiogram signals are directly attached to the abdomen. In some embodiments, the plurality of electrodes configured to detect fetal electrocardiogram signals are incorporated into an article, such as, for example, a belt, a patch, and the like, and the article is worn by, or placed on, the pregnant human subject. FIG. 3 shows an exemplary garment 300, which includes eight electrodes 310 incorporated into the garment 300 so as to be positioned around the abdomen of a pregnant human subject when the garment 300 is worn by the subject. In some embodiments, the garment 300 includes four acoustic sensors 320 incorporated into the garment 300 so as to be positioned around the abdomen of a pregnant human subject when the garment 300 is worn by the subject. In some embodiments, each of the acoustic sensors 320 is one of the acoustic sensors described in U.S. Pat. No. 9,713,430. FIG. 4A shows a front view of the positions of the eight electrodes 310 on the abdomen of a pregnant woman according to some embodiments of the present invention. FIG. 4B shows a side view of the eight electrodes 310 on the abdomen of a pregnant woman according to some embodiments of the present invention.

Figure 1B:
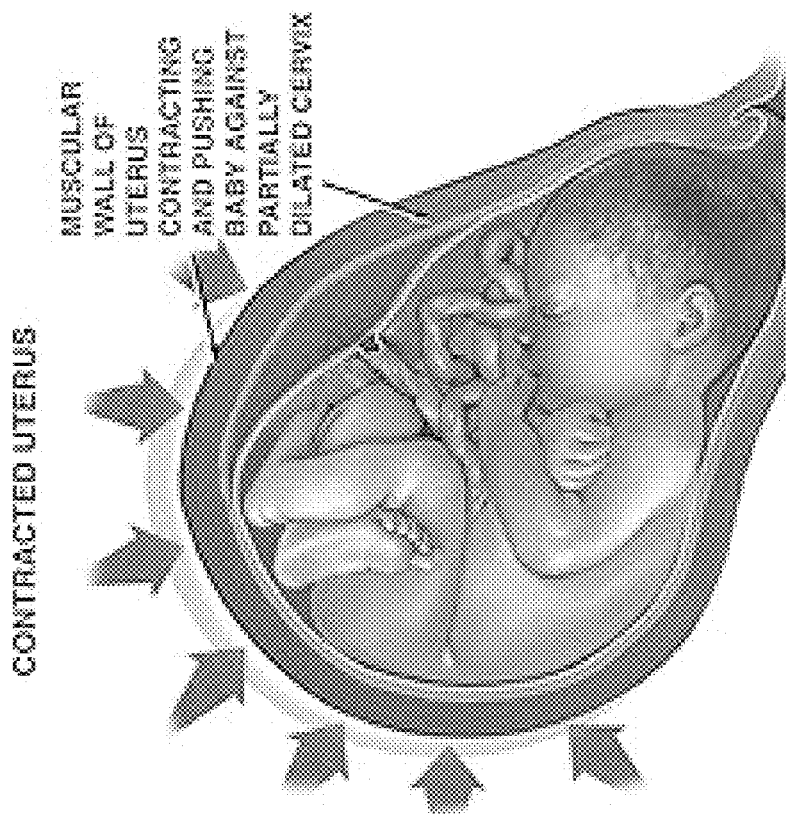
FIG. 1B shows a representative uterus in a contracted state.
Figure 1A:
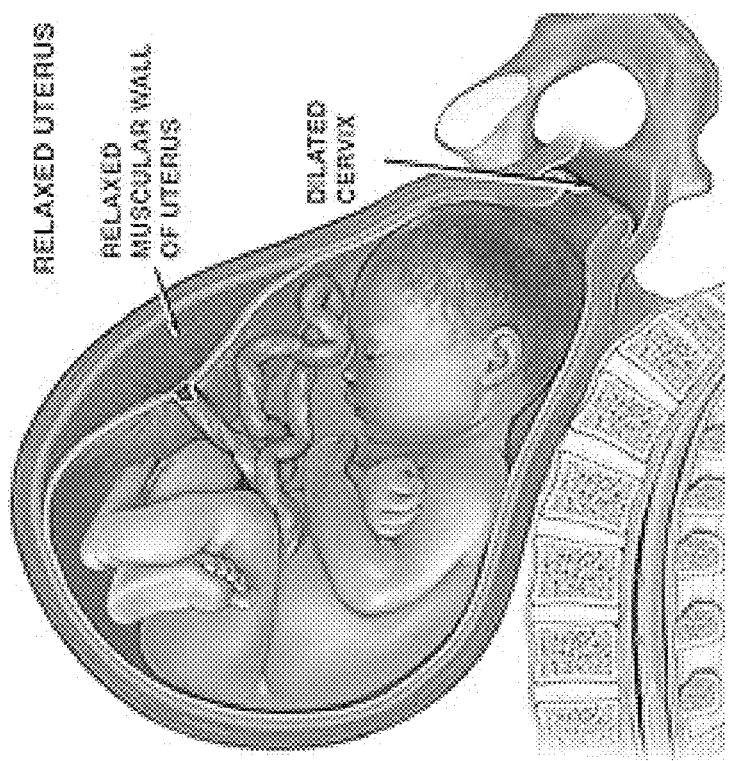
FIG. 1A shows a representative uterus in a non-contracted state.
Figure 2:
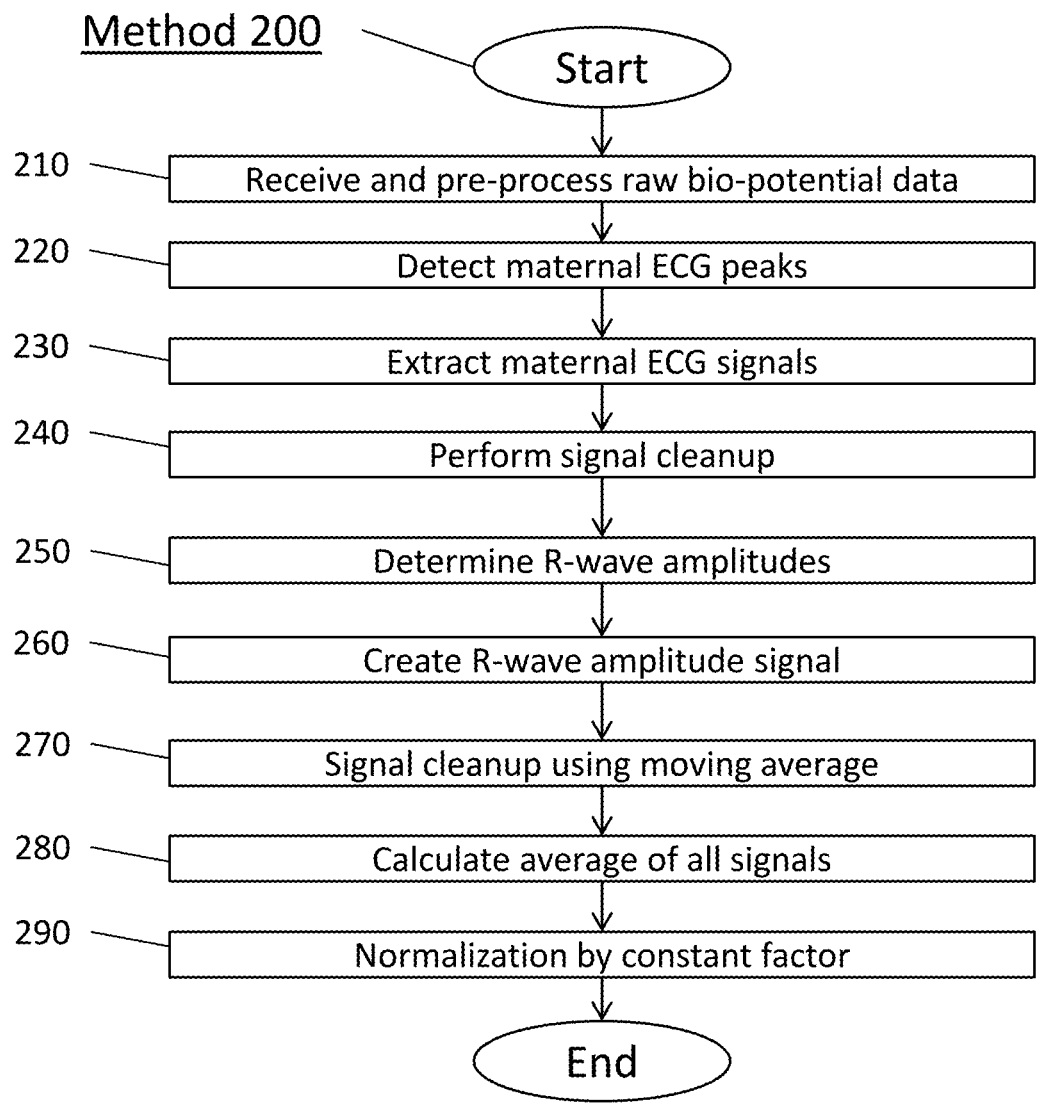
FIG. 2 shows a flowchart of an exemplary method.

FIG. 2 shows a flowchart of an exemplary inventive method 200. In some embodiments, an exemplary inventive computing device, programmed/configured in accordance with the method 200, is operative to receive, as input, raw bio-potential data measured by a plurality of electrodes positioned on the skin of a pregnant human subject, and analyze such input to produce a tocograph-like signal. In some embodiments, the quantity of electrodes is between 2 and 10. In some embodiments, the quantity of electrodes is between 2 and 20. In some embodiments, the quantity of electrodes is between 2 and 30. In some embodiments, the quantity of electrodes is between 2 and 40. In some embodiments, the quantity of electrodes is between 4 and 10. In some embodiments, the quantity of electrodes is between 4 and 20. In some embodiments, the quantity of electrodes is between 4 and 30. In some embodiments, the quantity of electrodes is between 4 and 40. In some embodiments, the quantity of electrodes is between 6 and 10. In some embodiments, the quantity of electrodes is between 6 and 20. In some embodiments, the quantity of electrodes is between 6 and 30. In some embodiments, the quantity of electrodes is between 6 and 40. In some embodiments, the quantity of electrodes is between 8 and 10. In some embodiments, the quantity of electrodes is between 8 and 20. In some embodiments, the quantity of electrodes is between 8 and 30. In some embodiments, the quantity of electrodes is between 8 and 40. In some embodiments, the quantity of electrodes is 8. In some embodiments, the exemplary inventive computing device, programmed/configured in accordance with the method 200, is operative to receive, as input, maternal ECG signals that have already been extracted from raw bio-potential data (e.g., by separation from fetal ECG signals that form part of the same raw bio-potential data). In some embodiments, the exemplary inventive computing device is programmed/configured in accordance with the method 200 via instructions stored in a non-transitory computer-readable medium. In some embodiments, the exemplary inventive computing device includes at least one computer processor, which, when executing the instructions, becomes a specifically-programmed computer processor programmed/configured in accordance with the method 200.

In some embodiments, the exemplary inventive computing device is programmed/configured to continuously perform one or more steps of the method 200 along a moving time window. In some embodiments, the moving time window has a predefined length. In some embodiments, the predefined length is sixty seconds. In some embodiments, the exemplary inventive computing device is programmed/configured to continuously perform one or more steps of the method 200 along a moving time window having a length that is between one second and one hour. In some embodiments, the length of the moving time window is between thirty seconds and 30 minutes. In some embodiments, the length of the moving time window is between 30 seconds and 10 minutes. In some embodiments, the length of the moving time window is between 30 seconds and 5 minutes. In some embodiments, the length of the moving time window is about 60 seconds. In some embodiments, the length of the moving time window is 60 seconds.

Figure 5:
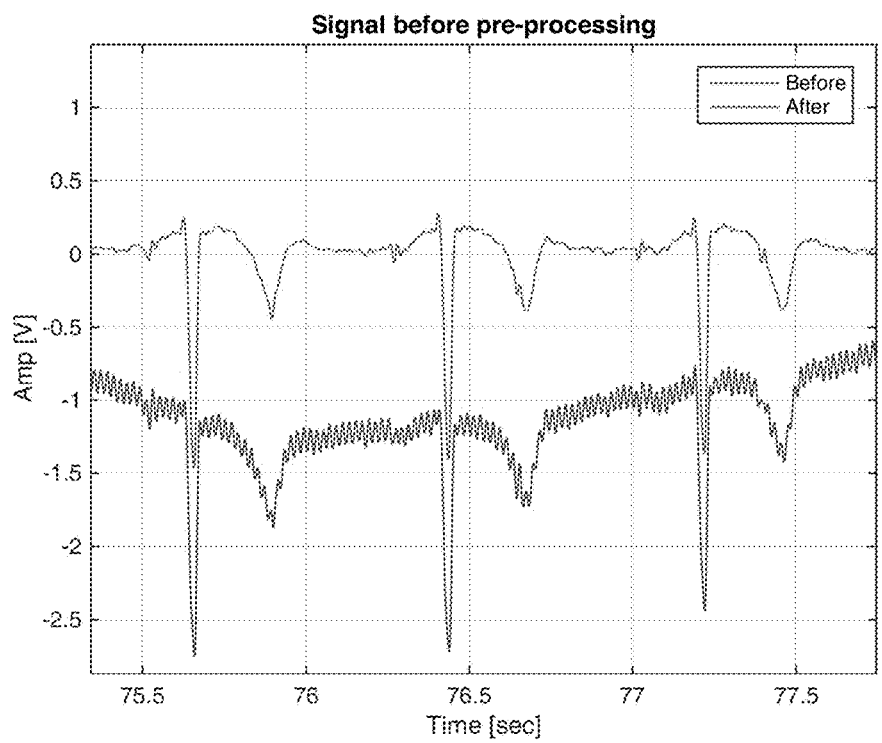
FIG. 5 shows an exemplary bio-potential signal before and after pre-processing.

In step 210, the exemplary inventive computing device is programmed/configured to receive raw bio-potential data as input and pre-process it. In some embodiments, the raw bio-potential data is recorded through the use of at least two electrodes positioned in proximity to a pregnant subject's skin. In some embodiments, at least one of the electrodes is a signal electrode. In some embodiments at least one of the electrodes is a reference electrode. In some embodiments, the reference electrode is located at a point away from the uterus of the subject. In some embodiments, a bio-potential signal is recorded at each of several points around the pregnant subject's abdomen. In some embodiments, a bio-potential signal is recorded at each of eight points around the pregnant subject's abdomen. In some embodiments, the bio-potential data is recorded at 1,000 samples per second. In some embodiments, the bio-potential data is up-sampled to 1,000 samples per second. In some embodiments, the bio-potential data is recorded at a sampling rate of between 100 and 10,000 samples per second. In some embodiments, the bio-potential data is up-sampled to a sampling rate of between 100 and 10,000 samples per second. In some embodiments, the pre-processing includes baseline removal (e.g., using a median filter and/or a moving average filter). In some embodiments, the pre-processing includes low-pass filtering. In some embodiments, the pre-processing includes low-pass filtering at 85 Hz. In some embodiments, the pre-processing includes power line interference cancellation. FIG. 5 shows a portion of a raw bio-potential data signal both before and after pre-processing.

Figure 6A:
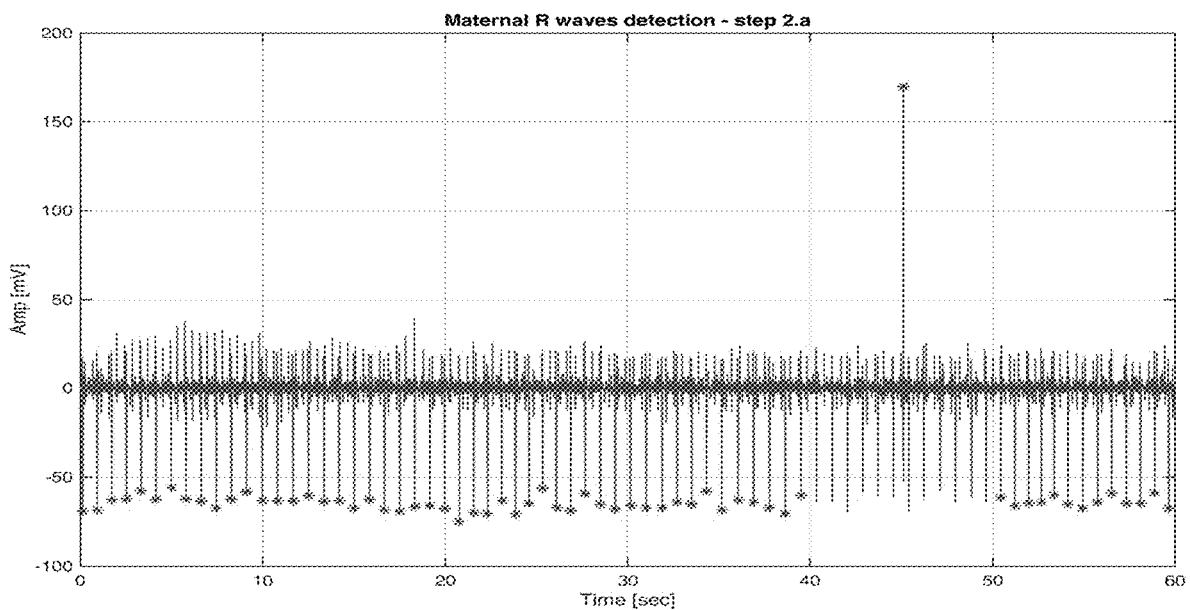
FIG. 6A shows an exemplary bio-potential signal after pre-processing and with detected R-wave peaks indicated.

In step 220, the exemplary inventive computing device is programmed/configured to detect maternal R-wave peaks in the pre-processed bio-potential data resulting from the performance of step 210. In some embodiments, R-wave peaks are detected over 10-second segments of each data signal. In some embodiments, the detection of R-wave peaks begins by analysis of derivatives, thresholding, and distances. In some embodiments, the detection of R-wave peaks in each data signal includes calculating the first derivative of the data signal in the 10-second segment, identifying an R-wave peak in the 10-second segment by identifying a zero-crossing of the first derivative, and excluding identified peaks having either (a) an absolute value that is less than a predetermined R-wave peak threshold absolute value or (b) a distance between adjacent identified R-wave peaks that is less than a predetermined R-wave peak threshold distance. In some embodiments, the detection of R-wave peaks is performed in a manner similar to the detection of electrocardiogram peaks described in U.S. Pat. No. 9,392,952, the contents of which are incorporated herein by reference in their entirety. FIG. 6A shows a pre-processed bio-potential data signal, with R-wave peaks detected as described above indicated with asterisks.

Figure 6B:
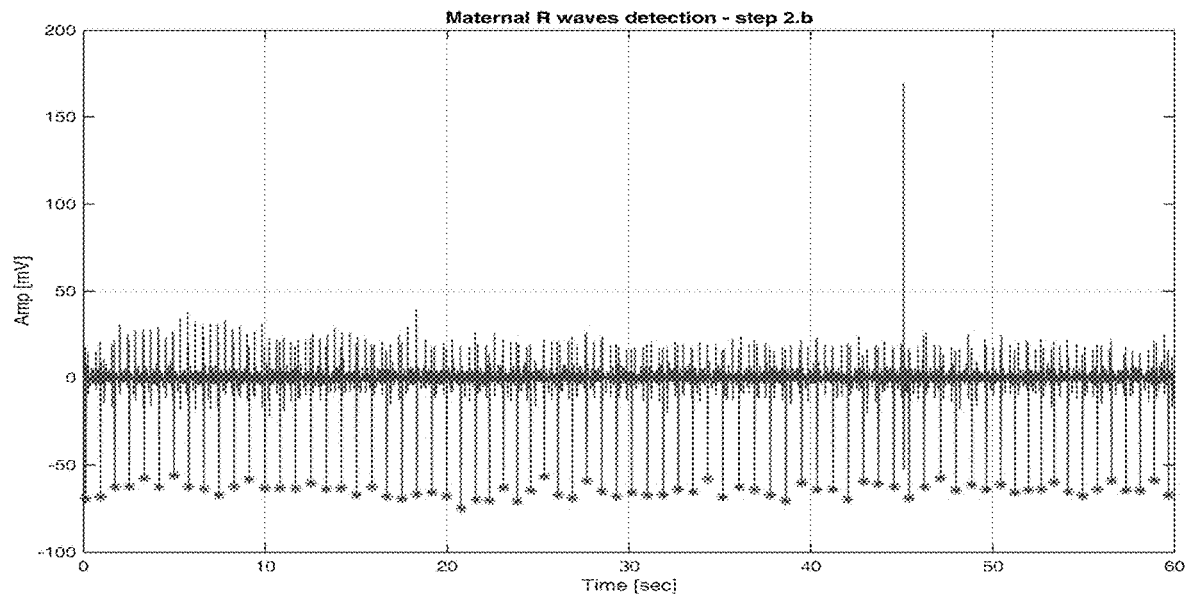
FIG. 6B shows the exemplary bio-potential signal of FIG. 6A after peak re-detection.
Figure 6C:
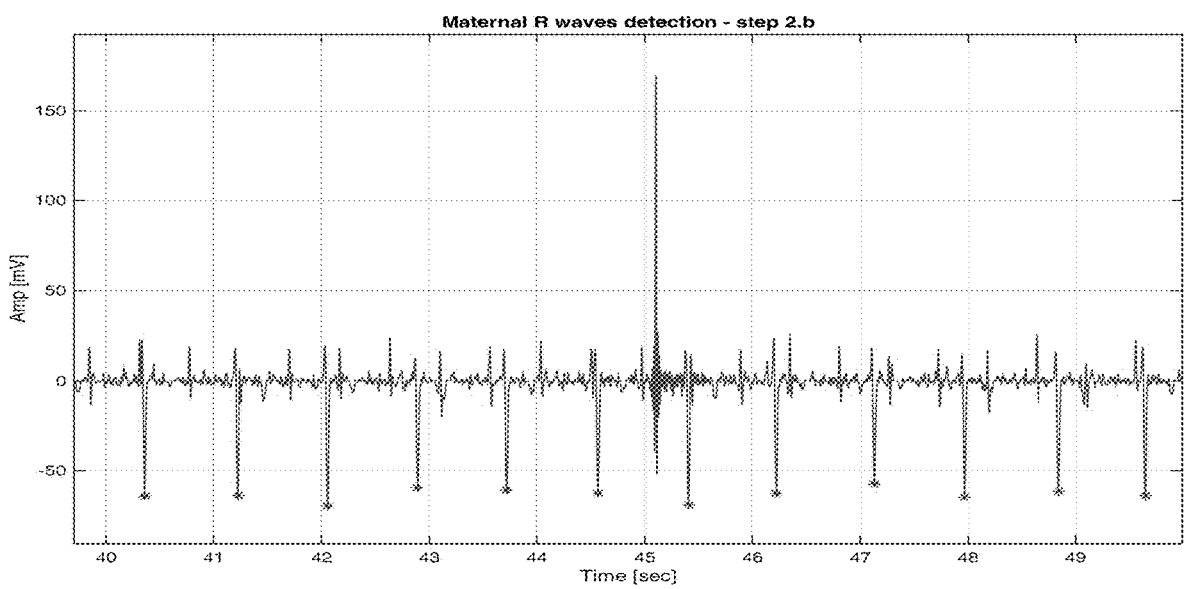
FIG. 6C shows a magnified view of a portion of the signal of FIG. 6B.

In some embodiments, the detection of R-wave peaks of step 220 continues with a peak re-detection process. In some embodiments, the peak re-detection process includes an automatic gain control ("AGC") analysis to detect windows with significantly different numbers of peaks. In some embodiments, the peak re-detection process includes a cross-correlation analysis. In some embodiments, the peak re-detection process includes an AGC analysis and a cross-correlation analysis. In some embodiments, an AGC analysis is appropriate for overcoming false negatives. In some embodiments, a cross-correlation analysis is appropriate for removing false positives. FIG. 6B shows a data signal following peak re-detection, with R-wave peaks re-detected as described above indicated with asterisks. FIG. 6C shows a magnified view of a portion of the data signal of FIG. 6B.

In some embodiments, the detection of R-wave peaks of step 220 continues with the construction of a global peaks array. In some embodiments, the global peaks array is created from multiple channels of data (e.g., each of which corresponds to one or more of the electrodes 310). In some embodiments, the signal of each channel is given a quality score based on the relative energy of the peaks. In some embodiments, the relative energy of a peak refers to the energy of the peak relative to the total energy of the signal under processing. In some embodiments, the energy of a peak is calculated by calculating a root mean square ("RMS") of the QRS complex containing the R-wave peak and the energy of a signal is calculated by calculating the RMS of the signal. In some embodiments, the relative energy of a peak is calculated by calculating a signal-to-noise ratio of the signal. In some embodiments, the channel having the highest quality score is deemed the "Best Lead". In some embodiments, the global peaks array is constructed based on the Best Lead, with signals from the other channels also considered based on a voting mechanism. In some embodiments, after the global peaks array has been constructed based on the Best Lead, each of the remaining channels "votes" on each peak. A channel votes positively (e.g., gives a vote value of "1") on a given peak that is included in the global peaks array constructed based on the best lead if it contains such peak (e.g., as detected in the peak detection described above), and votes negatively (e.g., gives a vote value of "0") if it does not contain such peak. Peaks that receive more votes are considered to be higher-quality peaks. In some embodiments, if a peak has greater than a threshold number of votes, it is retained in the global peaks array. In some embodiments, the threshold number of votes is half of the total number of channels. In some embodiments, if a peak has less than the threshold number of votes, additional testing is performed on the peak. In some embodiments, the additional testing includes calculating a correlation of the peak in the Best Lead channel with a template calculated as the average of all peaks. In some embodiments, if the correlation is greater than a first threshold correlation value, the peak is retained in the global peaks array. In some embodiments, the first threshold correlation value is 0.9. In some embodiments, if the correlation is less than the first threshold correlation value, a further correlation is calculated for all leads with positive votes for the peak (i.e., not just the Best Lead peak). In some embodiments, if the further correlation is greater than a second threshold correlation value, the peak is retained in the global peaks array, and if the further correlation is less than the second threshold correlation value, the peak is excluded from the global peaks array. In some embodiments, the second threshold correlation value is 0.85.

Figure 6D:
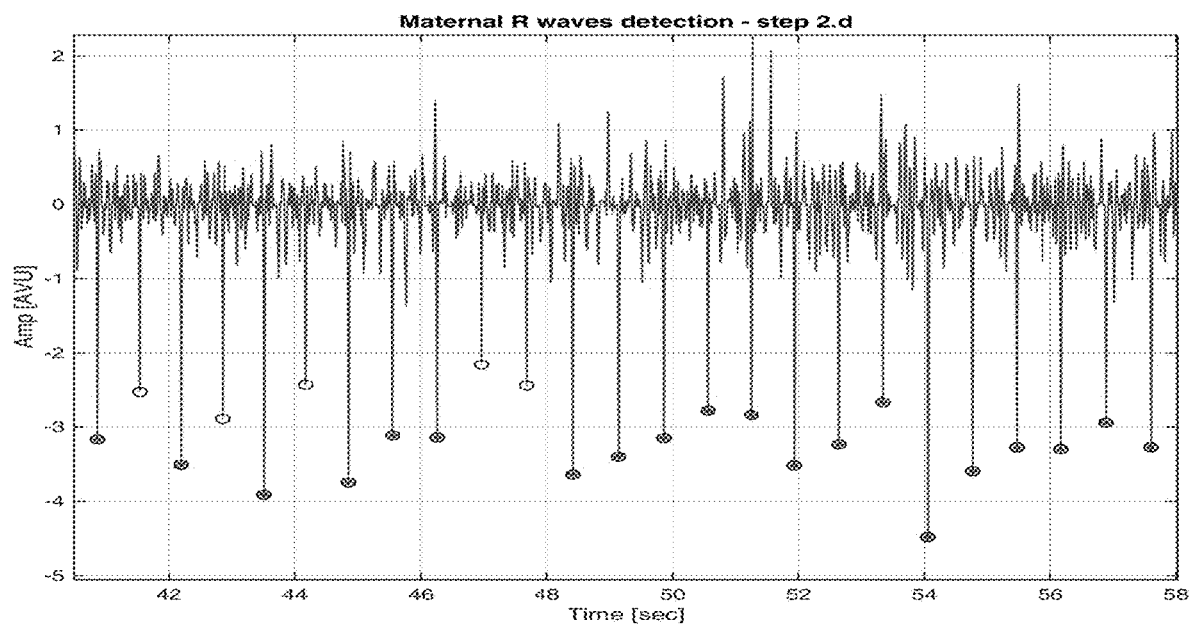
FIG. 6D shows the exemplary bio-potential signal of FIG. 6B after examination of the detected peaks.

In some embodiments, once created, the global peaks array is examined using physiological measures. In some embodiments, the examination is performed by the exemplary inventive computing device as described in U.S. Pat. No. 9,392,952, the contents of which are incorporated herein in their entirety. In some embodiments, the physiological parameters include R-R intervals, mean, and standard deviation; and heart rate and heart rate variability. In some embodiments, the examination includes cross-correlation to overcome false negatives. FIG. 6D shows a data signal following creation and examination of the global peaks array as described above. In FIG. 6D, peaks denoted by circled asterisks represent R-wave peaks that were detected previously (e.g., as shown in FIG. 6A), and circles with no asterisks represent R-wave peaks detected by cross-correlation to overcome false negatives as described above.

In some embodiments, if an initial step of R-wave detection was unsuccessful (i.e., if no R-wave peaks were detected over a given sample), an independent component analysis ("ICA") algorithm is applied to the data samples and the earlier portions of step 220 are repeated. In some embodiments, the exemplary ICA algorithm is, for example but not limited to, the FAST ICA algorithm. In some embodiments, the FAST ICA algorithm is, for example, utilized in accordance with Hyvarinen et al., "Independent component analysis: Algorithms and applications," Neural Networks 13 (4-5): 411-430 (2000).

Figure 7A:
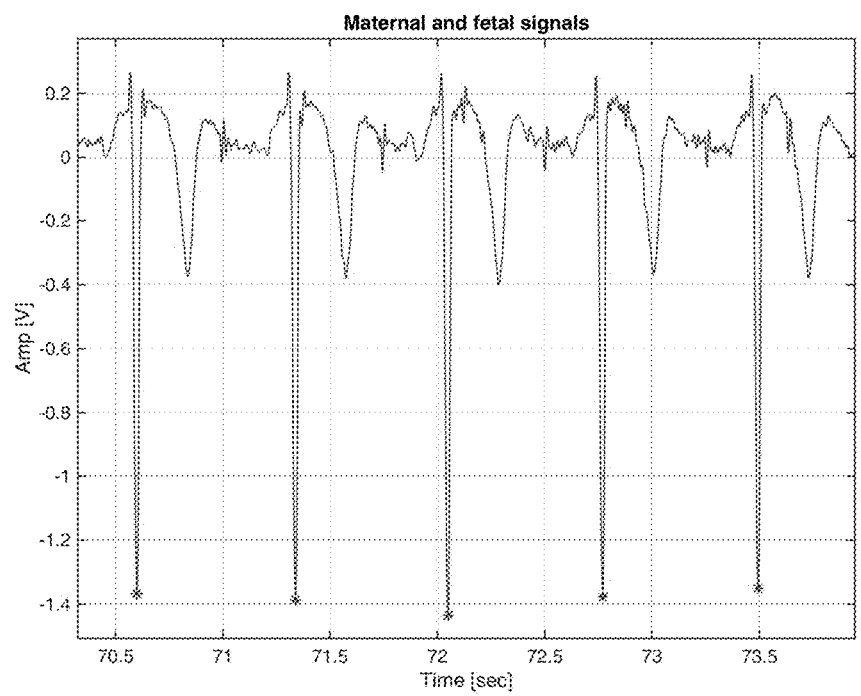
FIG. 7A shows a portion of an exemplary bio-potential signal including identified R-wave peaks.
Figure 7B:
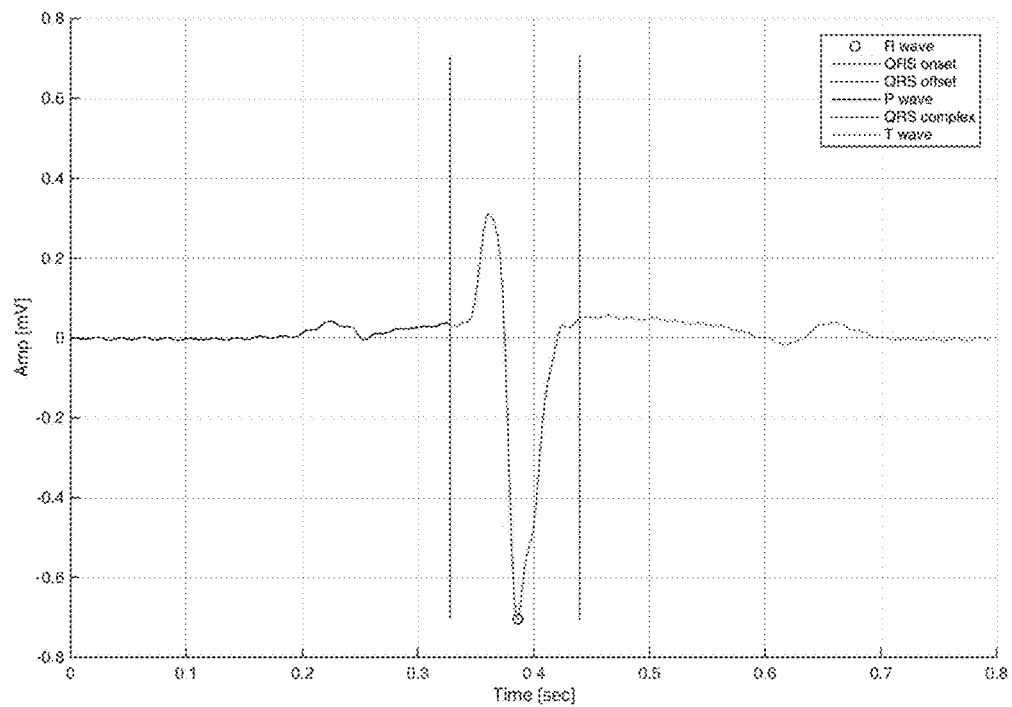
FIG. 7B shows a portion of an exemplary bio-potential signal having a P-wave, a QRS complex, and a T-wave identified therein.

Continuing to refer to FIG. 2, in step 230, the exemplary inventive computing device is programmed/configured to extract maternal ECG signals from signals that include both maternal and fetal data. In some embodiments, where the exemplary inventive computing device, programmed/configured to execute the method 200, receives maternal ECG signals as input after extraction from mixed maternal-fetal data, the exemplary inventive computing device is programmed/configured to skip step 230. FIG. 7A shows a portion of a signal in which R-wave peaks have been identified, and which includes both maternal and fetal signals. Without intending to be limited to any particular theory, the main challenge involved in the process of extracting maternal ECG signals is that each maternal heartbeat differs from all other maternal heartbeats. In some embodiments, this challenge is addressed by using an adaptive reconstruction scheme to identify each maternal heartbeat. In some embodiments, the extraction process begins by segmenting an ECG signal into a three-sourced signal. In some embodiments, this segmentation includes using a curve length transform to find a P-wave, a QRS complex, and a T-wave. In some embodiments, the curve length transform is as described in Zong et al., "A QT Interval Detection Algorithm Based On ECG Curve Length Transform," Computers In Cardiology 33:377-380 (October 2006). FIG. 7B shows an exemplary ECG signal including these portions.

Following the curve length transform, step 230 continues by using an adaptive template to extract the maternal signal. In some embodiments, template adaptation is used to isolate the current beat. In some embodiments, the extraction of the maternal signal using an adaptive template is performed as described in U.S. Pat. No. 9,392,952, the contents of which are incorporated herein by reference in their entirety. In some embodiments, this process includes beginning with a current template and adapting the current template using an iterative process to arrive at the current beat. In some embodiments, for each part of the signal (i.e., the P-wave, the QRS complex, and the T-wave), a multiplier is defined (referred to as P_mult, QRS_mult, and T_mult, respectively). In some embodiments, a shifting parameter is also defined. In some embodiments, the extraction uses a Levenberg-Marquardt non-linear least mean squares algorithm, as shown below:

$$P_{k+1} = P_k - [\partial_k^T \partial_k + \lambda_i \cdot \text{diag}(\partial_k^T \partial_k)]^{-1} * \partial_k^T [\phi_c(P_k) - \phi_m]$$

In some embodiments, the cost function is as shown below:

$$E = \|\phi_m - \phi_c\|^2$$

In the above expressions, $\phi_m$ represents the current beat ECG and $\phi_c$ represents the reconstructed ECG. In some embodiments, this method provides a local, stable, and repeatable solution. In some embodiments, iteration proceeds until the relative remaining energy has reached a threshold value. In some embodiments, the threshold value is between 0 db and −40 db. In some embodiments, the threshold value is between −10 db and −40 db. In some embodiments, the threshold value is between −20 db and −40 db. In some embodiments, the threshold value is between −30 db and −40 db. In some embodiments, the threshold value is between −10 db and −30 db. In some embodiments, the threshold value is between −10 db and −20 db. In some embodiments, the threshold value is between −20 db and −40 db. In some embodiments, the threshold value is between −20 db and −30 db. In some embodiments, the threshold value is between −30 db and −40 db. In some embodiments, the threshold value is between −25 db and −35 db. In some embodiments, the threshold value is about −20 db. In some embodiments, the threshold value is about −20 db.

Figure 7C:
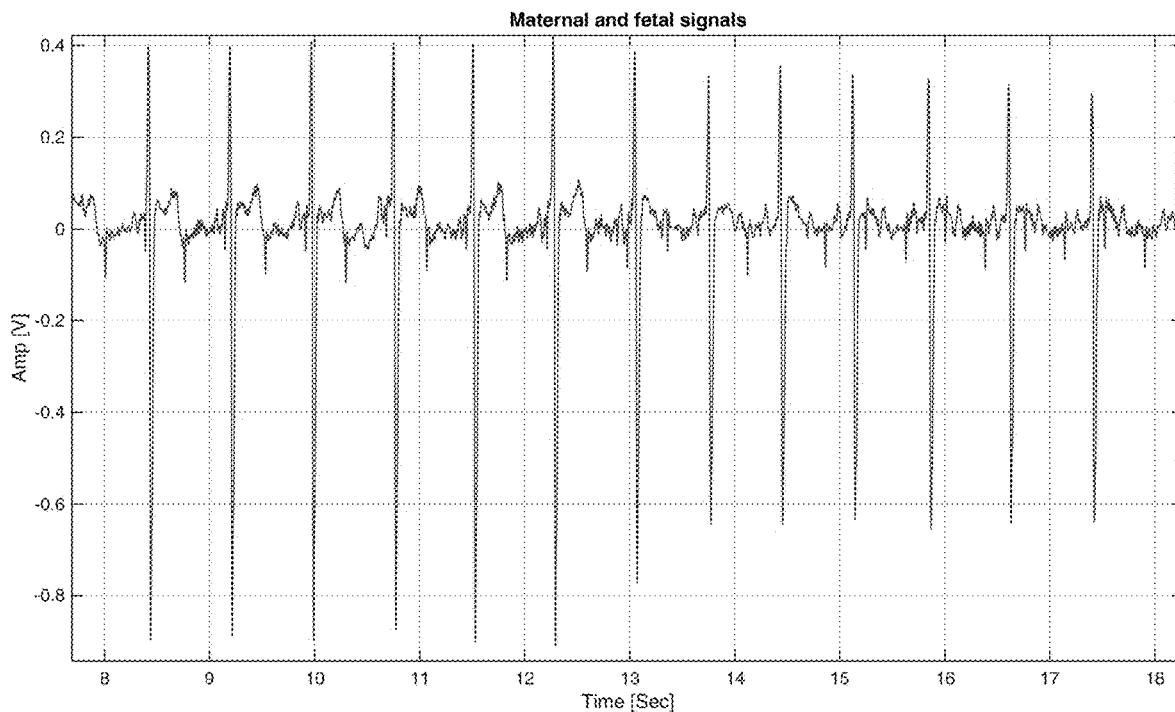
FIG. 7C shows an exemplary bio-potential signal including mixed maternal and fetal data.
Figure 7D:
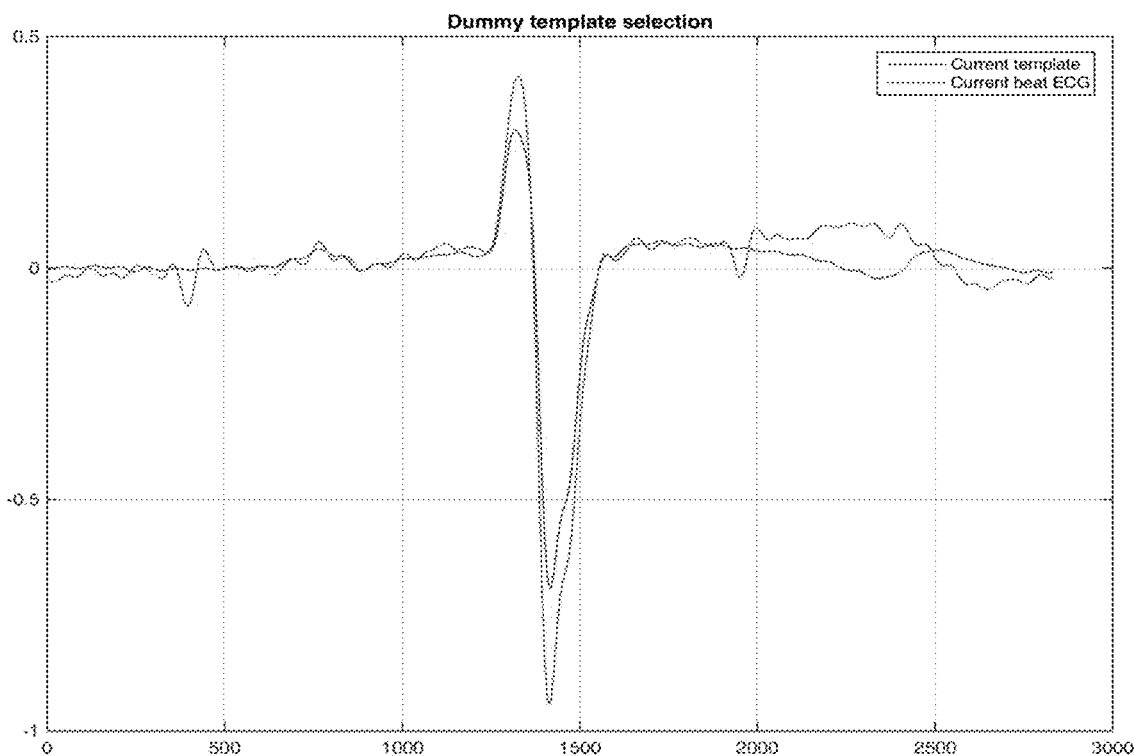
FIG. 7D shows a portion of the signal of FIG. 7C along with an initial template.
Figure 7E:
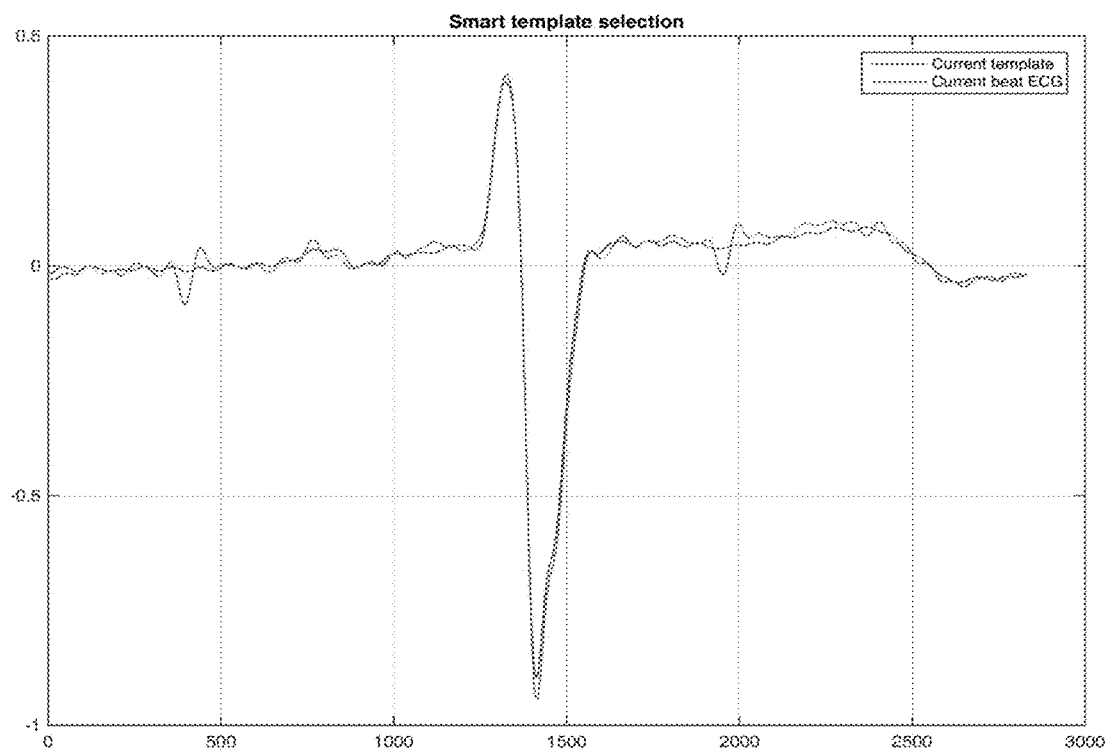
FIG. 7E shows a portion of the signal of FIG. 7C along with an adapted template.
Figure 7F:
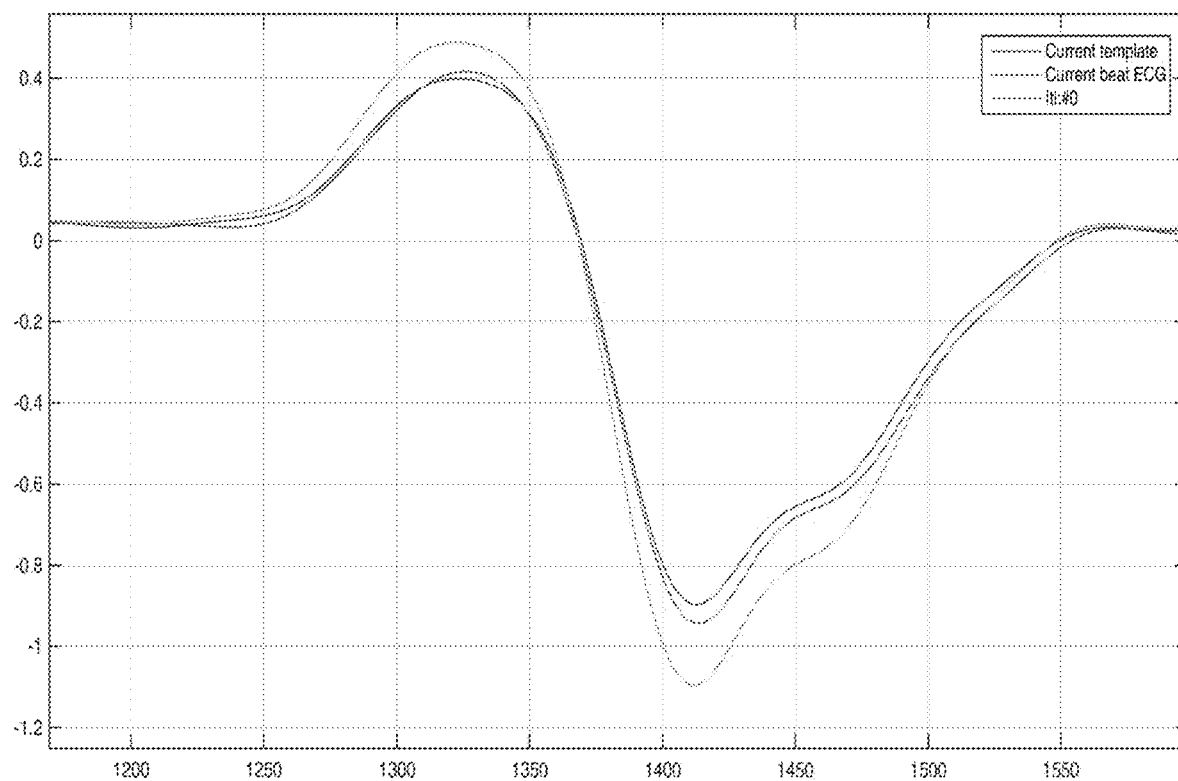
FIG. 7F shows a portion of the signal of FIG. 7C along with a current template and a zero-th iteration of an adaptation.
Figure 7G:
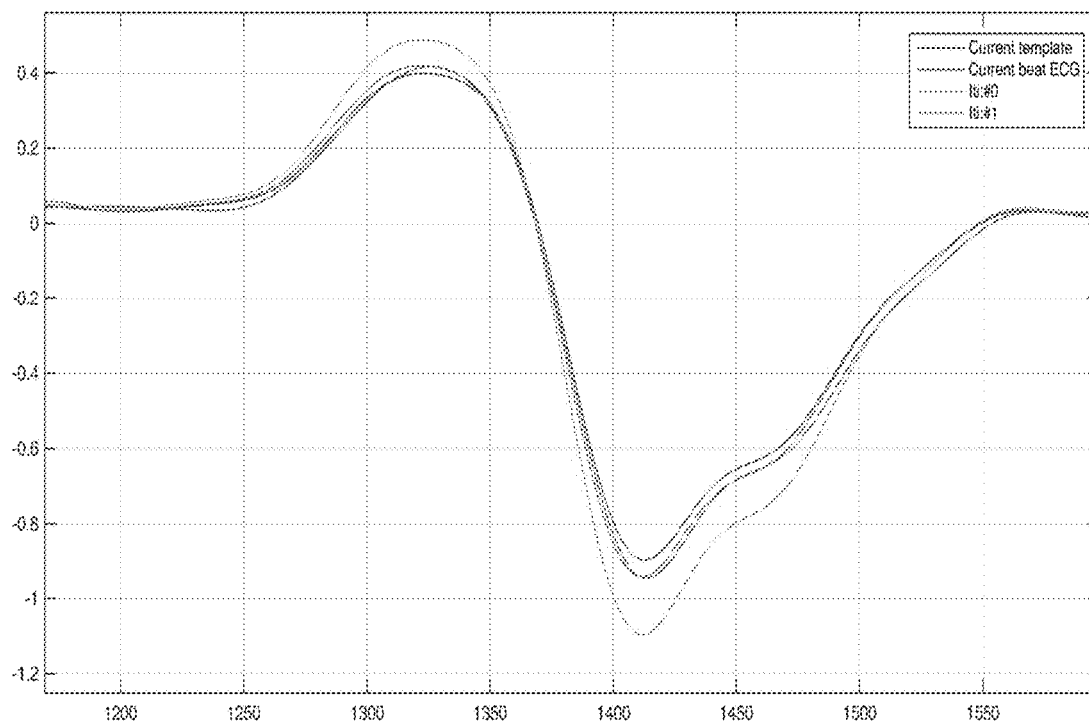
FIG. 7G shows a portion of the signal of FIG. 7C along with a current template, a zero-th iteration of an adaptation, and a first iteration of an adaptation.
Figure 7H:
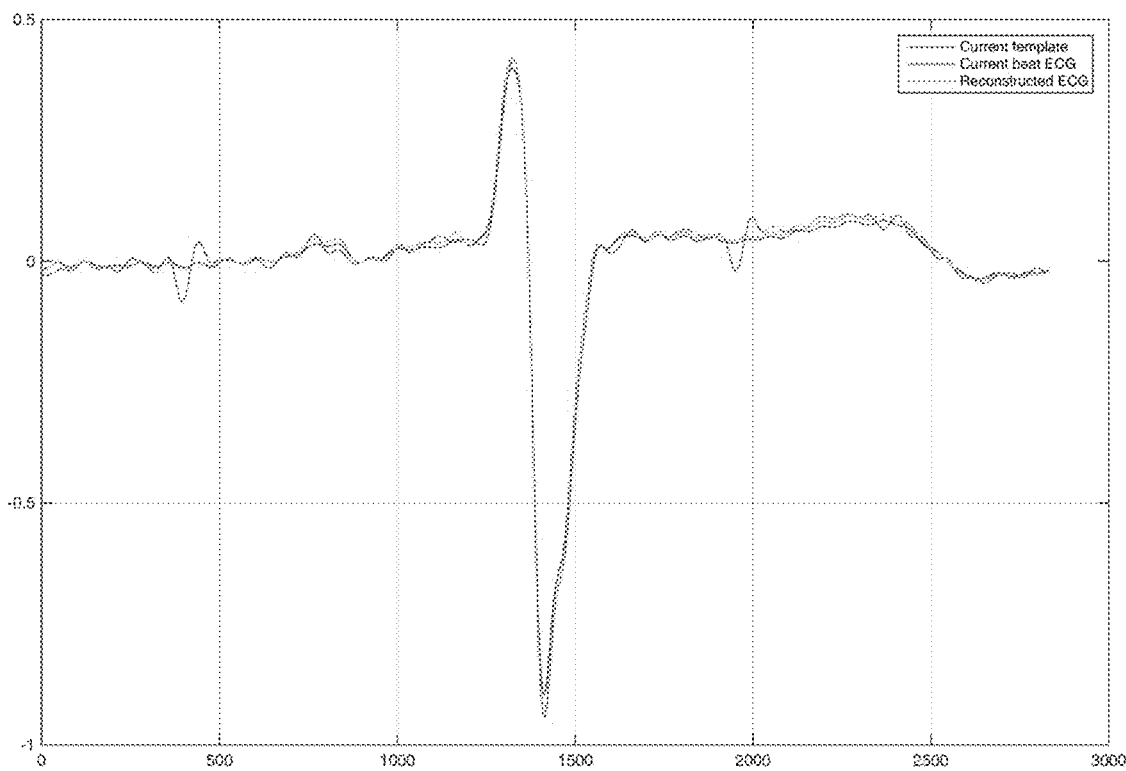
FIG. 7H shows a portion of the signal of FIG. 7C along with a current template and a maternal ECG signal reconstructed based on the current template.
Figure 7I:
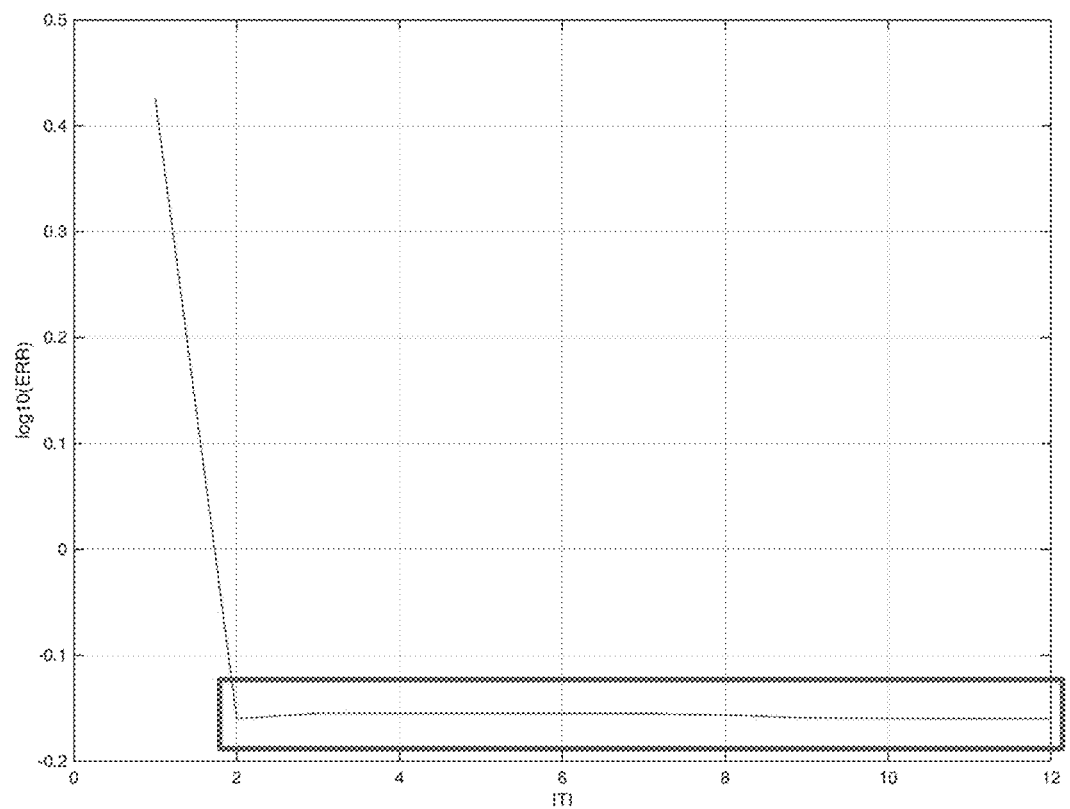
FIG. 7I shows the progress of an adaptation expressed in terms of the logarithm of the error signal as plotted against the number of the iteration.
Figure 7J:
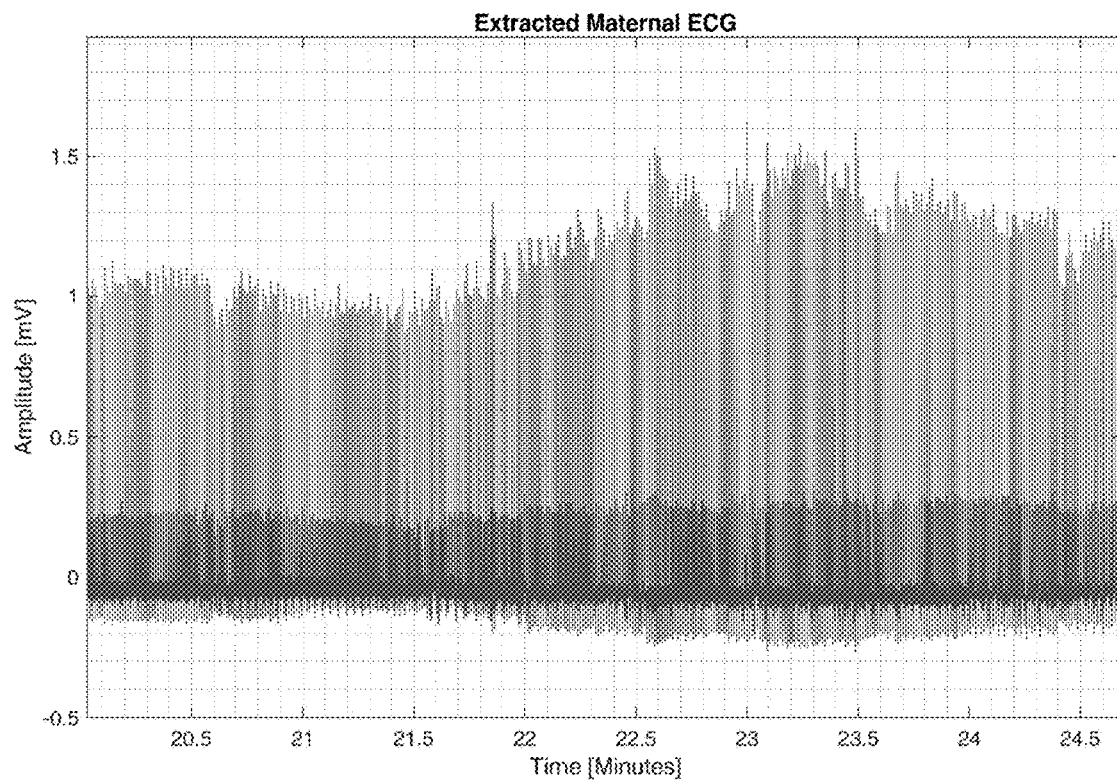
FIG. 7J shows an extracted maternal ECG signal.

FIG. 7C shows an exemplary signal including mixed maternal and fetal data. FIG. 7D shows a portion of the signal of FIG. 7C along with an initial template for comparison. FIG. 7E shows the portion of the signal of FIG. 7C along with an adapted template for comparison. FIG. 7F shows a portion of the signal of FIG. 7C, a current template, and a 0th iteration of the adaptation. FIG. 7G shows a portion of the signal of FIG. 7C, a current template, a 0th iteration of the adaptation, and a 1st iteration of the adaptation. FIG. 7H shows a portion of the signal of FIG. 7C, a current template, and an ECG signal (e.g., a maternal ECG signal) reconstructed based on the current template. FIG. 7I shows the progress of the adaptation in terms of the logarithm of the error signal against the number of the iteration. FIG. 7J shows an extracted maternal ECG signal.

Figure 8:
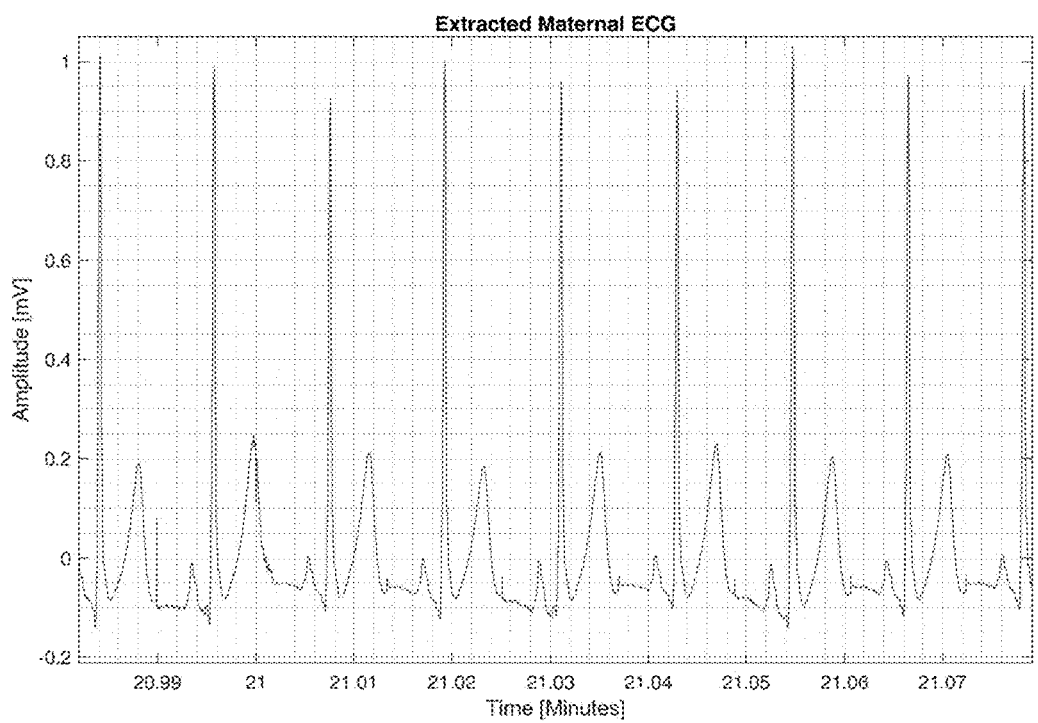
FIG. 8 shows an exemplary filtered maternal ECG signal.

Continuing to refer to FIG. 2, in step 240, the exemplary inventive computing device is programmed/configured to perform a signal cleanup on the maternal signals extracted in step 230. In some embodiments, the cleanup of step 240 includes filtering. In some embodiments, the filtering includes baseline removal using a moving average filter. In some embodiments, the filtering includes low pass filtering. In some embodiments, the low pass filtering is performed at between 25 Hz and 125 Hz. In some embodiments, the low pass filtering is performed at between 50 Hz and 100 Hz. In some embodiments, the low pass filtering is performed at 75 Hz. FIG. 8 shows a portion of an exemplary filtered maternal ECG following the performance of step 240.

Figure 9:
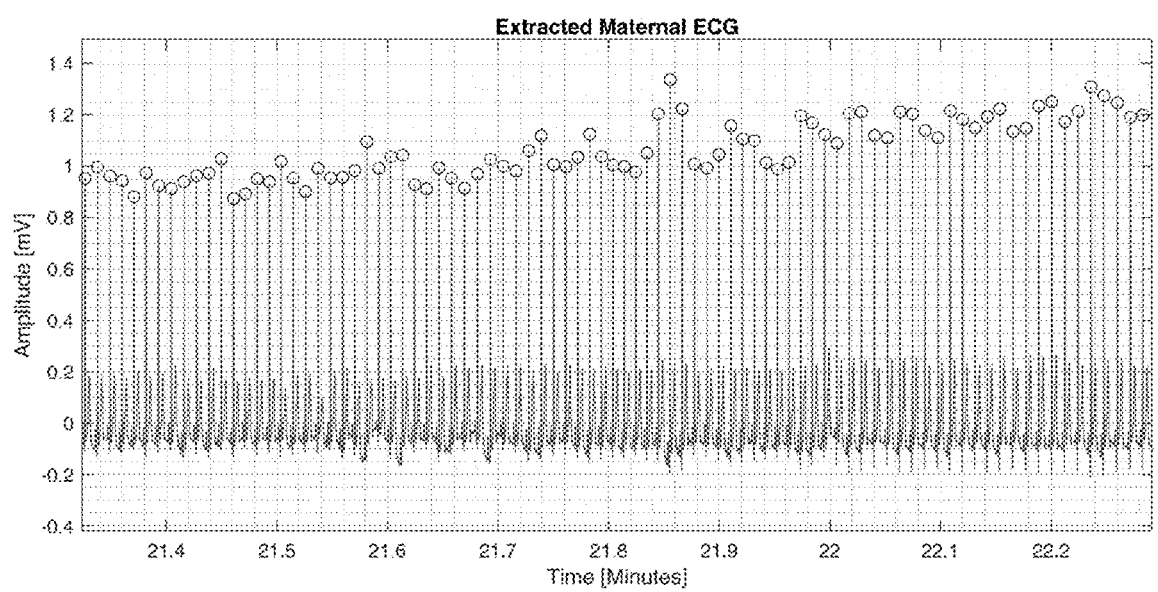
FIG. 9 shows an exemplary maternal ECG signal with R-wave peaks annotated therein.

Continuing to refer to FIG. 2, in step 250, the exemplary inventive computing device is programmed/configured to calculate R-wave amplitudes for the filtered maternal ECG signals resulting from the performance of step 240. In some embodiments, R-wave amplitudes are calculated based on the maternal ECG peaks that were detected in step 220 and the maternal ECG signals that were extracted in step 230. In some embodiments, step 250 includes calculating the amplitude of the various R-waves. In some embodiments, the amplitude is calculated as the value (e.g., signal amplitude) of the maternal ECG signals at each detected peak position. FIG. 9 shows an exemplary extracted maternal ECG signal with R-wave peaks annotated with circles.

Figure 10A:
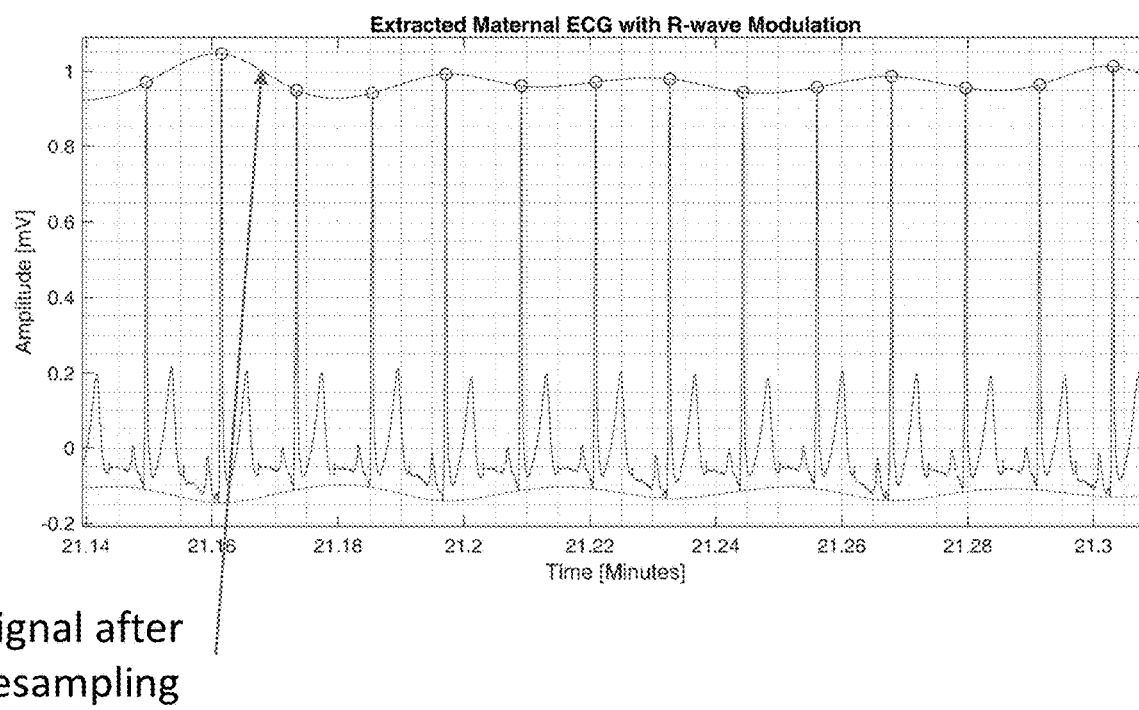
FIG. 10A shows an exemplary R-wave amplitude signal.
Figure 10B:
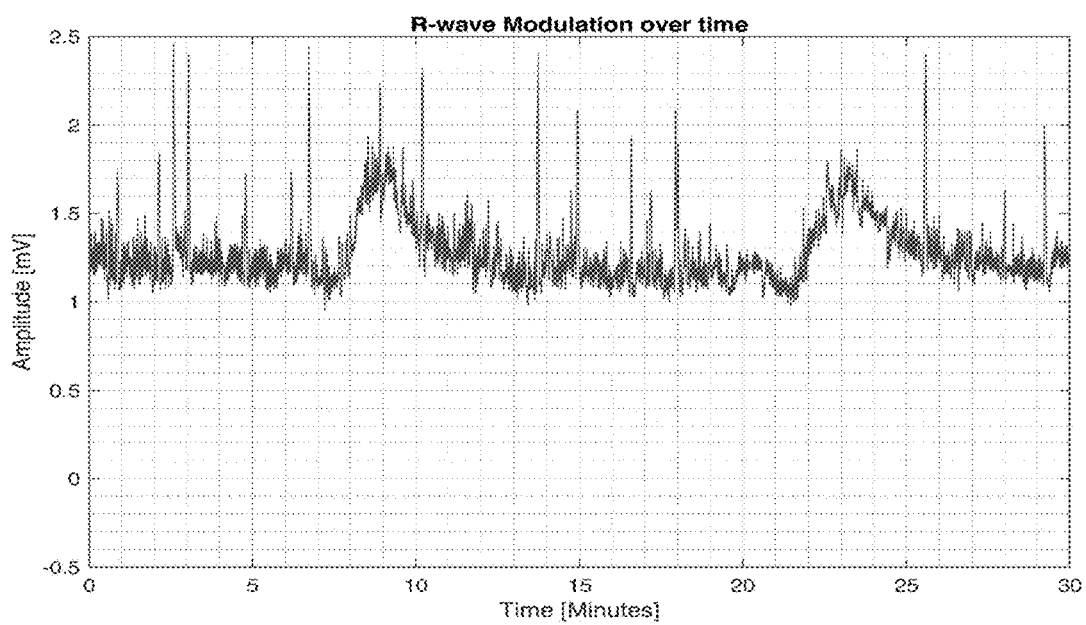
FIG. 10B shows an exemplary modulated R-wave amplitude signal.

Continuing to refer to FIG. 2, in step 260, the exemplary inventive computing device is programmed/configured to create an R-wave amplitude signal over time based on the R-wave amplitudes that were calculated in step 250. In some embodiments, the calculated R-wave peaks are not sampled uniformly over time. Accordingly, in some embodiments, step 260 is performed in order to re-sample the R-wave amplitudes in a way such that they will be uniformly sampled over time (e.g., such that the difference in time between each two adjacent samples is constant). In some embodiments, step 260 is performed by connecting the R-wave amplitude values that were calculated in step 250 and re-sampling the connected R-wave amplitude values. In some embodiments, the re-sampling includes interpolation with defined query points in time. In some embodiments, the interpolation includes linear interpolation. In some embodiments, the interpolation includes spline interpolation. In some embodiments, the interpolation includes cubic interpolation. In some embodiments, the query points define the points in time at which interpolation should occur. FIG. 10A shows an exemplary R-wave amplitude signal as created in step 260 based on the R-wave amplitudes from step 250. In FIG. 10A, the maternal ECG is similar to that shown in FIG. 8, the detected R-wave peaks are shown in circles, and the R-wave amplitude signal is the curve connecting the circles. FIG. 10B shows the modulation of the R-wave amplitude signal over a larger time window.

Figure 11A:
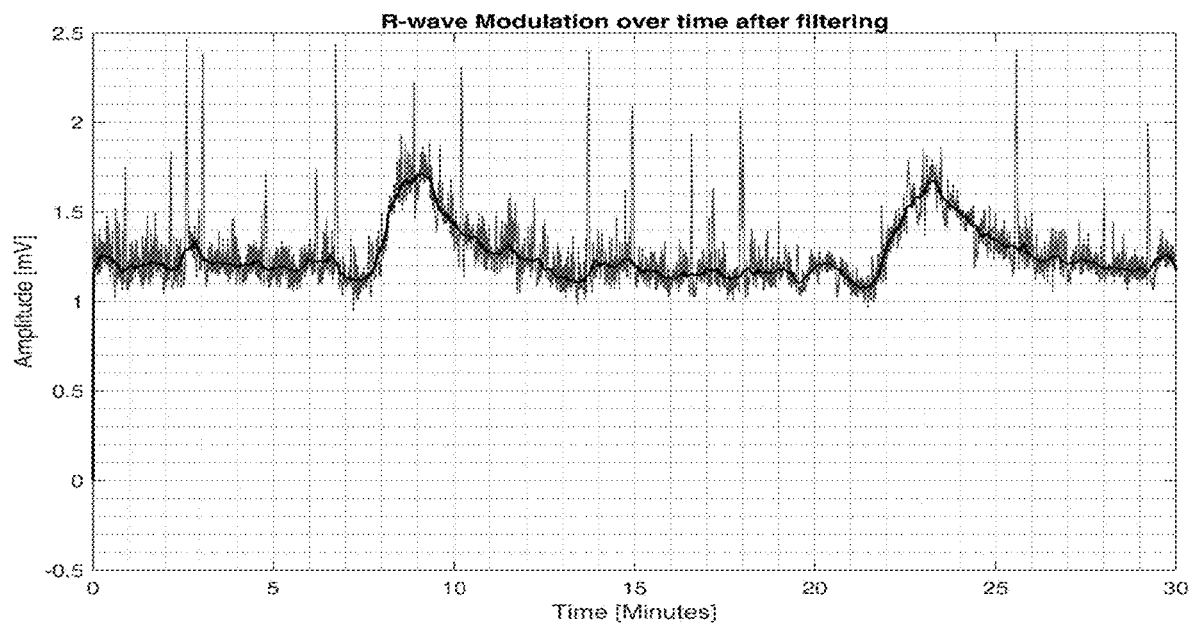
FIG. 11A shows an exemplary modulated R-wave amplitude signal along with the result of the application of a moving average filter thereto.
Figure 11B:
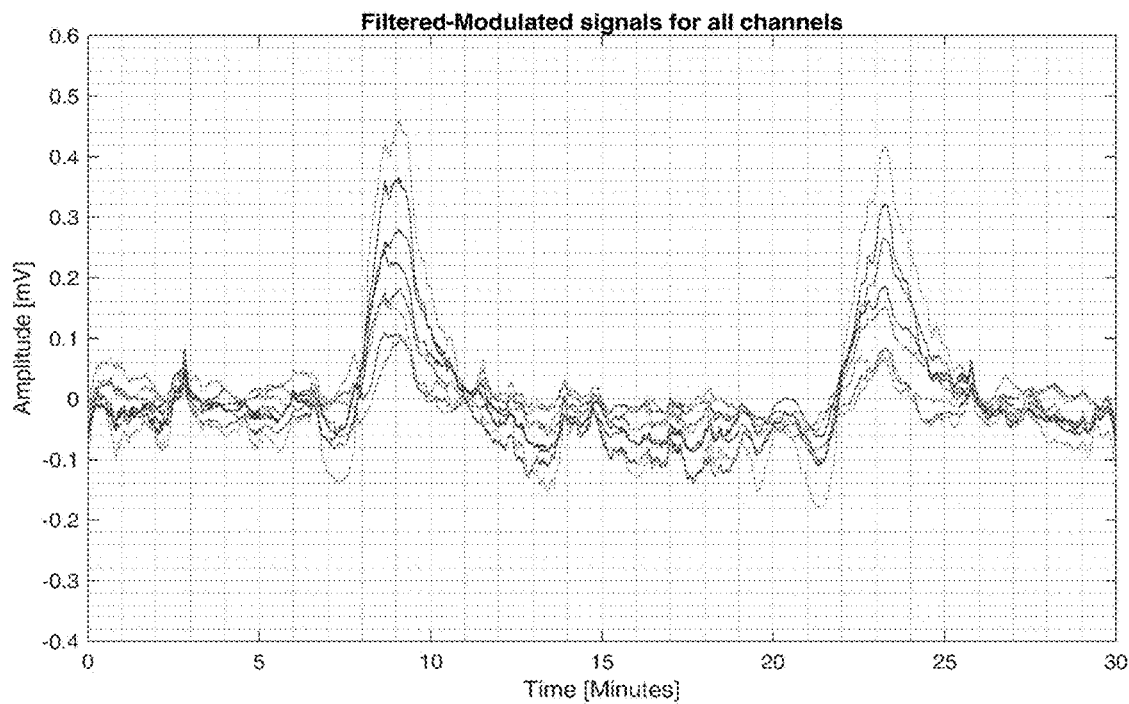
FIG. 11B shows exemplary filtered R-wave amplitude signals for multiple channels over a same time window.

Continuing to refer to FIG. 2, in step 270, the exemplary inventive computing device is programmed/configured to clean up the R-wave amplitude signal by applying a moving average filter. In some embodiments, the moving average filter is applied to clean the high-frequency changes in the R-wave amplitude signal. In some embodiments, the moving average filter is applied over a predetermined time window. In some embodiments, the time window has a length of between one second and ten minutes. In some embodiments, the time window has a length of between one second and one minute. In some embodiments, the time window has a length of between one second and 30 seconds. In some embodiments, the time window has a length of twenty seconds. FIG. 11A shows the R-wave amplitude signal of FIG. 10B, with the signal resulting from the application of the moving average filter shown in a thick line along the middle of the R-wave amplitude signal. As noted above, in some embodiments, multiple channels of data are considered as input for the method 200. FIG. 11B shows a plot of filtered R-wave amplitude signals for multiple channels over the same time window.

Figure 12A:
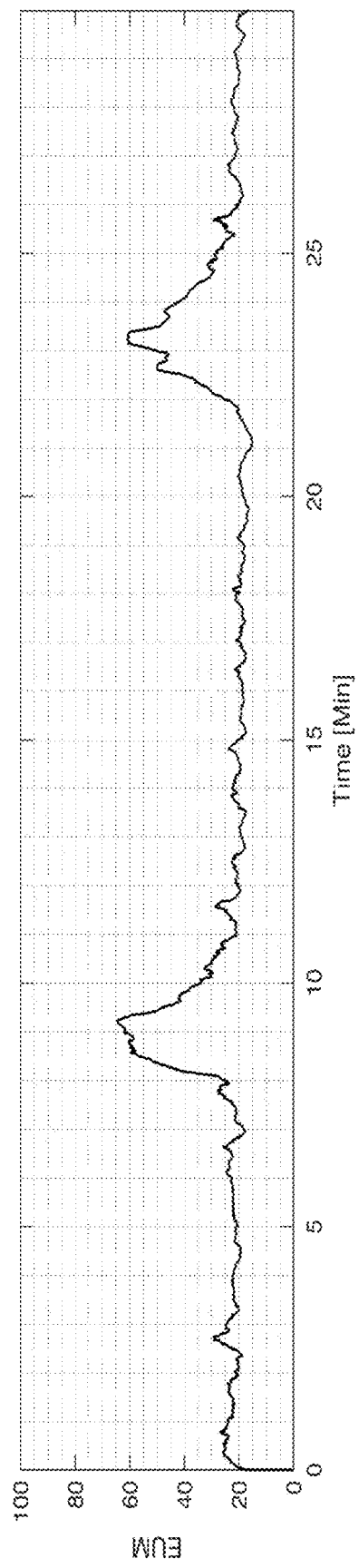
FIG. 12A shows a first exemplary normalized electrical uterine signal generated based on the exemplary filtered R-wave amplitude signals shown in FIG. 11B.
Figure 12B:
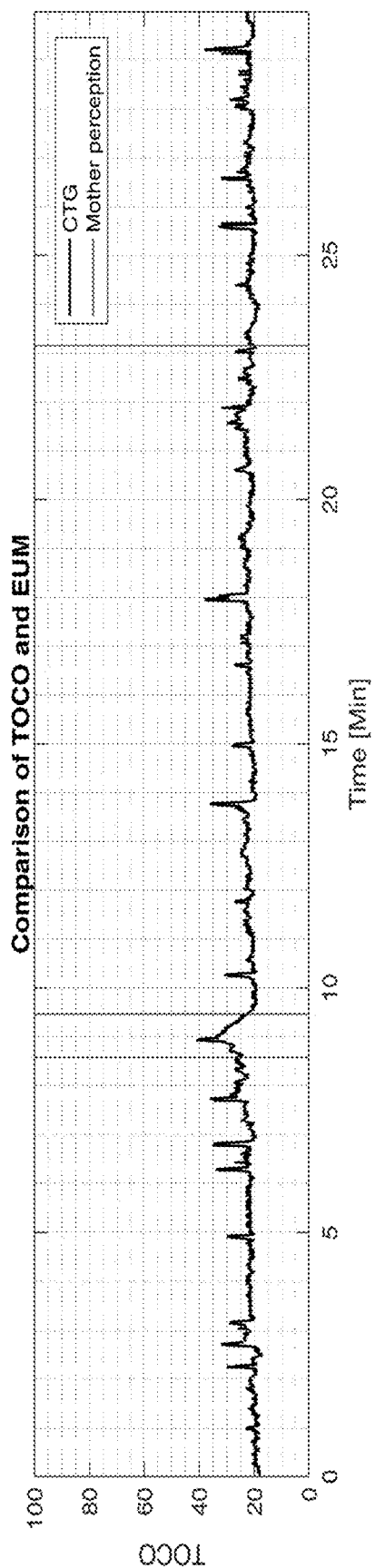
FIG. 12B shows a first tocograph signal recorded over the same time period as the exemplary normalized electrical uterine signal with self-reported contractions annotated therein.

Continuing to refer to FIG. 2, in step 280, the exemplary inventive computing device is programmed/configured to calculate the average signal of all the filtered R-wave signals (e.g., as shown in FIG. 11B) per unit of time. In some embodiments, at each point in time for which a sample exists, a single average signal is calculated. In some embodiments, the average signal is the 80th percentile of all the signals at each point in time. In some embodiments, the average signal is the 85th percentile of all the signals at each point in time. In some embodiments, the average signal is the 90th percentile of all the signals at each point in time. In some embodiments, the average signal is the 95th percentile of all the signals at each point in time. In some embodiments, the average signal is the 99th percentile of all the signals at each point in time. In some embodiments, the result of this averaging is a single signal with uniform sampling over time. In step 290, the exemplary inventive computing device is programmed/configured to normalize the signal calculated in step 280. In some embodiments, the signal is normalized by dividing by a constant factor. In some embodiments, the constant factor is between 2 volts and 1000 volts. In some embodiments, the constant factor is 50 volts. FIG. 12A shows an exemplary normalized electrical uterine signal following the performance of steps 280 and 290. FIG. 12B shows a tocograph signal generated over the same time period, with contractions self-reported by the mother indicated by vertical lines. Referring to FIGS. 12A and 12B, it can be seen that the peaks in the exemplary normalized electrical uterine signal in FIG. 12A coincide with the self-reported contractions shown in FIG. 12B. Accordingly, in some embodiments, a normalized electrical uterine monitoring ("EUM") signal produced through the performance of the exemplary method 200 (e.g., the signal shown in 12A) is suitable for use to identify contractions. In some embodiments, a contraction is identified by identifying a peak in the EUM signal.

In some embodiments, the present invention is directed to a specifically programmed computer system, including at least the following components: a non-transient memory, electronically storing computer-executable program code; and at least one computer processor that, when executing the program code, becomes a specifically programmed computing processor that is configured to perform at least the following operations: receiving a plurality of bio-potential signals collected at a plurality of locations on the abdomen of a pregnant mother; detecting R-wave peaks in the bio-potential signals; extracting maternal electrocardiogram ("ECG") signals from the bio-potential signals; determining R-wave amplitudes in the maternal ECG signals; creating an R-wave amplitude signal for each of the maternal ECG signals; calculating an average of all the R-wave amplitude signals; and normalizing the average to produce an electrical uterine monitoring ("EUM") signal. In some embodiments, the operations also include identifying at least one uterine contraction based on a corresponding at least one peak in the EUM signal.

Figure 13:
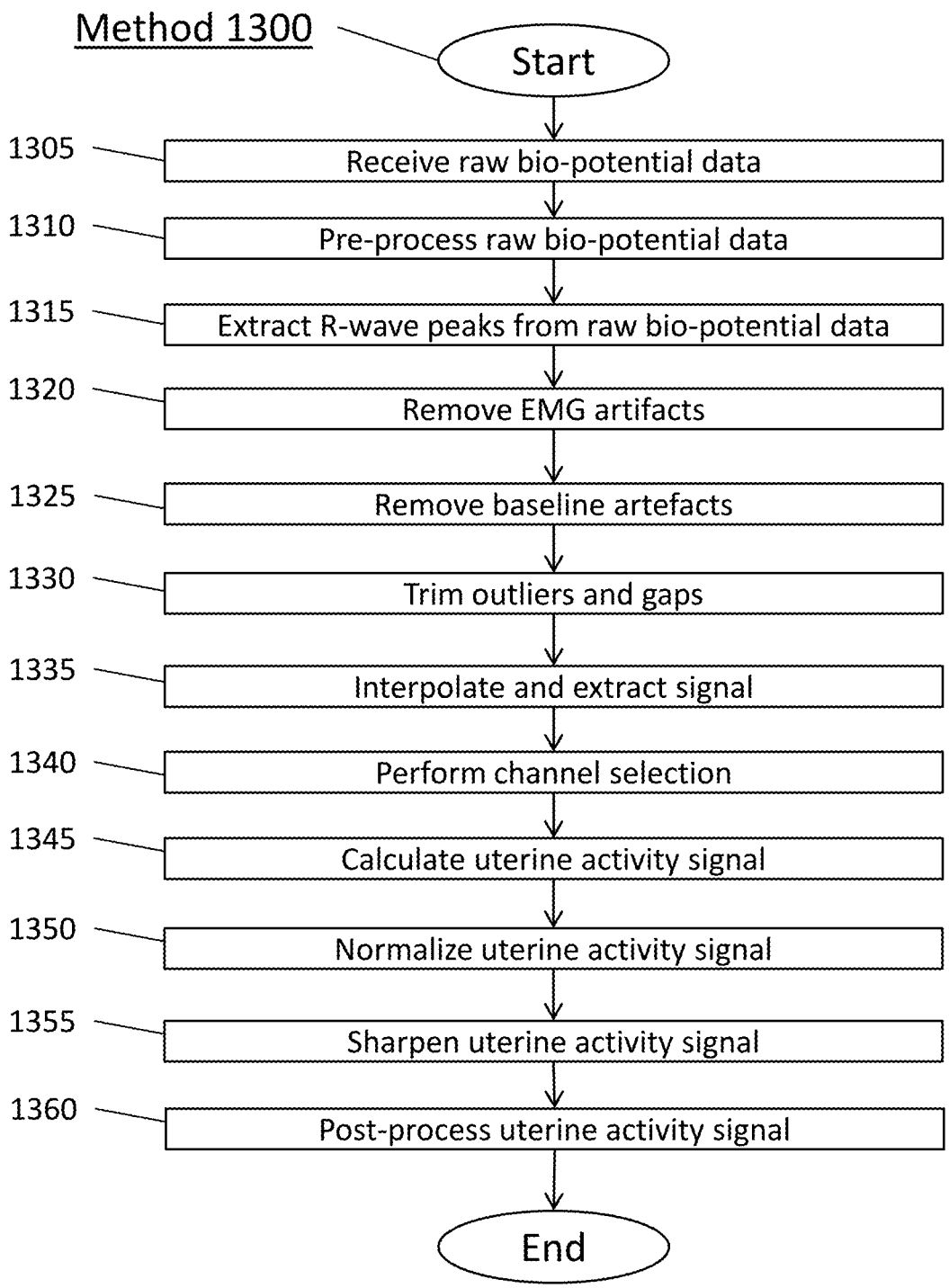
FIG. 13 shows a flowchart of a second exemplary method.

FIG. 13 shows a flowchart of an exemplary inventive method 1300. In some embodiments, an exemplary inventive computing device, programmed/configured in accordance with the method 1300, is operative to receive, as input, raw bio-potential data measured by a plurality of electrodes positioned on the skin of a pregnant human subject, and analyze such input to produce a tocograph-like signal. In some embodiments, the quantity of electrodes is between 2 and 10. In some embodiments, the quantity of electrodes is between 2 and 20. In some embodiments, the quantity of electrodes is between 2 and 30. In some embodiments, the quantity of electrodes is between 2 and 40. In some embodiments, the quantity of electrodes is between 4 and 10. In some embodiments, the quantity of electrodes is between 4 and 20. In some embodiments, the quantity of electrodes is between 4 and 30. In some embodiments, the quantity of electrodes is between 4 and 40. In some embodiments, the quantity of electrodes is between 6 and 10. In some embodiments, the quantity of electrodes is between 6 and 20. In some embodiments, the quantity of electrodes is between 6 and 30. In some embodiments, the quantity of electrodes is between 6 and 40. In some embodiments, the quantity of electrodes is between 8 and 10. In some embodiments, the quantity of electrodes is between 8 and 20. In some embodiments, the quantity of electrodes is between 8 and 30. In some embodiments, the quantity of electrodes is between 8 and 40. In some embodiments, the quantity of electrodes is 8. In some embodiments, the exemplary inventive computing device, programmed/configured in accordance with the method 1300, is operative to receive, as input, maternal ECG signals that have already been extracted from raw bio-potential data (e.g., by separation from fetal ECG signals that form part of the same raw bio-potential data). In some embodiments, the exemplary inventive computing device is programmed/configured in accordance with the method 1300 via instructions stored in a non-transitory computer-readable medium. In some embodiments, the exemplary inventive computing device includes at least one computer processor, which, when executing the instructions, becomes a specifically-programmed computer processor programmed/configured in accordance with the method 1300.

In some embodiments, the exemplary inventive computing device is programmed/configured to continuously perform one or more steps of the method 1300 along a moving time window. In some embodiments, the moving time window has a predefined length. In some embodiments, the predefined length is sixty seconds. In some embodiments, the exemplary inventive computing device is programmed/configured to continuously perform one or more steps of the method 1300 along a moving time window having a length that is between one second and one hour. In some embodiments, the length of the moving time window is between thirty seconds and 30 minutes. In some embodiments, the length of the moving time window is between 30 seconds and 10 minutes. In some embodiments, the length of the moving time window is between 30 seconds and 5 minutes. In some embodiments, the length of the moving time window is about 60 seconds. In some embodiments, the length of the moving time window is 60 seconds.

In step 1305, the exemplary inventive computing device is programmed/configured to receive raw bio-potential data as input. Exemplary raw bio-potential data is shown in FIGS. 18A, 18C, 18E, and 18G. In some embodiments, the raw bio-potential data is recorded through the use of at least two electrodes positioned in proximity to a pregnant subject's skin. In some embodiments, at least one of the electrodes is a signal electrode. In some embodiments at least one of the electrodes is a reference electrode. In some embodiments, the reference electrode is located at a point away from the uterus of the subject. In some embodiments, a bio-potential signal is recorded at each of several points around the pregnant subject's abdomen. In some embodiments, a bio-potential signal is recorded at each of eight points around the pregnant subject's abdomen. In some embodiments, the bio-potential data is recorded at 1,000 samples per second. In some embodiments, the bio-potential data is up-sampled to 1,000 samples per second. In some embodiments, the bio-potential data is recorded at a sampling rate of between 100 and 10,000 samples per second. In some embodiments, the bio-potential data is up-sampled to a sampling rate of between 100 and 10,000 samples per second. In some embodiments, the steps of the method 1300 between receipt of raw data and channel selection (i.e., step 1310 through step 1335) are performed on each of a plurality of signal channels, wherein each signal channel is generated by the exemplary inventive computing device as the difference between the bio-potential signals recorded by a specific pair of the electrodes. In some embodiments, in which the method 1300 is performed through the use of data recorded at electrodes located as shown in FIGS. 4A and 4B, channels are identified as follows:

Channel 1: A1-A4
Channel 2: A2-A3
Channel 3: A2-A4
Channel 4: A4-A3
Channel 5: B1-B3
Channel 6: B1-B2
Channel 7: B3-B2
Channel 8: A1-A3

In step 1310, the exemplary inventive computing device is programmed/configured to pre-process the signal channels determined based on the raw bio-potential data to produce a plurality of pre-processed signal channels. In some embodiments, the pre-processing includes one or more filters. In some embodiments, the pre-processing includes more than one filter. In some embodiments, the pre-processing includes a DC removal filter, a powerline filter, and a high pass filter. In some embodiments, a DC removal filter removes the raw data's mean at the current processing interval. In some embodiments, the powerline filter includes a 10$^{th}$-order band-stop infinite impulse response ("BR") filter that is configured to minimize any noise at a preconfigured frequency in the data. In some embodiments, the preconfigured frequency is 50 Hz and the powerline filter includes cutoff frequencies of 49.5 Hz and 50.5 Hz. In some embodiments, the preconfigured frequency is 60 Hz and the powerline filter includes cutoff frequencies of 59.5 Hz and 60.5 Hz. In some embodiments, high pass filtering is performed by subtracting a wandering baseline from the signal, where the baseline is calculated through a moving average window having a predetermined length. In some embodiments, the predetermined length is between 50 milliseconds and 350 milliseconds. In some embodiments, the predetermined length is between 100 milliseconds and 300 milliseconds. In some embodiments, the predetermined length is between 150 milliseconds and 250 milliseconds. In some embodiments, the predetermined length is between 175 milliseconds and 225 milliseconds. In some embodiments, the predetermined length is about 200 milliseconds. In some embodiments, the predetermined length is 201 milliseconds (i.e., 50 samples at a sampling rate of 250 samples per second) long. In some embodiments, the baseline includes data from frequencies lower than 5 Hz, and thus the signal is high pass filtered at about 5 Hz. Pre-processed data generated based on the raw bio-potential data shown in FIGS. 18A, 18C, 18E, and 18G is shown in FIGS. 18B, 18D, 18F, and 18H, respectively.

Figure 18A:
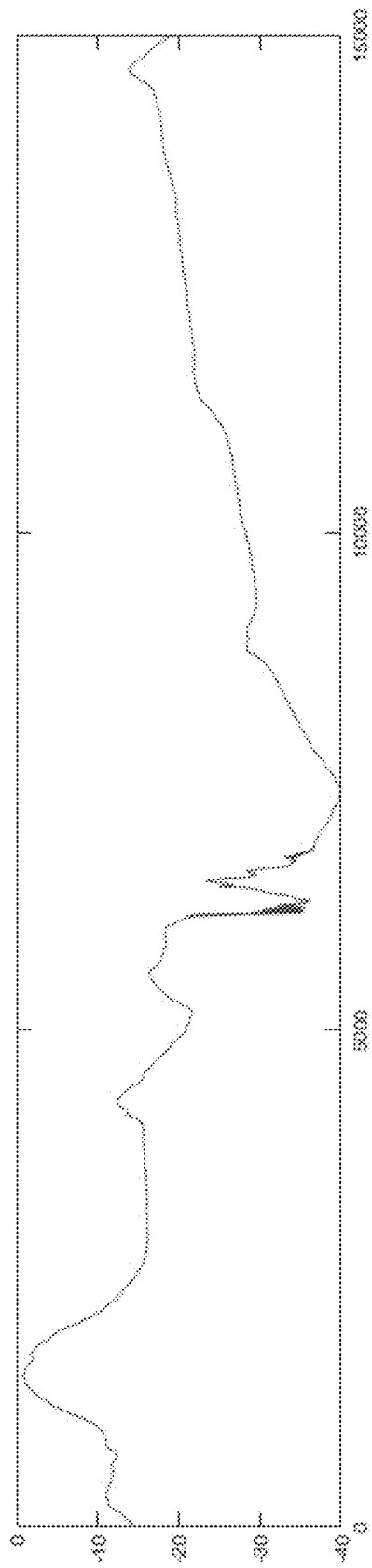
FIG. 18A shows an exemplary raw bio-potential data set.
Figure 18B:
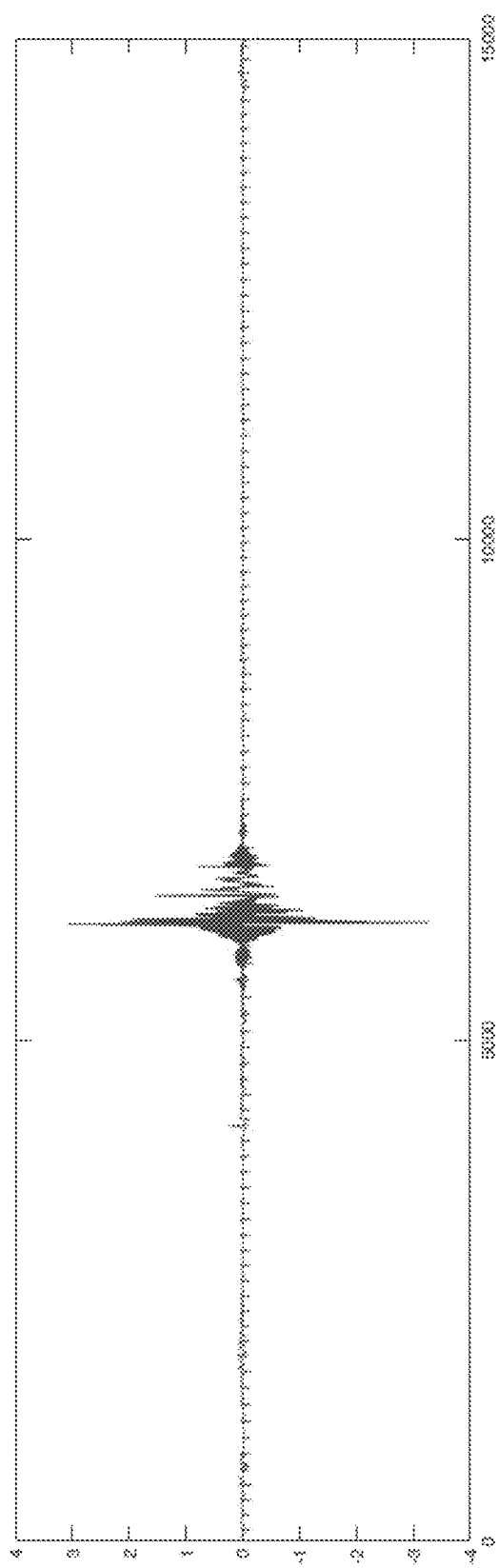
FIG. 18B shows an exemplary filtered data set based on the exemplary raw data set of FIG. 18A.
Figure 18C:
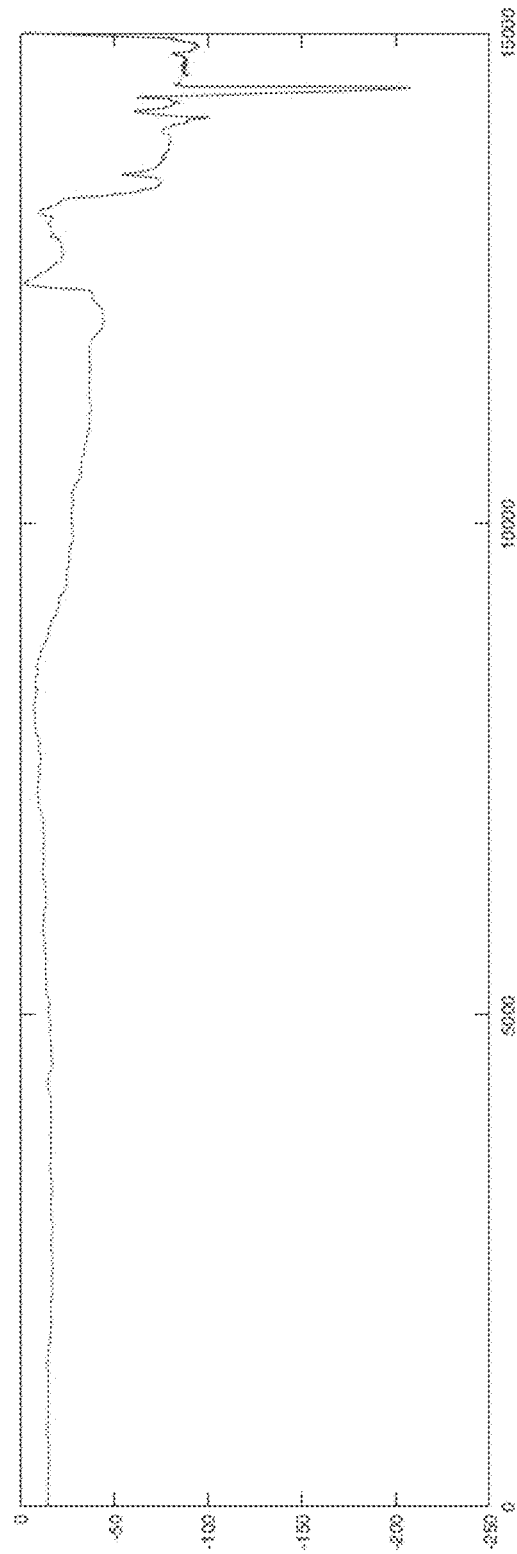
FIG. 18C shows an exemplary raw bio-potential data set.
Figure 18D:
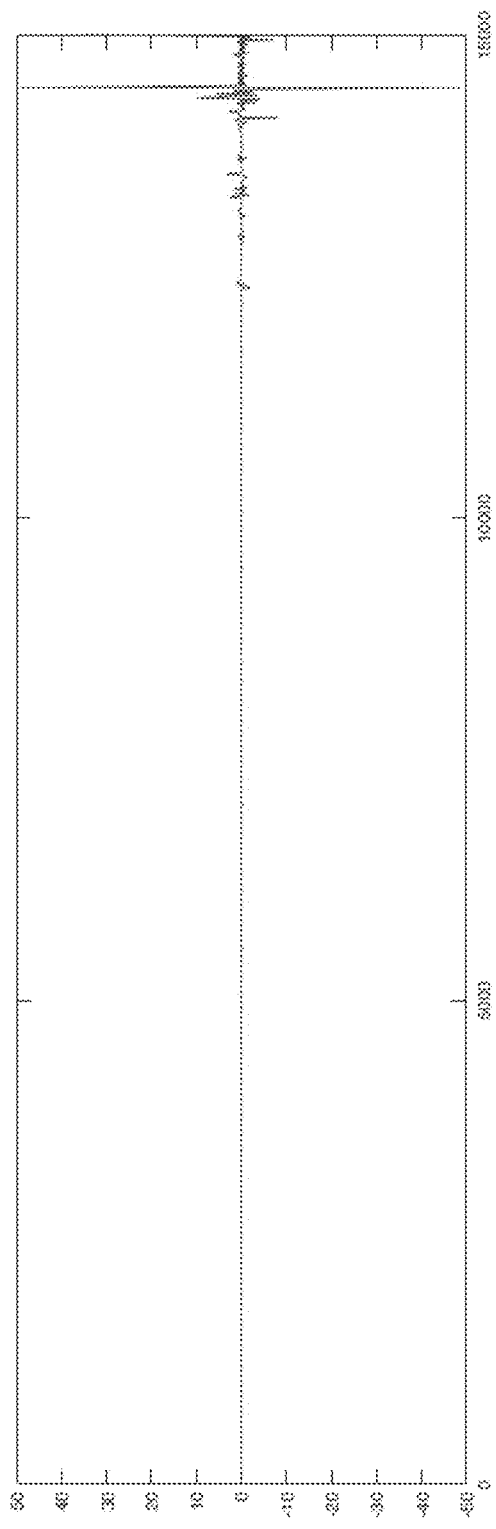
FIG. 18D shows an exemplary filtered data set based on the exemplary raw data set of FIG. 18C.
Figure 18E:
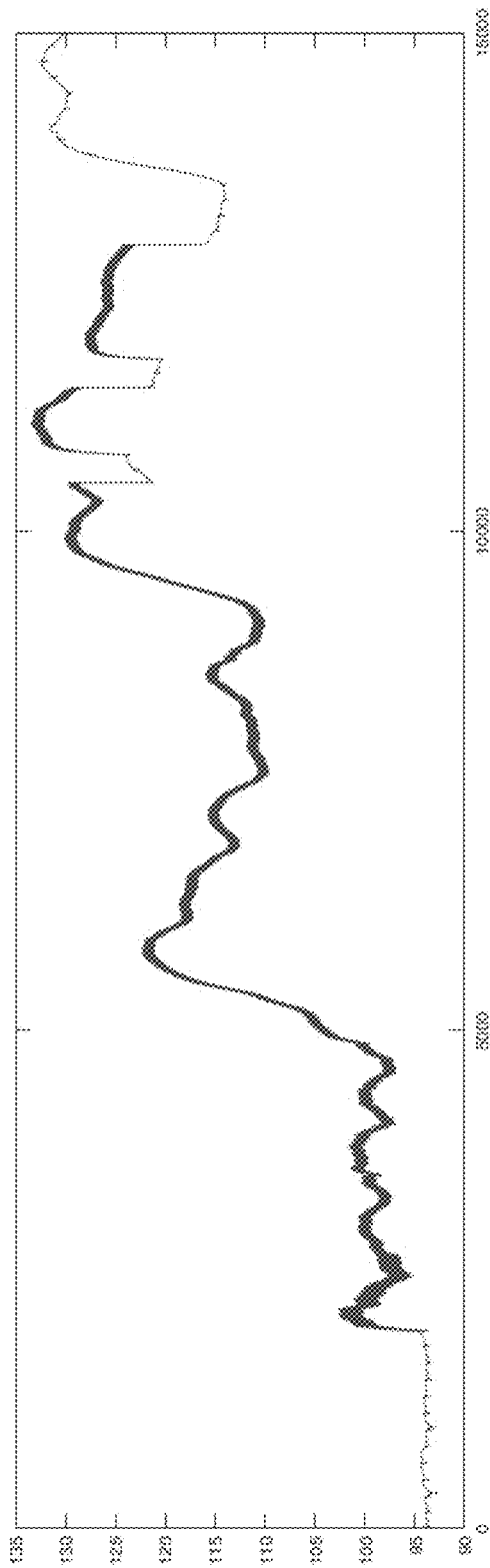
FIG. 18E shows an exemplary raw bio-potential data set.
Figure 18F:
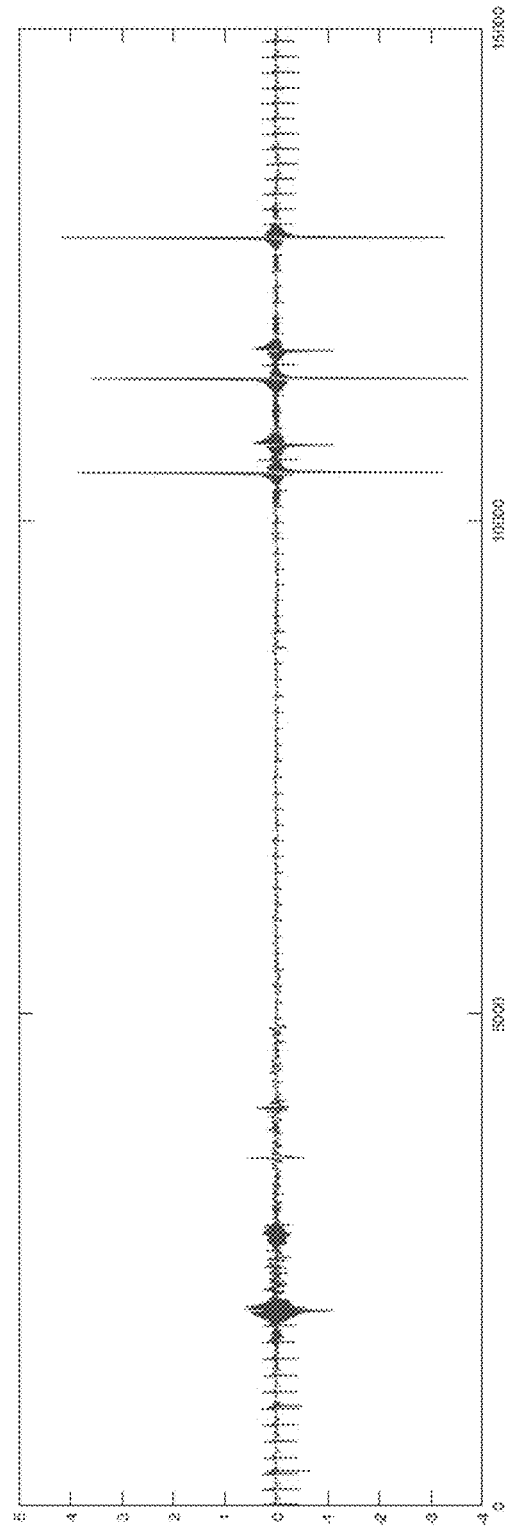
FIG. 18F shows an exemplary filtered data set based on the exemplary raw data set of FIG. 18E.
Figure 18G:
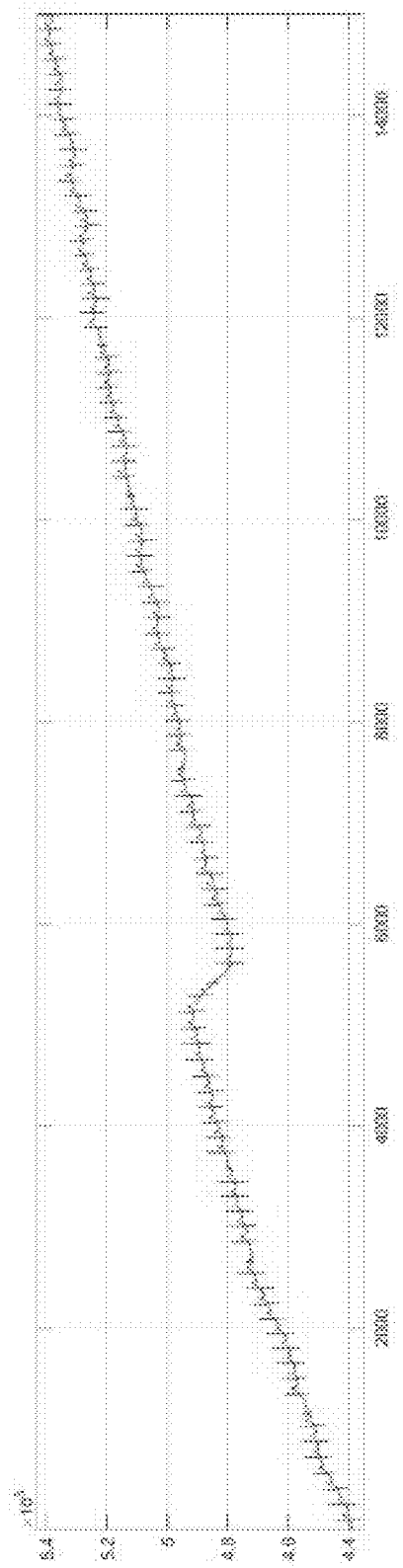
FIG. 18G shows an exemplary raw bio-potential data set.
Figure 18H:
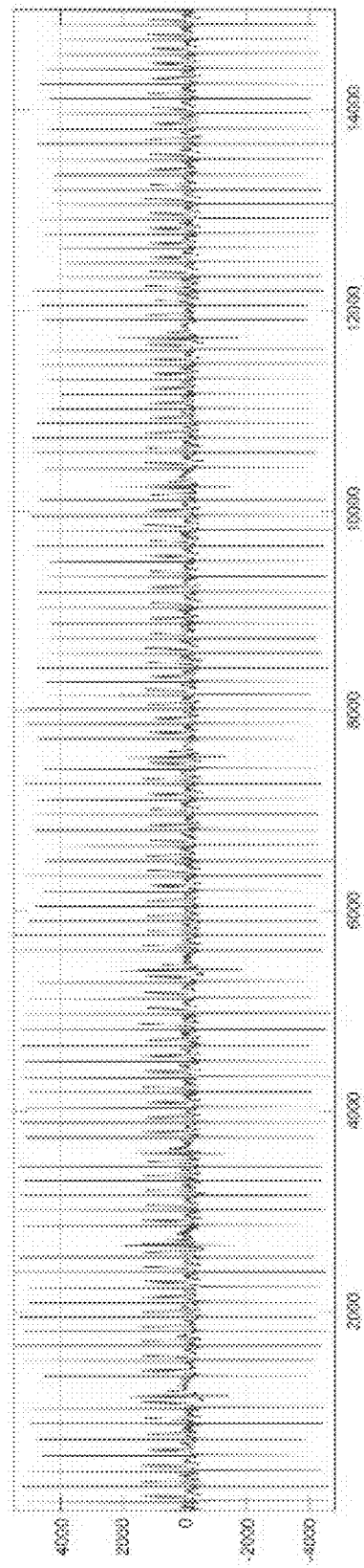
FIG. 18H shows an exemplary filtered data set based on the exemplary raw data set of FIG. 18G.

Continuing to refer to step 1310, in some embodiments, following application of the filters described above, each data channel is checked for contact issues. In some embodiments, contact issues are identified in each data channel based on at least one of (a) RMS of the data channel, (b) signal-noise ratio ("SNR") of the data channel, and (c) time changes in peaks relative energy of the data channel. In some embodiments, a data channel is identified as corrupted if it has an RMS value greater than a threshold RMS value. In some embodiments, the threshold RMS value is two local voltage units (e.g., a value of about 16.5 millivolts). In some embodiments, the threshold RMS value is between one local voltage unit and three local voltage units. An exemplary data channel identified as corrupted on this basis is shown in FIGS. 18A and 18B. In some embodiments, a data channel is identified as corrupted if it has a SNR value less than a threshold SNR value. In some embodiments, the threshold SNR value is 50 dB. In some embodiments, the threshold SNR value is between 40 dB and 60 dB. In some embodiments, the threshold SNR value is between 30 dB and 70 dB. An exemplary data channel identified as corrupted on this basis is shown in FIGS. 18C and 18D. In some embodiments, a data channel is identified as corrupted if it has a change in relative R-wave peak energy from one interval to another that is greater than a threshold amount of change. In some embodiments, the threshold amount of change is 250%. In some embodiments, the threshold amount of change is between 200% and 300%. In some embodiments, the threshold amount of change is between 150% and 350%. An exemplary data channel identified as corrupted on this basis is shown in FIGS. 18E and 18F. An exemplary data channel not identified as corrupted for any of the above reasons is shown in FIGS. 18G and 18H.

Figure 19A:
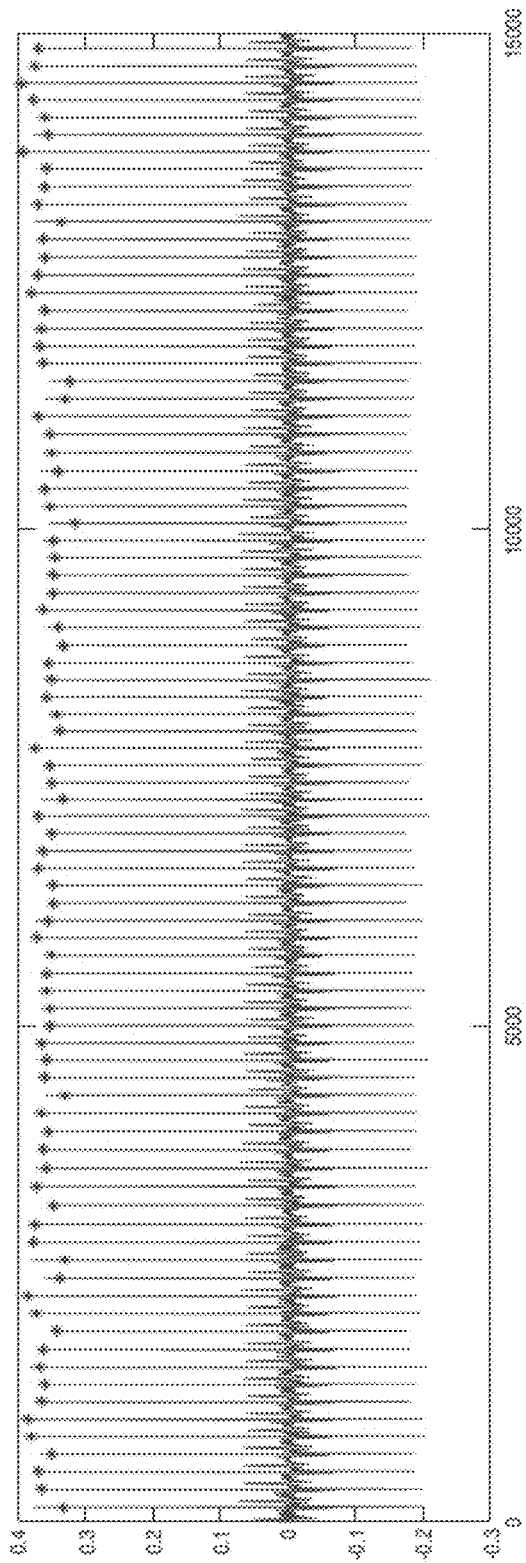
FIG. 19A shows an exemplary filtered data set with input peak positions.
Figure 19B:
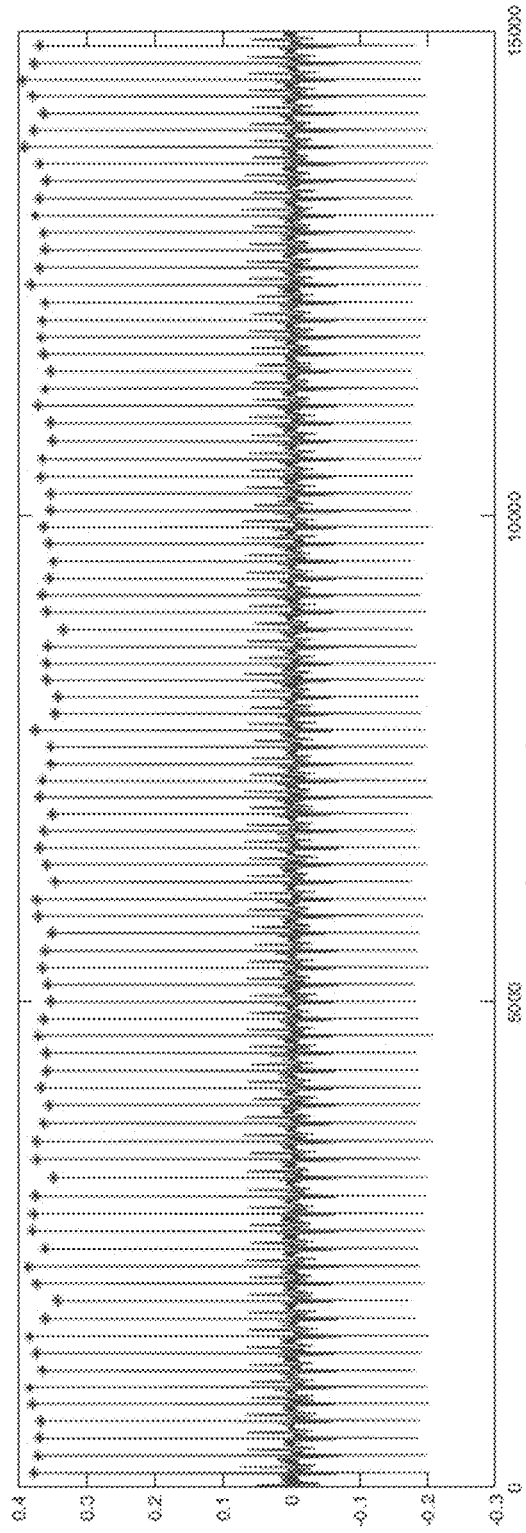
FIG. 19B shows the exemplary filtered data set of FIG. 19A with extracted peak positions.

In step 1315, the exemplary inventive computing device is programmed/configured to extract R-wave peaks from the pre-processed signal channels to produce R-wave peak data sets. In some embodiments, step 1315 uses as input known maternal ECG peaks. In some embodiments, step 1315 uses as input maternal ECG peaks identified in accordance with the techniques described in U.S. Pat. No. 9,392,952. In some embodiments, step 1315 includes using the preprocessed data (e.g., as produced by step 1310) and the known maternal ECG peaks to refine the maternal ECG peak positions. In some embodiments, peak position refinement includes a search for the maximal absolute value in a window of samples before and after the known maternal ECG peaks to ensure the R-wave peak is positioned at the maximum point of the R waves for each one of the filtered signals. In some embodiments, the window includes plus or minus a predetermined length of time. In some embodiments, the predetermined length is between 50 milliseconds and 350 milliseconds. In some embodiments, the predetermined length is between 100 milliseconds and 300 milliseconds. In some embodiments, the predetermined length is between 150 milliseconds and 250 milliseconds. In some embodiments, the predetermined length is between 175 milliseconds and 225 milliseconds. In some embodiments, the predetermined length is about 200 milliseconds. In some embodiments, the window includes plus or minus a number of samples that is in a range between one sample and 100 samples. Illustration of the known maternal ECG peaks and the extracted R-wave peaks in an exemplary R-wave peak data set are shown in FIGS. 19A and 19B, respectively.

Figure 20A:
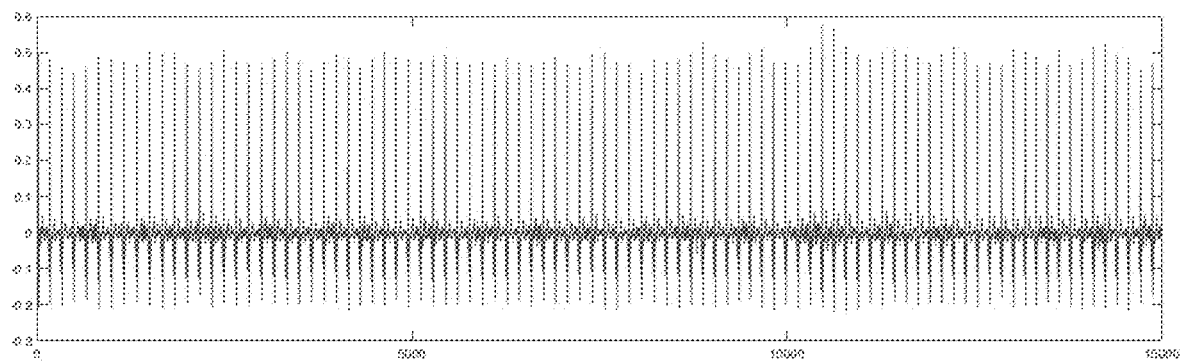
FIG. 20A shows an exemplary filtered data set.

In step 1320, the exemplary inventive computing device is programmed/configured to remove electromyography ("EMG") artifacts from the data, which includes the preprocessed data produced by step 1310 and the R-wave peaks extracted in FIG. 1315. FIG. 20A shows exemplary preprocessed data used as input to step 1320. In some embodiments, removal of EMG artifacts is performed in order to correct for peaks with high amplitude where there is an increase in high frequency energy, which usually, but not always, originates from maternal EMG activity. Other sources of such energy are high powerline noise and high fetal activity. In some embodiments, removal of EMG artifacts includes finding corrupted peaks and replacing them with a median value. In some embodiments, finding corrupted peaks includes calculating inter-peak RMS values based on the following formula:

The first step of correcting this artefact is finding the corrupted peaks. Doing so requires calculating the inter-peaks RMS values thus:

$$\text{inter peaks RMS}(i\text{Peak}) = \text{RMS}(\text{peaks signal}(\text{peak location}(i\text{Peak})+1 : \text{peak location}(i\text{Peak}+1)-1))$$

In the above formula, peaks signal is the signal with R-peaks heights (i.e., the amplitude of the R-wave peaks) and peak location is the signal with R-peaks time-indices found per each channel (i.e., the time index for each of the R-wave peaks). In some embodiments, there are two peaks signal values and two peak location values, one for R-wave peaks found using the filtered data and one found using the opposite signal (i.e., a signal obtained by multiplying the original signal data by −1 to yield a sign-inverted signal).

In some embodiments, finding corrupted peaks also includes finding outlier peaks in a maternal physical activity ("MPA") data set. In some embodiments, such signals (referred to as "envelope signals" hereinafter) are extracted as follows:

In some embodiments, physical activity data is collected using motion sensors. In some embodiments, the motion sensors include a tri-axial accelerometer and a tri-axial gyroscope. In some embodiments, the motion sensors are sampled 50 times per second (50 sps). In some embodiments, the sensors are located on a same sensing device (e.g., a wearable device) that contains electrodes used to collect bio-potential data for the performance of the method 1300 as a whole (e.g., the garment 300 shown in FIG. 3).

In some embodiments, raw motion data is converted. In some embodiments, raw motion data is converted to g units in the case of accelerometer raw data and degrees per second in the case of gyroscope raw data. In some embodiments, the converted data is examined to distinguish between valid and invalid signals by determining whether the raw signals are saturated (e.g., that they have a constant maximal possible value). In some embodiments, signal envelope is extracted as follows. First, in some embodiments, the data is checked for position change. Since position change is characterized by an increase in accelerometer baseline, in some embodiments a baseline filter is applied whenever a position change occurs. In some embodiments, filtration is performed by employing a high-pass finite impulse response ("FIR") filter. In some embodiments, the high-pass filter has a filter order of 400 and a frequency of 1 Hertz. In some embodiments, to eliminate any non-physiological movement, a low-pass FIR filter is also applied. In some embodiments, the low-pass filter has a filter order of 400 and a frequency of 12 Hertz. (order 400, fc=12 Hz [1]) is applied as well. In some embodiments, following filtering, the magnitude of the accelerometer vector is calculated in accordance with the below formula:

$$AccMagnitudeVector(iSample) = \sqrt{(AccData(x, iSample)^2 + AccData(y, iSample)^2) + AccData(z, iSample)^2}$$

In this formula, AccMagnitudeVector(iSample) represents the square root of the sum of the squares of the three accelerometer axes (e.g., x, y, and z) for sample number iSample. In some embodiments, the magnitude vector of the gyroscope data is calculated in accordance with the following formula:

$$GyroMagnitudeVector(iSample) = \sqrt{(GyroData(x, iSample)^2 + GyroData(y, iSample)^2 + GyroData(z, iSample)^2)}$$

In this formula, GyroMagnitudeVector(iSample) represents the square root of the sum of the squares of the three gyroscope axes (e.g., x, y, and z) for sample number iSample. In some embodiments, following calculation of both the accelerometer magnitude vector and the gyroscope magnitude vector, envelopes of the gyroscope's magnitude vector and the accelerometer's magnitude vector are extracted by applying an RMS window to the gyroscope's magnitude vector and the accelerometer's magnitude vector, respectively. In some embodiments, the RMS window is 50 samples in length. In some embodiments, following extraction of the envelopes of the gyroscope's magnitude vector and the accelerometer's magnitude vector, the two envelopes are averaged (e.g., mean average, median, etc.) to produce an MPA motion envelope.

Figure 20B:
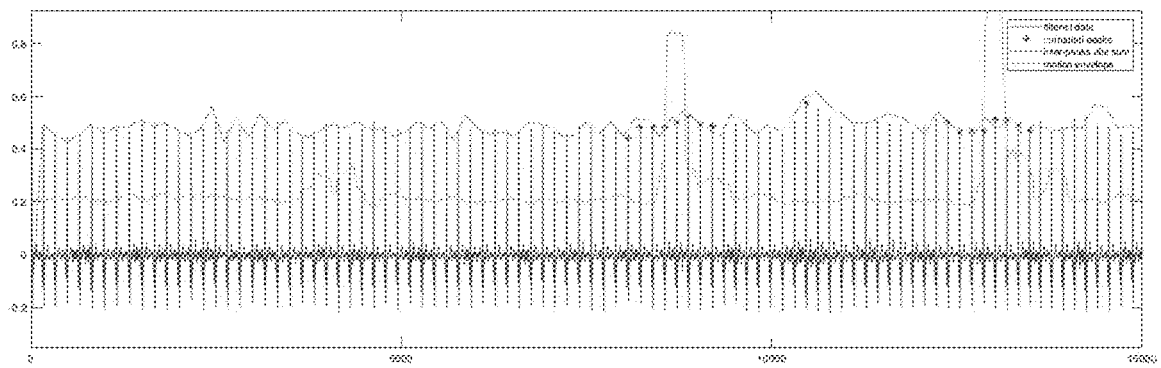
FIG. 20B shows the exemplary filtered data set of FIG. 20A with representations of a corresponding maternal motion envelope and an inter-peaks absolute sum.

In some embodiments, peaks in the MPA motion envelope are defined in accordance with the following steps:

motion envelope peaks=find(motion envelope>$P_{95\%}$ (motion envelope))

motion envelope peaks onset=motion envelope peaks−2·peak width motion envelope peaks offset=motion envelope peaks+2·peak width In the above, peak width is defined as the distance between the peak and the first point where the envelope reaches 50% of the peak value and $P_{95\%}(x)$ is the 95th percentile of x. FIG. 20B shows the data signal of FIG. 20A along with a corresponding motion envelope calculated in accordance with the above and an inter-peaks absolute sum (i.e., the sum of the absolute values of all samples falling in between adjacent peaks).

In some embodiments, peaks are determined to be corrupt if they are:

1) Peaks with inter-peaks RMS higher than 20 local voltage units
2) In case the signal examination stage concluded there is a contact issue in the current processing interval, peaks with inter-peaks RMS higher than 8 local voltage units
3) In case the signal examination stage concluded there is a contact issue in the current processing interval, but more than 50% of points have inter-peaks RMS higher than 8 local voltage units, use the 20 local voltage units threshold
4) Peaks positioned around the motion envelope onset and offset are suspected to be corrupt. These points' inter-peaks RMS should exceed 6 to conclude they are corrupt.

In some embodiments, if a peak is detected to be a corrupted peak as described above, the amplitude of the peak is replaced with a median value, where local median value around the corrupted peak is calculated as follows:

local median=median(peaks signal(corrupt peak−10: corrupt peak+10))

In some embodiments, the corrupted data points themselves are excluded from the above calculation and replaced with a statistical value (e.g., a global median, a local median, a mean, etc.). In some embodiments, if there are 7 or less values to use after exclusion, use the global median as the local one, where the global median is calculated using standard techniques:

local median=global median=median(signal)

Figure 20C:
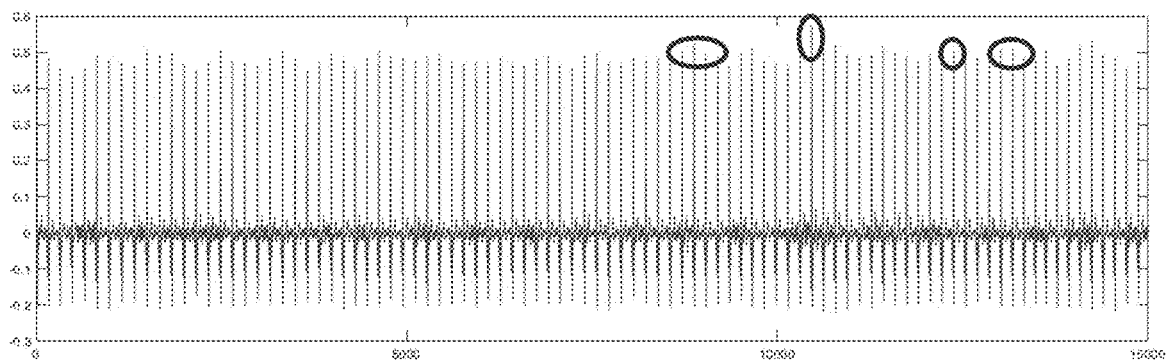
FIG. 20C shows an exemplary corrected data set produced by removal of electromyography artifacts from the filtered data set of FIG. 20A.

In some embodiments, if the absolute difference between the local median and global median exceeds 0.1, the local median is used in place of the amplitude of the corrupted data point, and otherwise the global median is used as a replacement for the corrupted peaks' amplitude. FIG. 20C shows the exemplary data set of FIGS. 20A and 20B with corrupted peaks replaced as discussed above.

Figure 21A:
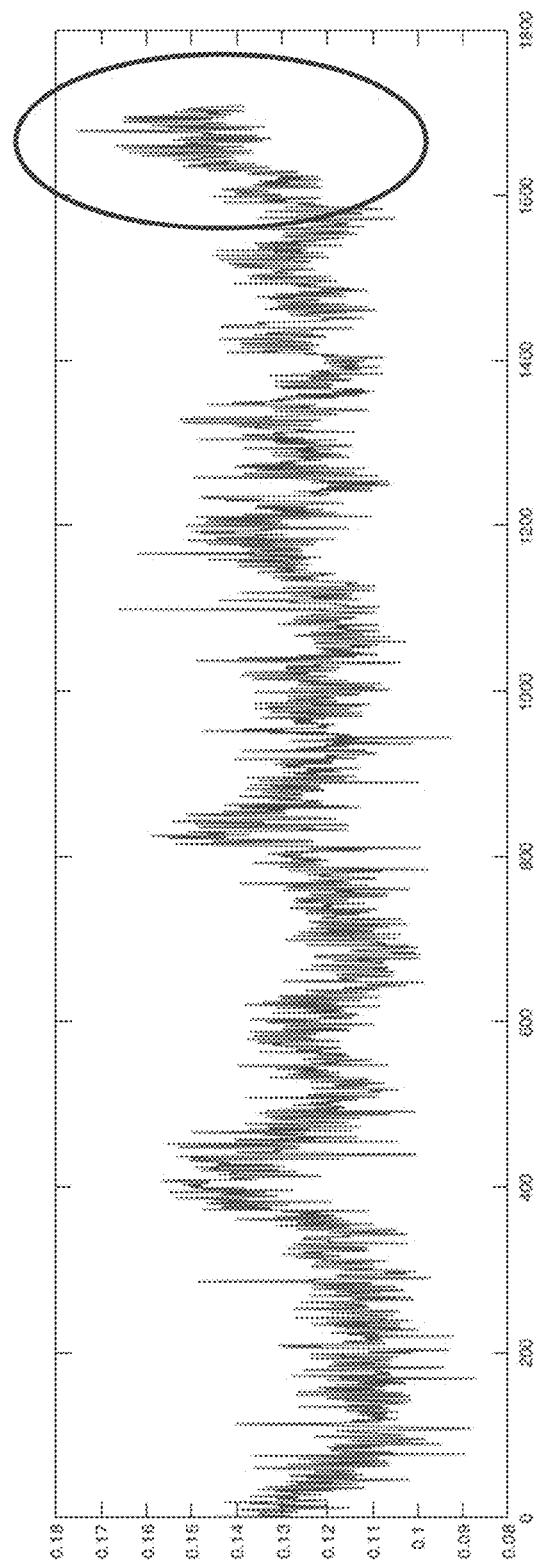
FIG. 21A shows an exemplary corrected data set including a baseline artifact.

Continuing to refer to FIG. 13, in step 1325, the exemplary inventive computing device is programmed/configured to remove baseline artifacts from the signal formed by the R-wave peaks. In some embodiments, such artifacts are caused by sudden baseline or RMS changes. In some embodiments, such changes are often caused by maternal position changes. FIG. 21A shows an exemplary data signal that includes a baseline artifact.

In some embodiments, such artifacts are found using the Grubbs test for outliers, which is a statistical test performed based on absolute deviation from sample mean. In some embodiments, to correct such artifacts, a point of change should be found at first. In some embodiments, a point of change is a point (e.g., data point) where a change in signal RMS or mean begins; such a point should satisfy the following criteria:

$$\text{length(peaks signal)} - \text{change point} > 50 \quad 1)$$

$$prctile(\text{peaks signal(change point:end)}, 10) > 0.01 \quad 2)$$

$$1.5 < \frac{P_{10\%}(\text{peaks signal}(1:\text{change point}-1))}{P_{10\%}(\text{peaks signal(change point:end)})} < \quad 3a)$$

$$2 \text{ (where } P_{10\%}(x) \text{ is the } 10^{th} \text{ percentile of } x)$$

OR $$0 < \frac{P_{10\%}(\text{peaks signal}(1:\text{change point}-1))}{P_{10\%}(\text{peaks signal(change point:end)})} < 0.08 \quad 3b)$$

In some embodiments, should the change point satisfy the above-mentioned criteria, the peak signal up to this point is changed based on a statistical value as defined below:

$$\text{peaks signal}(1:\text{change point}-1) =$$

$$\frac{P_{10\%}(\text{peaks signal(change point:end)})}{P_{10\%}(\text{peaks signal}(1:\text{change point}-1))} \cdot \text{peaks signal}(1:\text{change point}-1)$$

Figure 21B:
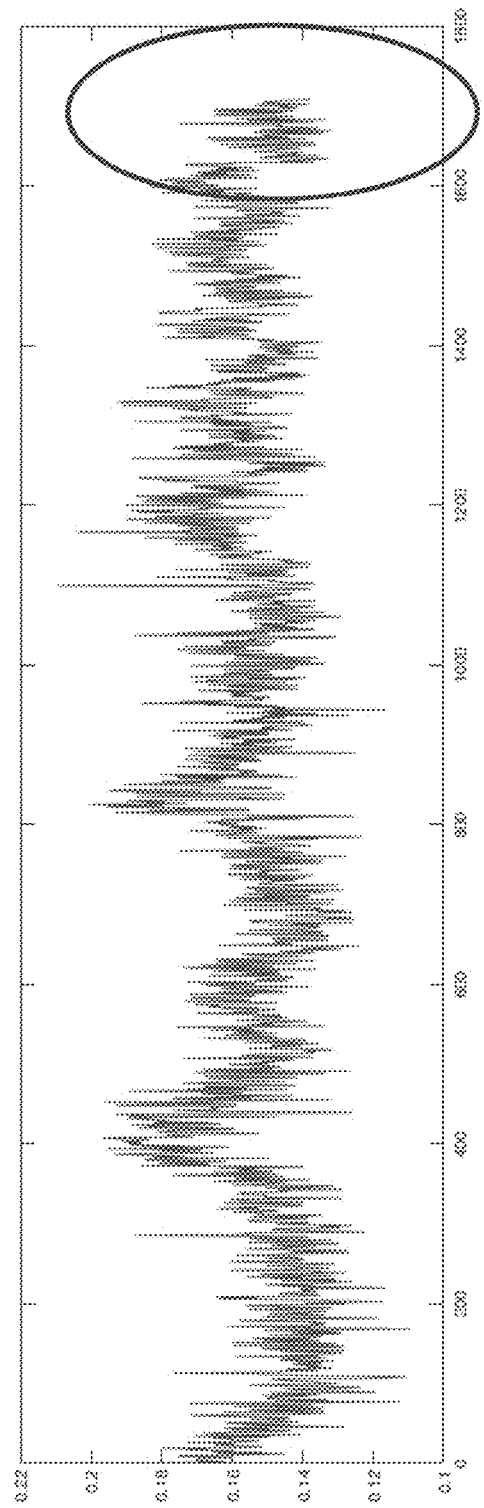
FIG. 21B shows the exemplary corrected data set of FIG. 21A following removal of the baseline artifact.

FIG. 21B shows the exemplary data signal of FIG. 21A after baseline artifact removal has been performed in accordance with step 1330.

Figure 22A:
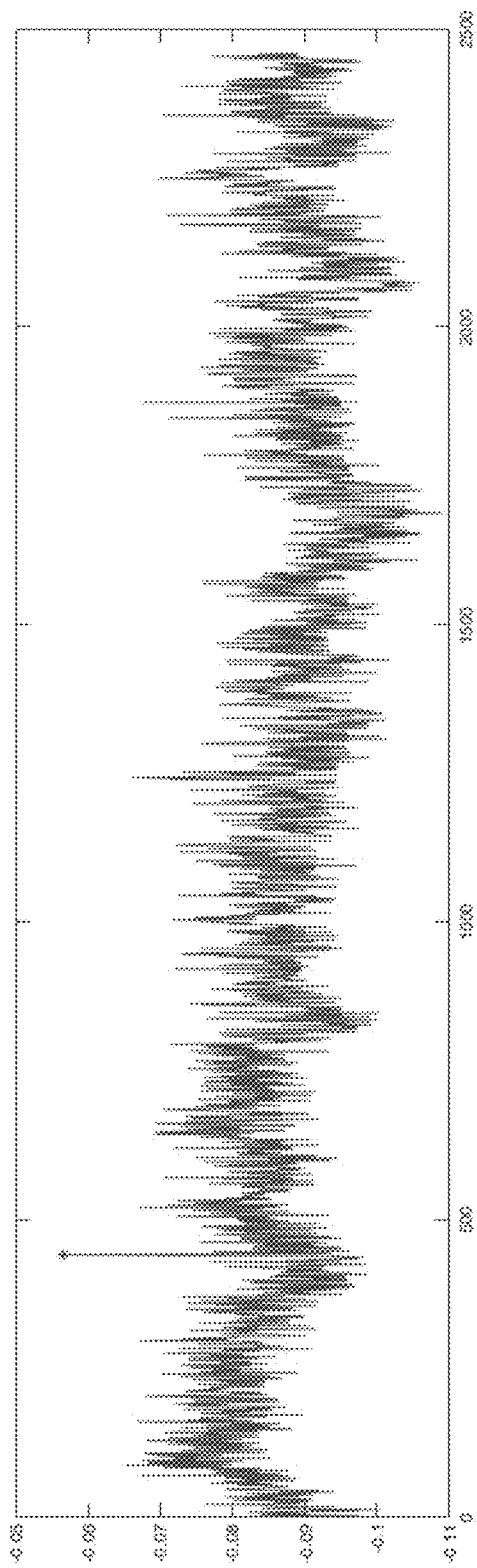
FIG. 22A shows an exemplary corrected data set including an outlier data point.

Continuing to refer to FIG. 13, in step 1330, the exemplary inventive computing device is programmed/configured to remove outliers from the R-wave peaks signal using an iterative process according to a Grubbs test for outliers. FIG. 22A shows an exemplary R-wave peaks signal that includes an outlier data point, as indicated by a diamond. In some embodiments, the iterative process of step 1330 stops when either of the following two conditions occurs:

$$\text{Outliers} \frac{P_{95\%}}{P_{50\%}} \text{ratio} > 1.5 \quad 1)$$

$$\text{Iteration number} > 4 \quad 2)$$

Figure 22B:
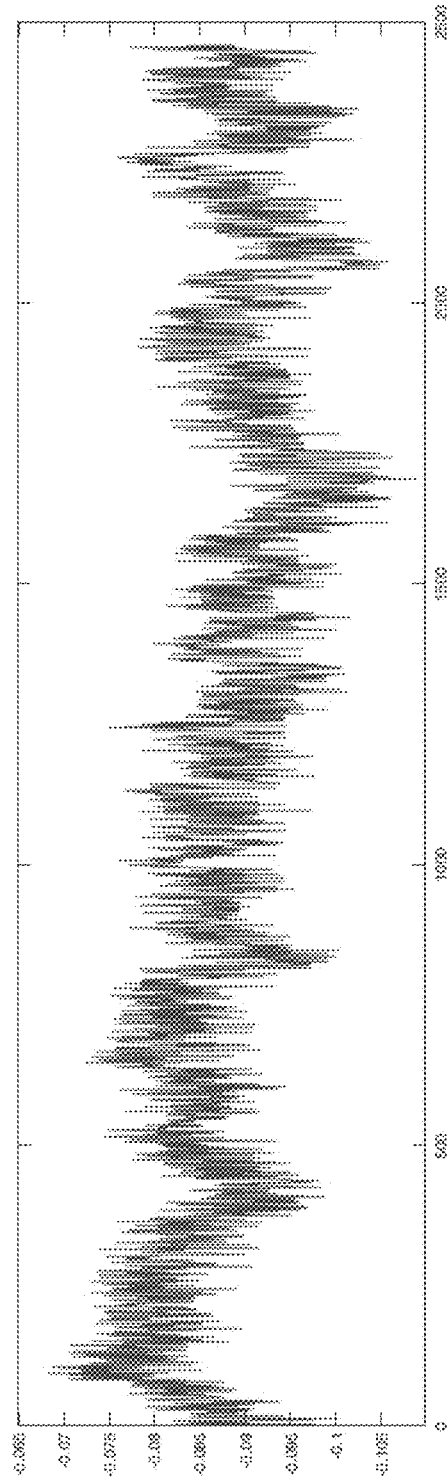
FIG. 22B shows the exemplary corrected data set of FIG. 22A following removal of the outlier data point.

In some embodiments, this process finds outlier points at each iteration and trims the height of such outlier points to the median value of the local area around the outlier peak. In some embodiments, the local area is defined as a time window of a predetermined number of samples before and after the outlier peak. In some embodiments, the predetermined number of samples is between zero and twenty. In some embodiments, the predetermined number of samples is ten. FIG. 22B shows the exemplary data signal of FIG. 22A following the performance of step 1330. It may be seen that the outlier data point shown in FIG. 22A is no longer present in FIG. 22B. In some embodiments, following signal extraction, more outliers are revealed and removed, as will be described in further detail hereinafter.

Figure 23A:
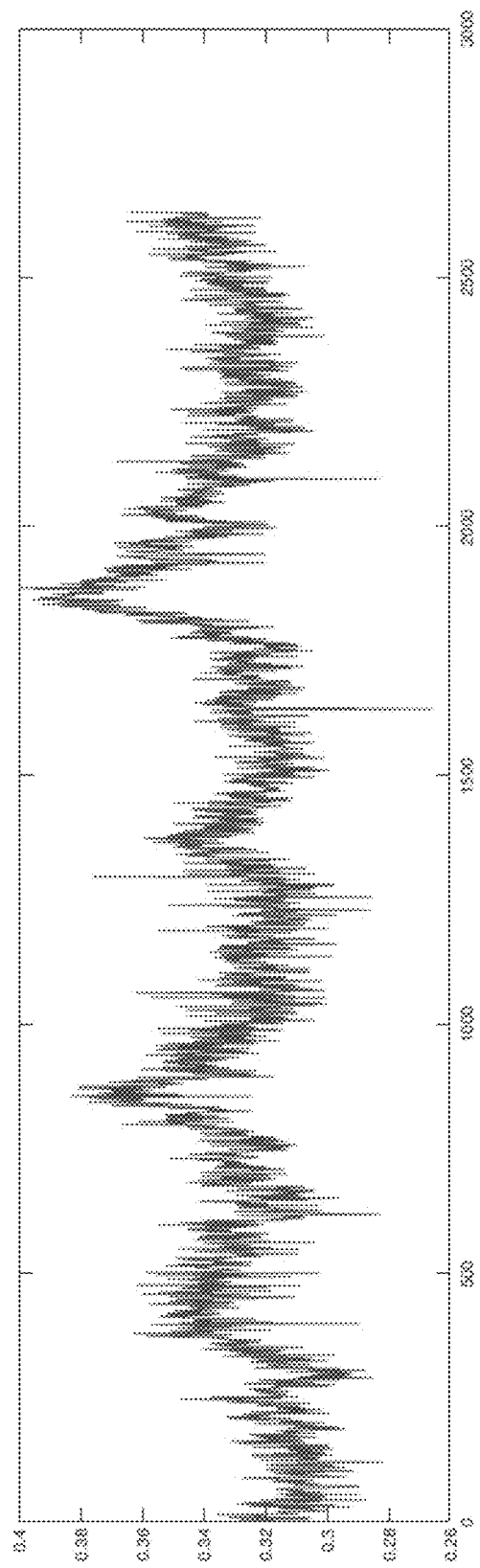
FIG. 23A shows an exemplary R-wave peaks signal.

Continuing to refer to FIG. 13, in step 1335, the exemplary inventive computing device is programmed/configured to interpolate and extract R-wave signal data from each of the R-wave peaks signal data sets to produce R-wave signal channels In some embodiments, the peaks signal that is output by step 1330 is interpolated in time to provide a 4 samples-per-second signal. FIG. 23A shows an exemplary peaks signal output by step 1330. In some embodiments, interpolation is done using cubic spline interpolation. In some embodiments in cases of large gaps in the interpolated data, erroneous high values are present, and instead the interpolation method is shape-preserving piecewise cubic interpolation. In some embodiments, the shape-preserving piecewise cubic interpolation is piecewise cubic hermite interpolating polynomial ("PCHIP") interpolation. In some embodiments, following interpolation, the process of extracting an R-wave signal includes identifying further outliers in the interpolated signal. In some embodiments, further outliers are identified in this step as one of the following:

1) Signal peaks (i.e., peaks in the R-wave signal after interpolation, not peaks in the raw bio-potential signal) with height larger than 1 local voltage unit and its surroundings
2) Points lying between two consecutive R-peaks that are more than 10 seconds apart
3) Minutes where a severe contact issue was found during the data examination stage (e.g., during steps 1320, 1335, and 1330)

In some embodiments, points that are identified as outliers based on meeting any of the three criteria mentioned above are discarded and are replaced by a statistical value (e.g., either a local median or a global median) in accordance with the process described above with reference to step 1320.

Figure 23B:
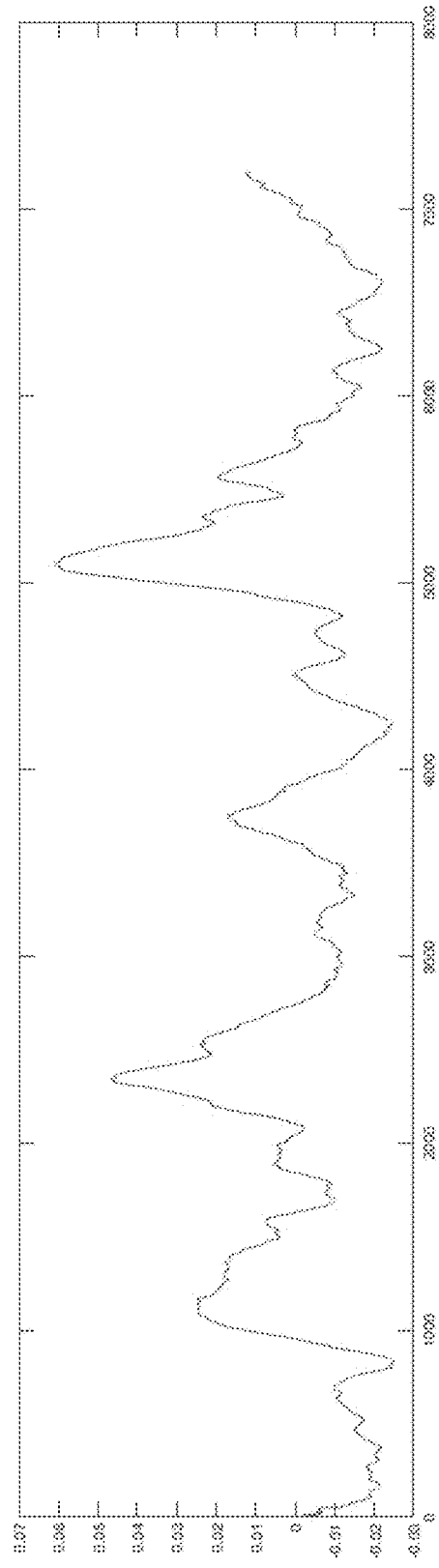
FIG. 23B shows an exemplary R-wave signal generated based on the exemplary R-wave peaks signal of FIG. 23A.

Continuing to describe step 1335, in some embodiments, following further outlier detection, signal statistics (e.g., median value, minimum value, and standard deviation) are calculated, and a signal (e.g., a one-minute signal time window for a given channel) is identified as a corrupted signal if any of the following are true:

1) After elimination of outlier points, the signal still has peaks with amplitude larger than one local voltage unit and standard deviation greater than 0.1
2) The signal has a median value greater than 0.65 and a minimum less than 0.6
3) More than 15% of the points comprising the signal have been deleted as outliers Continuing to describe step 1335, following identification of corrupt signals, a sliding RMS window is applied to the signal. In some embodiments, the RMS window has a size that is in the range of between 25 and 200 samples. In some embodiments, the RMS window has a size of 100 samples. In some embodiments, following application of an RMS window, a first order polynomial function is fitted to the signal and then subtracted from the signal, thereby producing a clean version of the interpolated signal, which may be used for the subsequent steps. FIG. 23B shows an exemplary R-wave signal following interpolation of step 1330.

Continuing to refer to FIG. 13, in step 1340, the exemplary inventive computing device is programmed/configured to perform channel selection, whereby a subset of the exemplary R-wave signal channels is selected for use in generating an electrical uterine monitoring signal. In some embodiments, at the start of channel selection all channels are considered to be eligible candidates, and channels are evaluated for possible exclusion in accordance with the following:

1) Exclude any channels with contact issues in more than 10% of the processing intervals up to the present time
2) If more than 50% of channels are excluded on the basis of the above, exclude instead all channels with contact issues in more than 15% of the processing intervals If the above results in all channels being excluded, then, instead, any channels that satisfy both of the following criteria are retained, with the remaining channels excluded:

1) Standard deviation of the signal is between 0 and 0.1
2) Range of the signal is less than 0.2

Figure 24A:
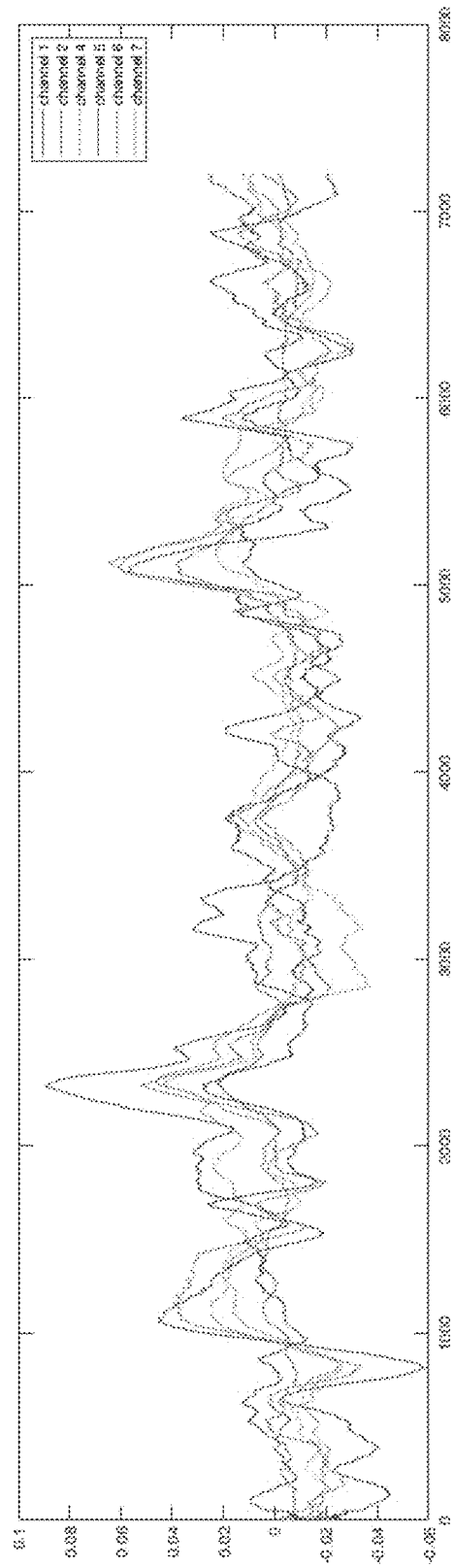
FIG. 24A shows an exemplary set of candidate R-wave signal channels.

If the above still results in all channels being excluded, then only the first above condition relating to standard deviation is used, and the second above condition relating to range is disregarded. FIG. 24A shows an exemplary data set including six data channels, with two data channels having been excluded.

In some embodiments, following removal of some channels as described above, the remaining channels are grouped into couples. In some embodiments, in which channels are defined as described above, a channel couple is any pair of the eight channels discussed above. In some embodiments, only couples that are independent of one another (i.e., couples that have no electrode in common) are considered. In some embodiments, possible couples are as follows:

1. channels 1 and 2 (A1-A4 and A2-A3)
2. channels 1 and 5 (A1-A4 and B1-B3)
3. channels 1 and 6 (A1-A4 and B1-B2)
4. channels 1 and 7 (A1-A4 and B3-B2)
5. channels 2 and 5 (A2-A3 and B1-B3)
6. channels 2 and 6 (A2-A3 and B1-B2)
7. channels 2 and 7 (A2-A3 and B3-B2)
8. channels 3 and 5 (A2-A4 and B1-B3)
9. channels 3 and 6 (A2-A4 and B1-B2)
10. channels 3 and 7 (A2-A4 and B3-B2)
11. channels 3 and 8 (A2-A4 and A1-A3)
12. channels 4 and 5 (A4-A3 and B1-B3)
13. channels 4 and 6 (A4-A3 and B1-B2)
14. channels 4 and 7 (A4-A3 and B3-B2)
15. channels 5 and 8 (B1-B3 and A1-A3)
16. channels 6 and 8 (B1-B2 and A1-A3)
17. channels 7 and 8 (B3-B2 and A1-A3)

As may be seen, for each of the channel pairs listed above, the two channels forming the pair do not share a common electrode. In some embodiments, the Kendall rank correlation of each couple of channels is calculated using only valid points within the channels. In some embodiments, Kendall correlation counts the matching rank signs of each pair of signals to test their statistical dependency.

In some embodiments, channels are then selected by the following selection criteria. First, if the maximum Kendall correlation value is greater than or equal to 0.7, the selected channels are any independent channels having Kendall correlation values greater than or equal to 0.7. However, if all selected channels were previously identified as corrupted, then the output signal is identified as a corrupted signal. Additionally, if any of the selected channels was previously identified as corrupted, or if any of the selected channels has a range greater than 0.3, then any such channels are excluded from the selected channels.

Second, if none of the channels were selected under the first criterion noted above, then if the maximum Kendall correlation value is greater than or equal to 0.5 but less than 0.7, the selected channels are any independent channels having Kendall correlation values in this range. However, if all selected channels were previously identified as corrupted, then the output signal is identified as a corrupted signal. Additionally, if any of the selected channels was previously identified as corrupted, or if any of the selected channels has a range greater than 0.3, then any such channels are excluded from the selected channels.

Third, if none of the channels were selected under the first or second criteria noted above, then if the maximum Kendall correlation value is greater than zero but less than 0.5, then all channels having Kendall correlation values greater than zero are identified as selected channels. However, if the maximal correlation value is less than 0.3, then the output signal is marked as corrupted and all channels with range greater than 0.3 are excluded.

Fourth, if none of the channels were selected under the first three criteria noted above, then all channels with range greater than 0.3 and all channels with more than 15% deleted points are excluded, the remaining channels are selected, and this output signal is identified as one that should be less sharpened, as will be discussed hereinafter with reference to step 1355.

Figure 24B:
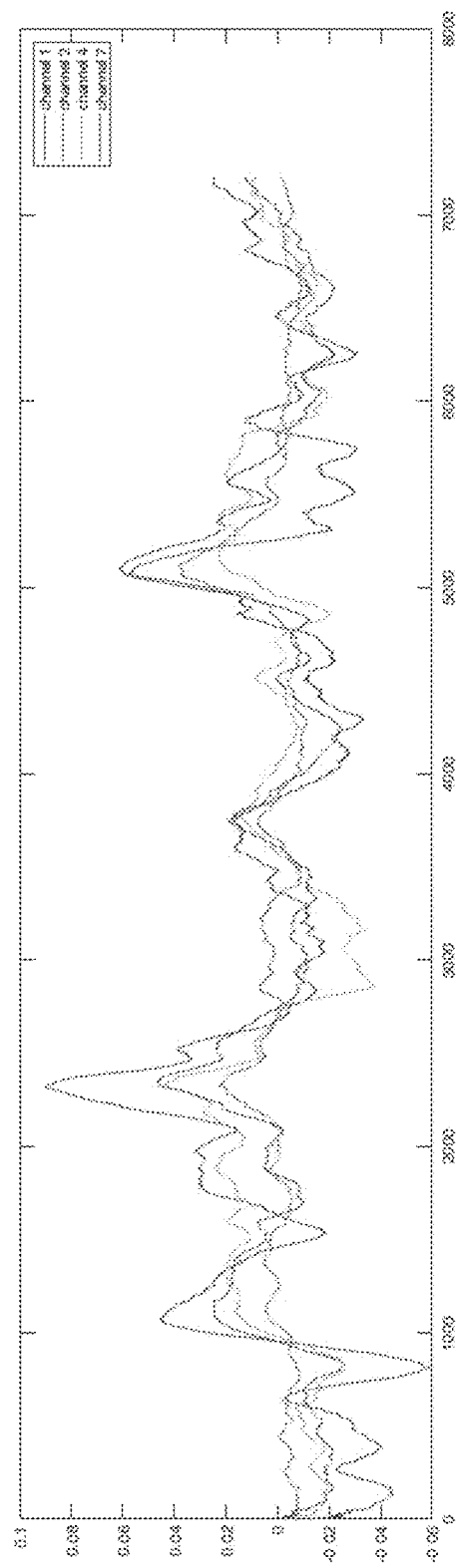
FIG. 24B shows an exemplary set of selected signal channels based on the exemplary set of candidate R-wave signal channels of FIG. 24A.

Fifth, if none of the channels were selected under any of the four criteria noted above, then all channels are selected other than those that have severe contact issues. However, if the number of contact issues in the selected channels exceeds fifteen, then the output signal is flagged as corrupted. FIG. 24B shows an exemplary data set following channel selection of step 1340.

In some embodiments, rather than selecting channels in pairs based on correlation values of the pairs, channels are selected individually.

Continuing to refer to FIG. 13, in step 1345, the exemplary inventive computing device is programmed/configured to calculate a uterine activity signal (which may be referred to as an "electrical uterine monitoring" or "EUM" signal) based on the selected R-wave signal channels selected in step 1340. In some embodiments, for each sample (e.g., set of data points at a given sampling time during the four samples per second sampling interval discussed above, for all selected channels), the $80^{th}$ percentile of the selected channels' signals is calculated in accordance with the following:

$$\text{combined signal}(i\text{Sample}) = P_{80\%}(\text{interpolated peaks signal}(\text{selected channels}, i\text{Sample}))$$

Figure 25A:
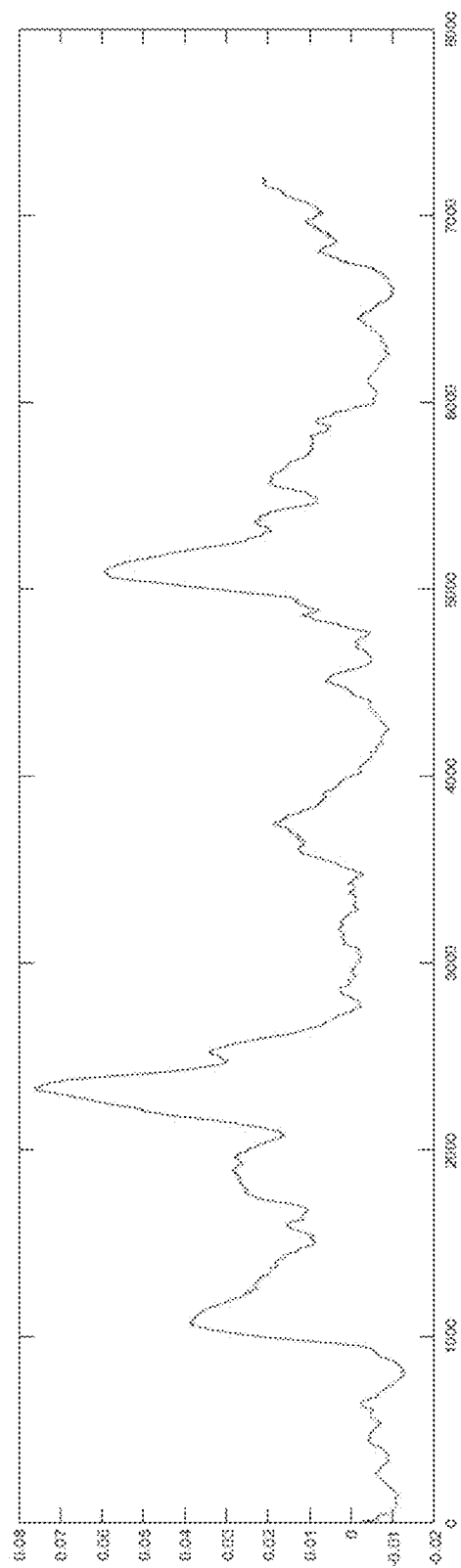
FIG. 25A shows an exemplary electrical uterine monitoring signal generated based on the set of selected signal channels shown in FIG. 24B.
Figure 25B:
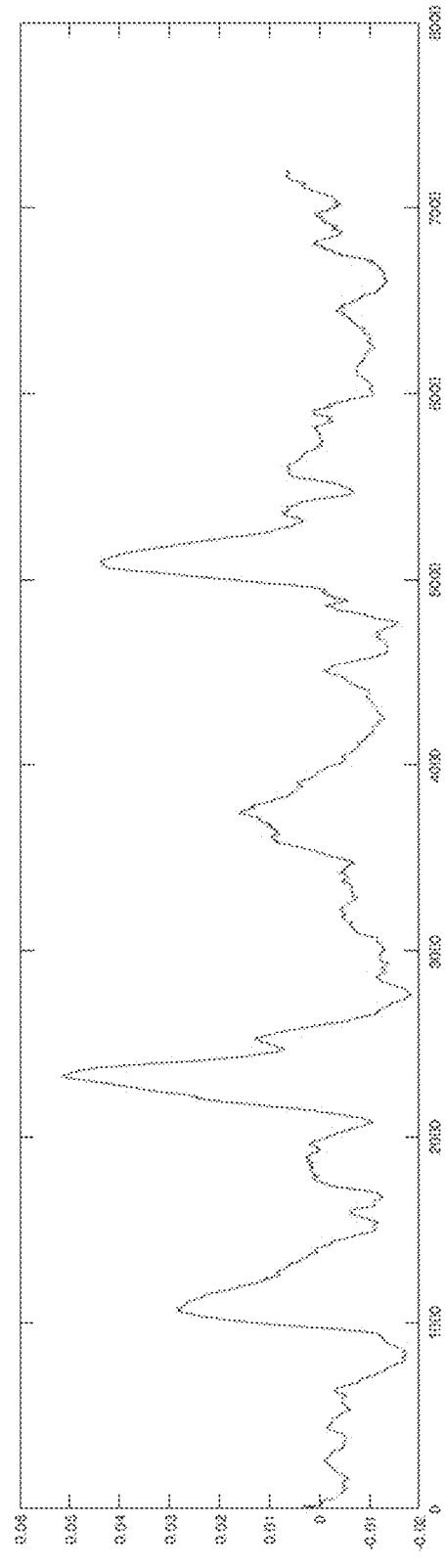
FIG. 25B shows an exemplary corrected electrical uterine monitoring signal generated by applying wandering baseline removal to the exemplary electrical uterine monitoring signal of FIG. 25A.

FIG. 25A shows an $80^{th}$ percentile signal calculated based on the selected data channels shown in FIG. 24B. In some embodiments, a wandering baseline is then removed from the combined $80^{th}$ percentile signal as determined above to produce an EUM signal. In some embodiments, a moving average window is considered to find the baseline. In some embodiments, the moving average window subtracts the mean value during the window from the EUM signal. In some embodiments, the length of the window is between zero minutes and twenty minutes. In some embodiments, the length of the window is ten minutes. FIG. 25B shows the exemplary signal of FIG. 25A following removal of the baseline.

Figure 26:
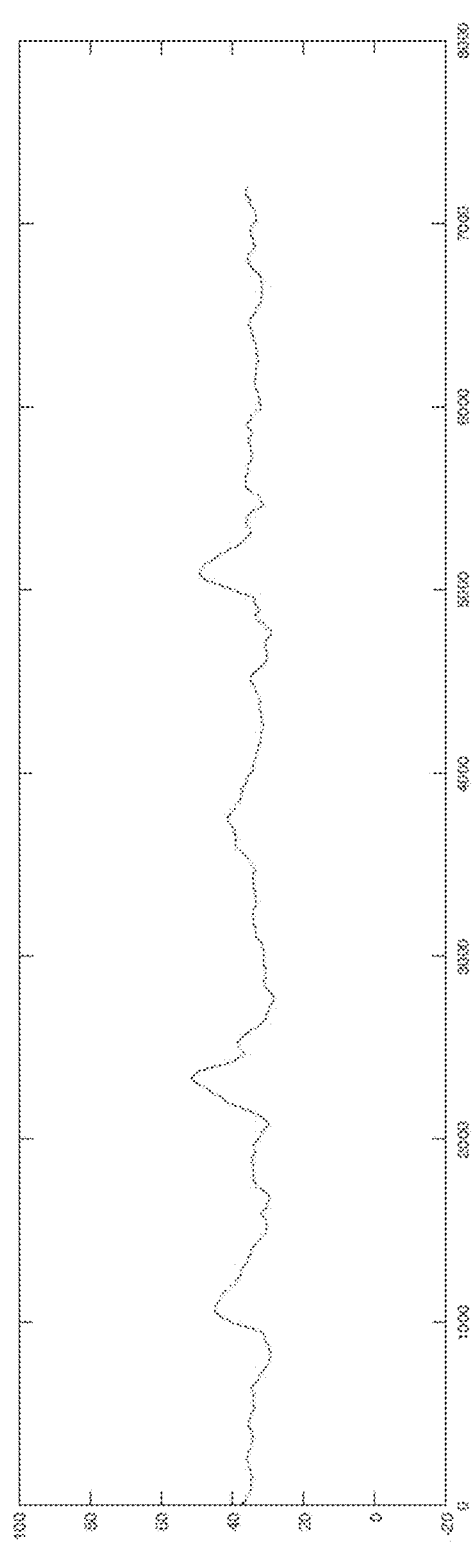
FIG. 26 shows an exemplary normalized electrical uterine monitoring signal generated based on the exemplary corrected electrical uterine monitoring signal of FIG. 25B.

In step 1350, the exemplary inventive computing system is programmed/configured to normalize the EUM signal calculated in step 1345. In some embodiments, normalization consists of multiplying the EUM signal from step 1345 by a constant. In some embodiments, the constant is between 200 and 500. In some embodiments, the constant is between 250 and 450. In some embodiments, the constant is between 300 and 400. In some embodiments, the constant is between 325 and 375. In some embodiments, the constant is about 350. In some embodiments, the constant is 350. In some embodiments, the constant is 1, i.e., the original values of the extracted $80^{th}$ percentile signal are maintained. FIG. 26 shows an exemplary data signal following normalization of the data signal of FIG. 25B in accordance with step 1350.

In step 1355, the exemplary inventive computing system is programmed/configured to sharpen the normalized EUM signal produced by step 1350, thereby producing a sharpened EUM signal. In some embodiments, sharpening is performed only on signals that were not flagged as corrupted in the preceding steps; if all relevant signals are flagged as corrupted, then the sharpening step is not performed. In some embodiments, the objective of the sharpening step is to enhance all areas with suspected contractions. In some embodiments, sharpening proceeds as follows. First, if there are any peaks in the EUM signal exceeding the values of 200 local voltage units, the signal is marked as corrupted. Second, it is determined whether the signal was previously marked as corrupted. Third, the signal baseline is removed. In some embodiments, for baseline removal, if the signal duration exceeds ten minutes then a ten-minute long moving average window is used to estimate the baseline, and otherwise the signal's $10^{th}$ percentile is used to estimate the baseline; in either case, the baseline is then subtracted from the EUM signal. Fourth, the signal baseline is defined as 30 visualization voltage units. In some embodiments, a signal baseline defined in this manner following the normalization step provides for an EUM signal that is within a 0-100 range in a manner similar to the signal provided by a cardiotocograph.

Fifth, peaks are identified in accordance with one of the following:

- If the signal was identified as one that needs less sharpening during step 1340, then peaks are defined as having a minimum height of 35 visualization voltage units and a minimum width of 300 samples.
- If the signal was not so identified, peaks are identified as having a minimum height of 35 visualization units and a minimum width of 220 samples.

In either case, the prominence of each peak is calculated in accordance with the below formula:

peaks prominence=peaks height–$P_{10\%}$(EUM signal)

Following the calculation of the prominence for all peaks in the sample, each peak is eliminated if either of the below is true for that peak:

- The peak has a prominence less than 12 and a height less than 40 visualization voltage units
- The peak has a prominence less than 65% of the maximum prominence of all of the peaks in the sample.

In some embodiments, additional peaks are identified by identifying any further peaks (e.g., local maxima) with a minimum height of 15 visualization voltage units and a minimum width of 200 samples, and then eliminating all peaks with a prominence higher than 20 visualization voltage units.

Following the above, sharpening is performed only if all of the following are true: (a) the signal is not corrupt (with "corrupt" signals being identified as described above); (b) there are no deleted points in the signal; and (c) at least one peak was identified in the preceding portions of this step. If sharpening is to be performed, then, prior to sharpening, each peak is eliminated if any of the below conditions are true for that peak:

- The peak has a prominence of less than 10 visualization voltage units
- The peak has a prominence of greater than 35 visualization voltage units
- The peak has a width of more than 800 samples (i.e., 200 seconds at 4 samples per second)

Following elimination of any peaks that meet one of the conditions noted above, the following values are calculated for each remaining peak:

$$\mu = \text{mean(peak start, peak end)}$$

$$\sigma = \frac{(\text{peak end} - \text{peak start})}{2\sqrt{2\pi}}$$

$$t = \text{peak start:peak end}$$

Once these values have been calculated, a mask of zero values outside the peak areas and Gaussian functions inside the peak areas is created in accordance with the following formula:

$$\text{mask}(t_{ith\ peak}) = \exp\left(-\frac{(t_{ith\ peak} - \mu_{ith\ peak})^2}{2\sigma_{ith\ peak}^2}\right)$$

Figure 27A:
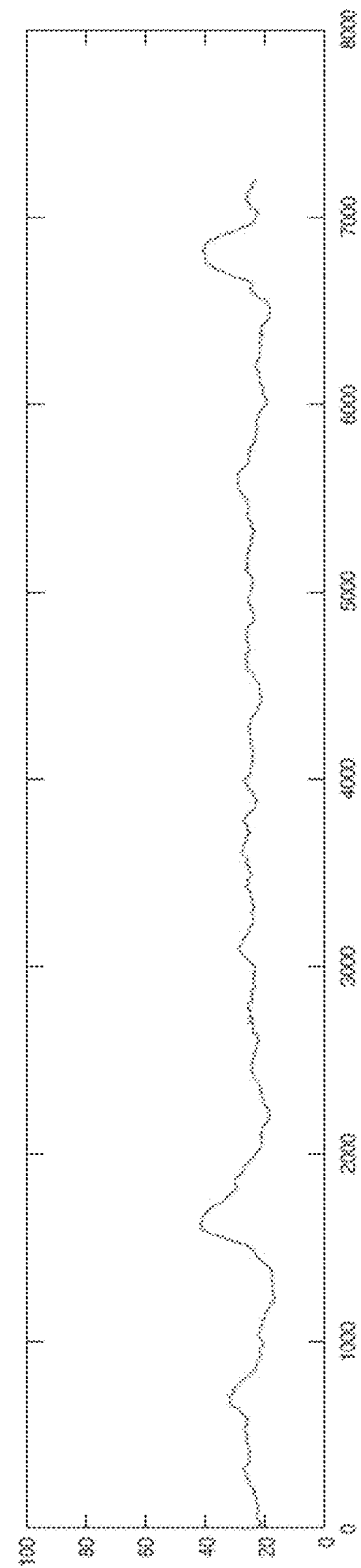
FIG. 27A shows an exemplary normalized electrical uterine monitoring signal.
Figure 27B:
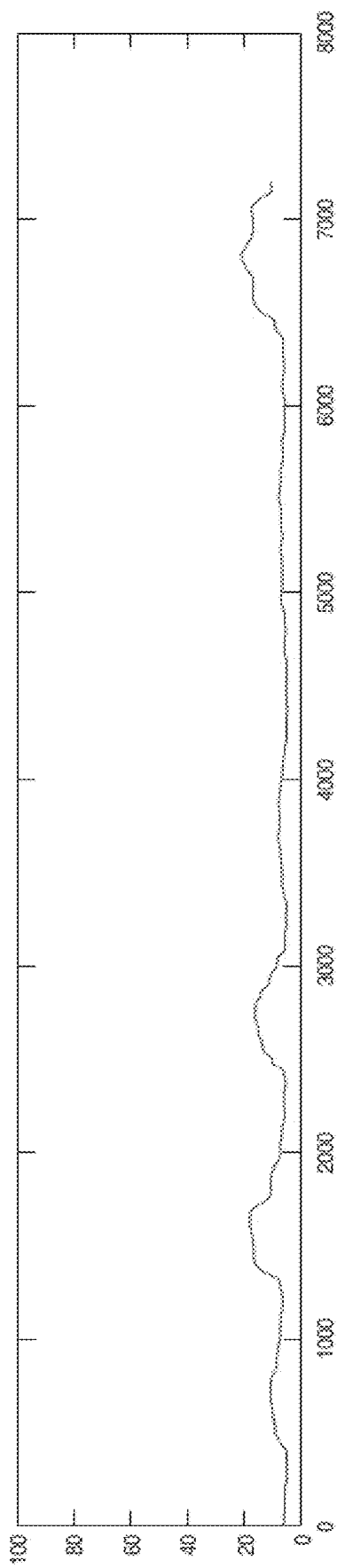
FIG. 27B shows an exemplary sharpening mask generated based on the exemplary normalized electrical uterine monitoring signal of FIG. 27A.
Figure 27C:
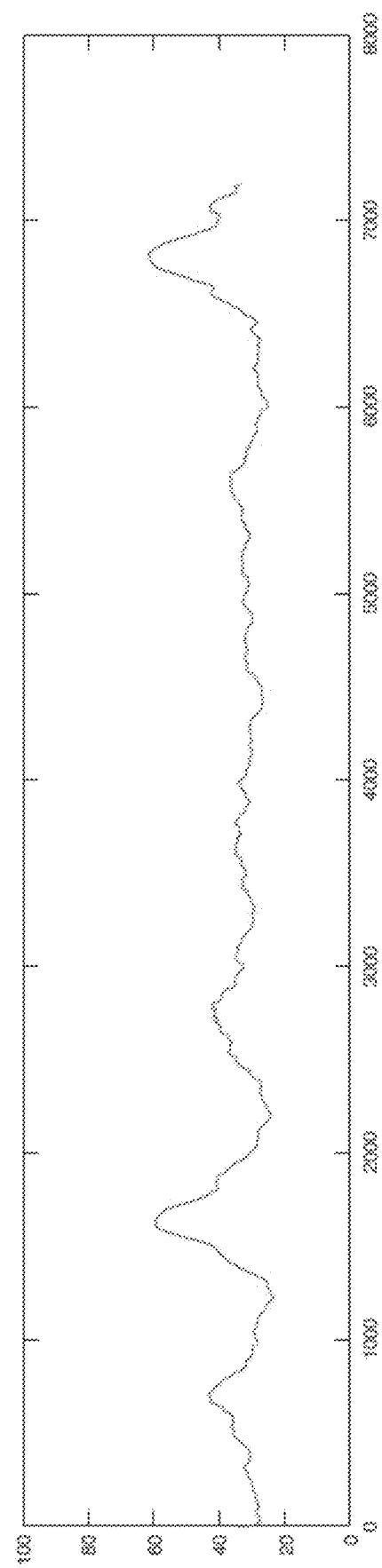
FIG. 27C shows an exemplary sharpened electrical uterine monitoring signal generated based on the exemplary normalized electrical uterine monitoring signal of FIG. 27A and the exemplary sharpening mask of FIG. 27B.

The mask is then smoothed with a moving average window having a predefined length. In some embodiments, the predefined length is between 10 seconds and 50 seconds. In some embodiments, the predefined length is between 20 seconds and 40 seconds. In some embodiments, the predefined length is between 25 seconds and 35 seconds. In some embodiments, the predefined length is about 30 seconds. In some embodiments, the predefined length is 30 seconds. An exemplary EUM signal is shown in FIG. 27A and an exemplary mask created in the above manner for the exemplary EUM signal of FIG. 27A is shown in FIG. 27B. The mask is then added to the existing EUM signal to produce a sharpened EUM signal. In some embodiments, the addition is performed using simple mathematical addition. An exemplary sharpened EUM signal produced by adding the exemplary mask of FIG. 27B to the exemplary EUM signal of FIG. 27A is shown in FIG. 27C.

Figure 28:
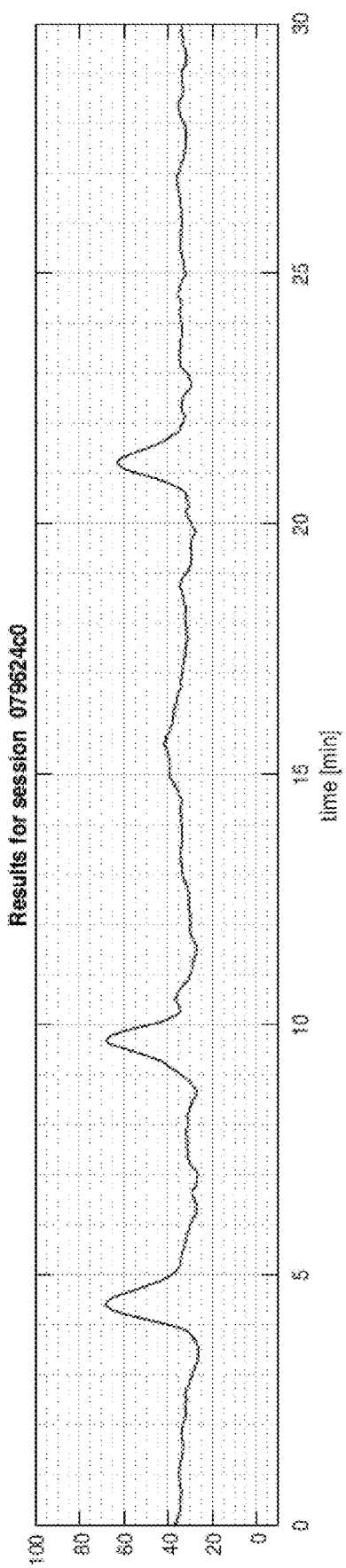
FIG. 28 shows an exemplary post-processed electrical uterine monitoring signal.

Referring back to FIG. 13, in step 1360, post-processing is performed to produce a post-processed EUM signal. In some embodiments, post-processing includes baseline removal. In some embodiments, baseline removal includes removing a signal baseline as described above with reference to step 1355. In some embodiments, for baseline removal, if the signal duration exceeds ten minutes then a ten-minute long moving average window is used to estimate the baseline, and otherwise the signal's 10th percentile is used to estimate the baseline; in either case, the baseline is then subtracted from the EUM signal, and the signal baseline is defined as 30 visualization voltage units. Last, all deleted values are set to a value of −1 visualization voltage unit and all values above 100 visualization voltage units are set to a value of 100 visualization voltage units. FIG. 28 shows an exemplary post-processed signal generated by applying the post-processing of step 1360 to the exemplary sharpened signal of FIG. 27B.

Figure 29:
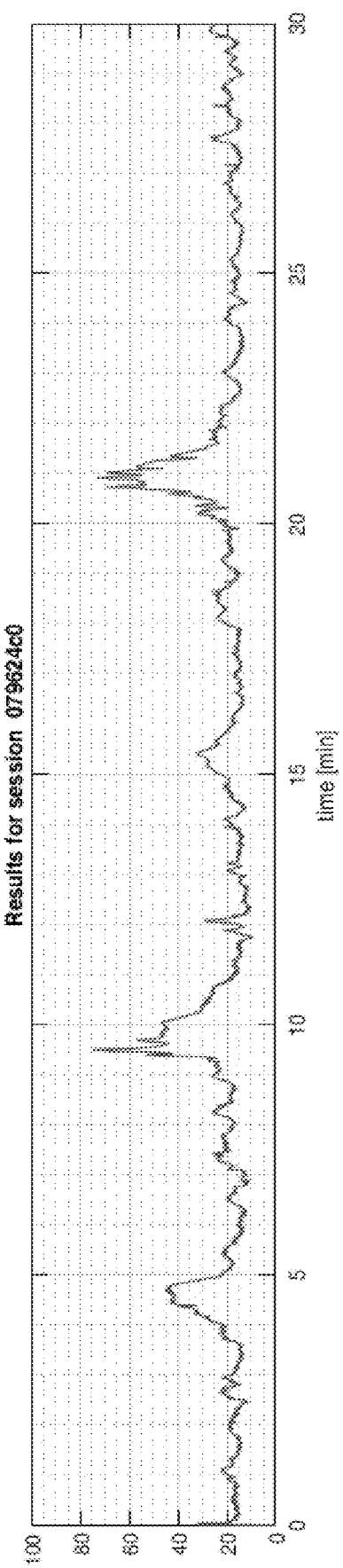
FIG. 29 shows a tocograph signal corresponding to the exemplary post-processed electrical uterine monitoring signal of FIG. 28.

Following step 1360, the method 1300 is complete. As noted above, FIG. 28 shows an exemplary EUM signal calculated in accordance with the method 1300. FIG. 29 shows a representative tocograph signal obtained in accordance with known techniques for the same subject and during the same time period as collection of the bio-potential data based on which the EUM signal of FIG. 28 was calculated. It may be seen that FIGS. 28 and 29 are substantially similar to one another and include the same peaks, which may be understood to represent contractions. Accordingly, it may be seen that the result of the method 1300 is an EUM signal that is usable as a tocograph-like signal to monitor maternal uterine activity, but which can be calculated based on bio-potential signals that are recorded non-invasively.

Reference is now made to the following examples, which together with the above descriptions illustrate some embodiments of the invention in a non-limiting fashion.

Examples

Figure 14A:
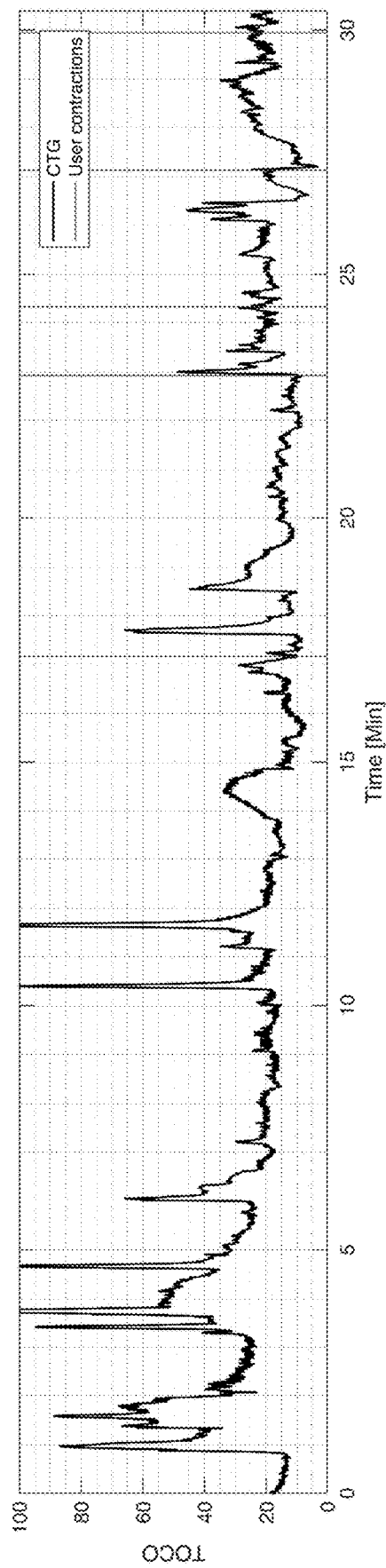
FIG. 14A shows a second tocograph signal with self-reported contractions annotated therein.
Figure 14B:
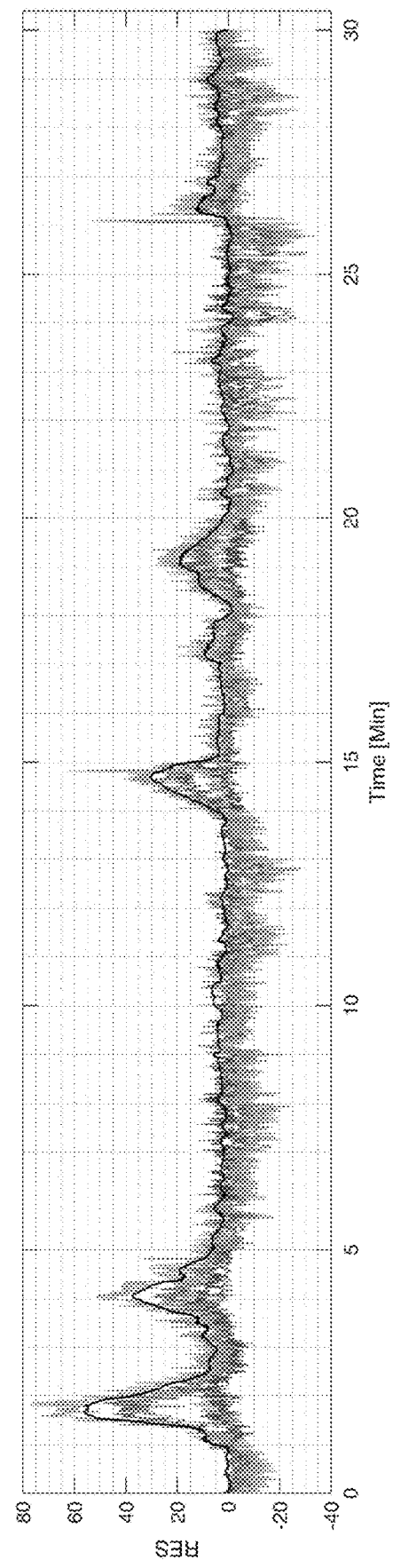
FIG. 14B shows a second exemplary electrical uterine signal derived from bio-potential data recorded during the same time period as that shown in FIG. 14A.
Figure 15A:
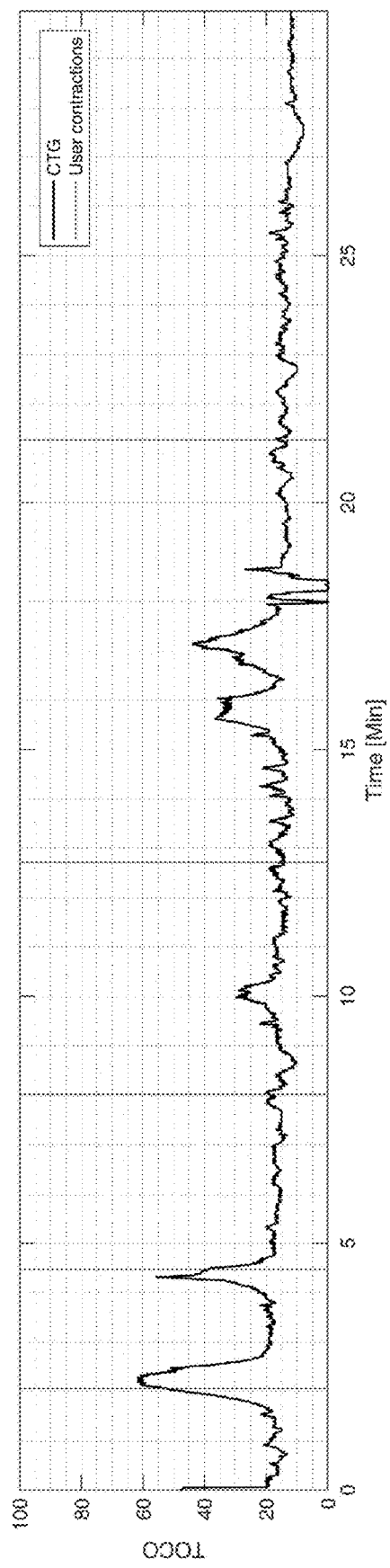
FIG. 15A shows a third tocograph signal with self-reported contractions annotated therein.
Figure 15B:
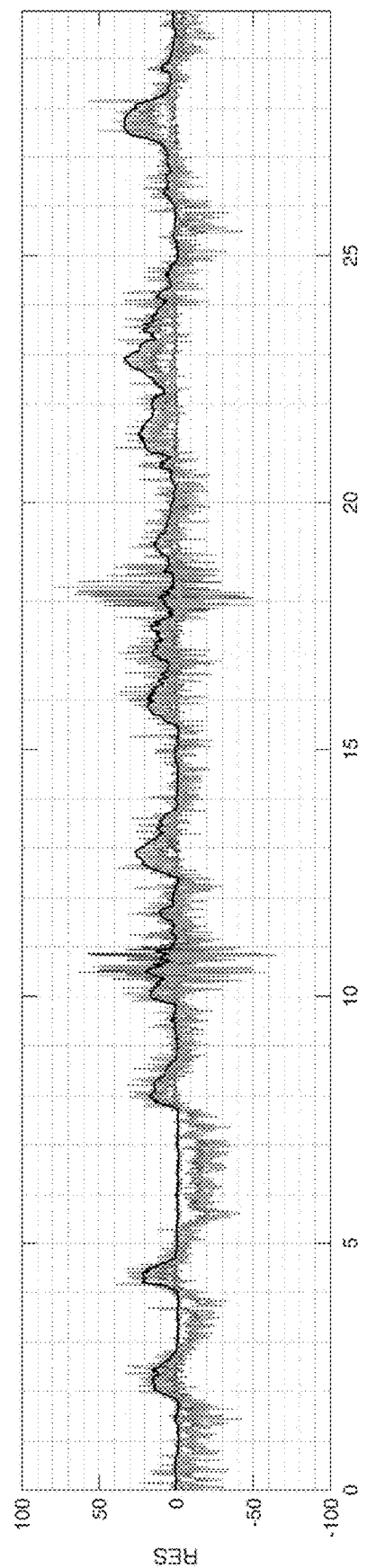
FIG. 15B shows a third exemplary electrical uterine signal derived from bio-potential data recorded during the same time period as that shown in FIG. 15A.
Figure 16A:
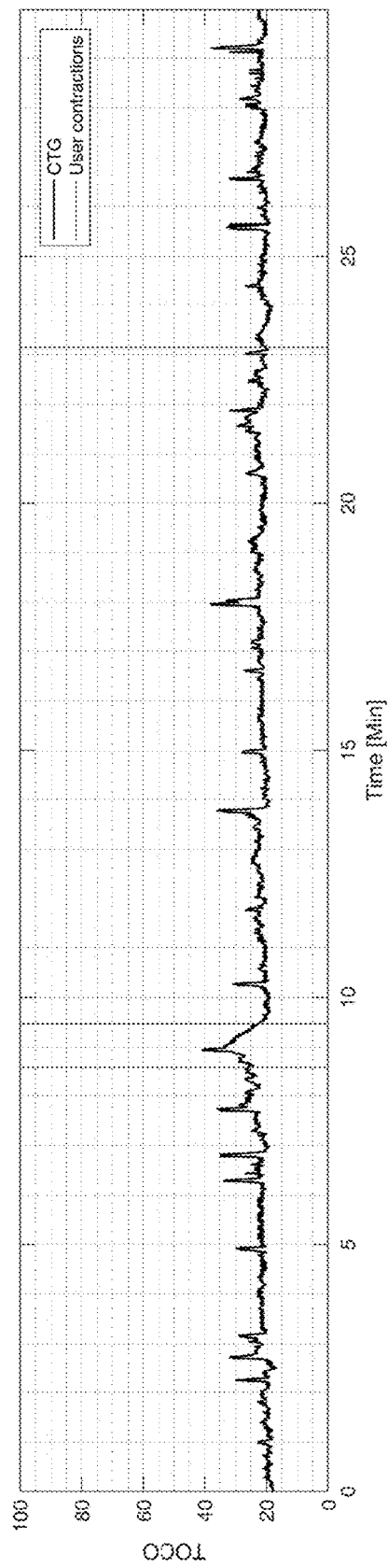
FIG. 16A shows a fourth tocograph signal with self-reported contractions annotated therein.
Figure 16B:
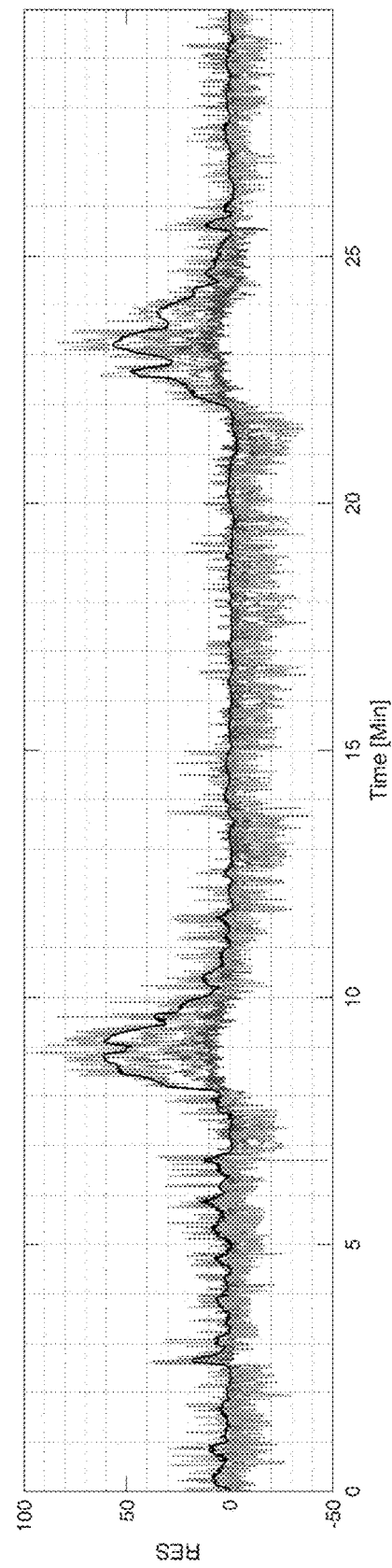
FIG. 16B shows a fourth exemplary electrical uterine signal derived from bio-potential data recorded during the same time period as that shown in FIG. 16A.
Figure 17A:
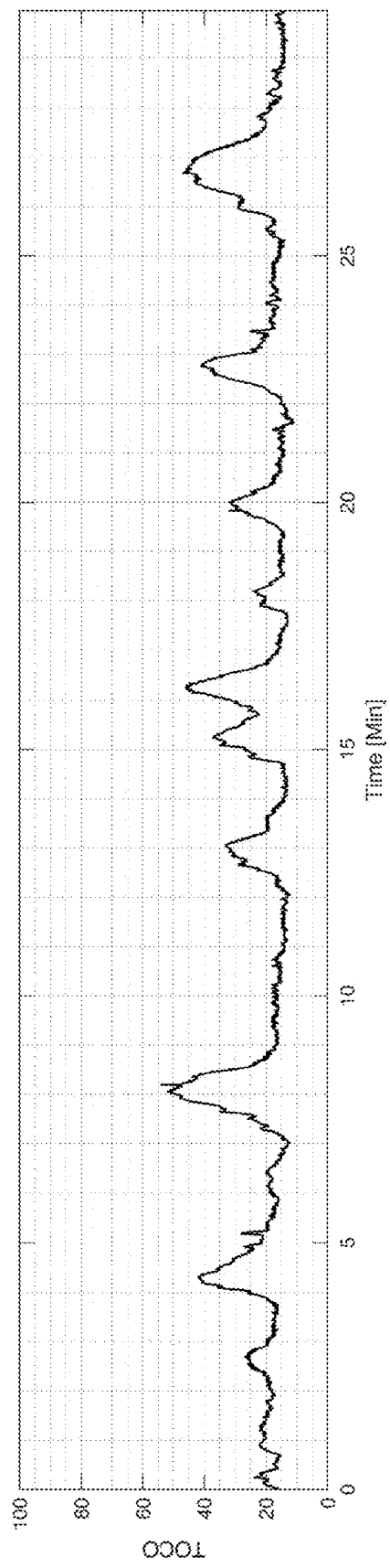
FIG. 17A shows a fifth tocograph signal with self-reported contractions annotated therein.
Figure 17B:
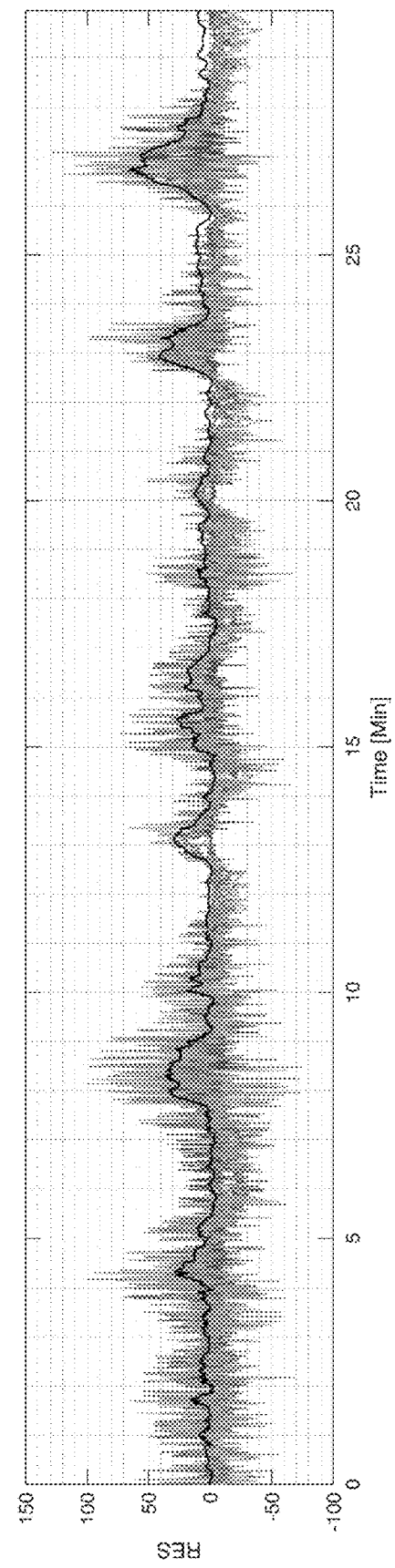
FIG. 17B shows a fifth exemplary electrical uterine signal derived from bio-potential data recorded during the same time period as that shown in FIG. 17A.

FIGS. 14A-17B show further examples of comparisons between tocograph data and the output of the exemplary method 200. In each of FIGS. 14A, 15A, 16A, and 17A, a tocograph signal against time is shown, with contractions self-reported by the mother being monitored by the tocograph indicated with vertical lines. In each of FIGS. 14B, 15B, 16B, and 17B, the filtered R-wave signal from each of a plurality of channels is shown in a different color (e.g., similar to the plot shown in FIG. 11B), with the calculated normalized average signal shown in a heavy black line (e.g., similar to the plot shown in FIG. 12A). Each of FIGS. 14B, 15B, 16B and 17B is shown adjacent to the corresponding one of FIGS. 14A, 15A, 16A, and 17A for comparison (e.g., FIGS. 14A and 14B show different data recorded for the same mother over the same time interval, and so on for FIGS. 15A through 17B). As discussed above with reference to FIGS. 12A and 12B, it can be seen that the peaks in the exemplary normalized uterine signal correspond to the self-reported contractions.

A study was conducted to evaluate the effectiveness of the exemplary embodiments. The study involved a comparison of EUM and TOCO recordings in pregnant women aged 18-50 years with a BMI of <45 kg/m², carrying a singleton fetus at gestational age >32+0 weeks, without fetal anomalies. EUM was calculated as described above over data samples measured for a minimum of 30 minutes. Analysis of the maternal cardiac R-wave amplitude-based uterine activity index referred to herein as EUM showed promising results as an innovative and reliable method for monitoring maternal uterine activity. The EUM data correlated highly with TOCO data. Accordingly, EUM monitoring may provide data that is similarly useful to TOCO data, while overcoming the shortcomings of traditional tocodynamometry, such as discomfort.

FIGS. 18A through 27B show exemplary data existing at various stages during performance of the exemplary method 1300. In particular, FIGS. 27A and 27B show a comparison of the output signal generated by the exemplary method 1300 to a tocograph signal recorded during the same time interval.

FIGS. 18A-18H show exemplary raw data that is received as input for the exemplary method 1300 (e.g., as received in step 1305) and exemplary filtered raw data produced during the exemplary method 1300 (e.g., as produced by step 1310). In particular, FIGS. 18A, 18C, 18E, and 18G show exemplary raw data, while FIGS. 18B, 18D, 18F, and 18H respectively, show exemplary filtered data. It will be apparent to those of skill in the art that FIGS. 18A-18H represent raw and filtered bio-potential data for a single channel and that, in a practical implementation of the method 1300 as described above, data sets comparable to those shown in FIGS. 18A-18H will be present for each channel of data. Referring to FIG. 18A, it may be seen that there is high powerline noise around sample number 6000. Referring to FIG. 18B, it may be seen that the powerline noise is still high; in some embodiments, this may result in this interval being flagged as having severe contact issues due to a change in relative R-wave peak energy from one interval to another that is greater than the threshold value discussed above with reference to step 1310 of exemplary method 1300. Referring to FIG. 18C, it may be seen that there is high powerline noise around sample number 14000. Referring to FIG. 18D, it may be seen that the powerline noise is still high; in some embodiments, this may result in this interval being flagged as having severe contact issues due to the signal RMS exceeding the threshold discussed above with reference to step 1310 of exemplary method 1300. Referring to FIG. 18E, it may be seen that there is high powerline noise throughout the signal. Referring to FIG. 18F, it may be seen that the powerline noise is still high; in some embodiments, this may result in this interval being flagged as having severe contact issues due to the SNR of this signal failing to meet the threshold SNR discussed above with reference to step 1310 of exemplary method 1300. Referring to FIGS. 18G and 18H, it may be seen a clear signal is visible; in some embodiments, this may result in this interval not being flagged as having contact issues.

Referring now to FIGS. 19A and 19B, extraction of R-wave peaks in accordance with step 1315 is shown. It will be apparent to those of skill in the art that FIGS. 19A and 19B represent R-wave peak extraction from a single channel and that, in a practical implementation of the method 1300 as described above, data sets comparable to those shown in FIGS. 19A and 19B will be present for each channel of data. FIG. 19A shows filtered data (e.g., as produced by step 1310) prior to the performance of step 1315. In FIG. 19A, detected peak positions are represented by asterisks. FIG. 19B shows data with extracted peaks following the performance of step 1315. In FIG. 19B, peak positions are represented by asterisks. It may be seen that, in FIG. 19A, some of the peak locations indicated by asterisks are not located at the maximal value of the peak in the data, and that such positions are correctly indicated by the asterisks in FIG. 19B.

Referring now to FIGS. 20A-20C, removal of EMG artifacts in accordance with step 1320 is shown. It will be apparent to those of skill in the art that FIGS. 20A-20C represent removal of EMG artifacts from a single channel and that, in a practical implementation of the method 1300 as described above, data sets comparable to those shown in FIGS. 20A-20C will be present for each channel of data. FIG. 20A shows exemplary filtered data used as in step 1320 (e.g., as produced by step 1310). FIG. 20B shows same filtered data of FIG. 20A and additionally includes a representation of the motion envelope and the inter-peaks absolute sum. In FIG. 20B, peaks suspected to be corrupted are indicated by diamonds. FIG. 20C shows a corrected signal after EMG artifact correction, as produced by step 1320. In FIG. 20C, the suspect peaks have been removed, with corrected peaks shown circled and the original peak values shown in a contrasting shade.

Referring now to FIGS. 21A and 21B, removal of baseline artifacts in accordance with step 1325 is shown. It will be apparent to those of skill in the art that FIGS. 21A and 21B represent removal of baseline artifacts from a single channel and that, in a practical implementation of the method 1300 as described above, data sets comparable to those shown in FIGS. 21A and 21B will be present for each channel of data. FIG. 21A shows exemplary data prior to baseline artifacts removal that may be received as input to step 1325. In FIG. 21A, a baseline artifact is indicated within a circle. In the data shown in FIG. 21A, the baseline ratio between the circled area and the rest of the signal is less than 0.8. In some embodiments, a corrected signal is provided by dividing the rest of the signal by this factor. FIG. 21B shows an exemplary corrected signal such as may be produced by step 1325. In FIG. 21A, the baseline artifact area is indicated within a circle. It may be seen by comparing FIGS. 21A and 21B that the baseline artifact has been removed.

Referring now to FIGS. 22A and 22B, trimming of outliers and gaps in accordance with step 1330 is shown. It will be apparent to those of skill in the art that FIGS. 22A and 22B represent trimming of outliers and gaps from a single channel and that, in a practical implementation of the method 1300 as described above, data sets comparable to those shown in FIGS. 22A and 22B will be present for each channel of data. FIG. 22A shows exemplary data that may be received as input to step 1330. It may be seen that the input data includes an outlier near sample 450, indicated in FIG. 22A with a diamond. FIG. 22B shows the exemplary data of FIG. 22A after the performance of step 1330 to remove outliers as described above. It may be seen that the outlier shown in FIG. 22A has been removed.

Referring now to FIGS. 23A and 23B, interpolation and extraction of an R-wave peak signal in accordance with step 1330 is shown. It will be apparent to those of skill in the art that FIGS. 23A and 23B represent extraction of an R-wave peak signal from a single channel and that, in a practical implementation of the method 1300 as described above, data sets comparable to those shown in FIGS. 23A and 23B will be present for each channel of data. FIG. 23A shows an exemplary R-wave peaks signal that may be provided as output from step 1330 and received as input to step 1335. FIG. 23B shows an exemplary clean interpolated R-wave signal that may be produced by the performance of step 1335.

Referring now to FIGS. 24A and 24B, channel selection in accordance with step 1335 is shown. In the exemplary data set shown in FIGS. 24A and 24B, channels 3 and 8 were found to be ineligible for channel selection due to the presence of contact issues in more than 10% of time intervals. Accordingly, in FIGS. 24A and 24B, only exemplary channels 1, 2, 4, 5, 6, and 7 are shown. Independent channel pairs of the data shown in FIG. 24A with corresponding Kendall correlation values are shown in the table below:

| 1$^{st}$ Channel | 2$^{nd}$ Channel | Kendall correlation value |
|---|---|---|
| 1 | 5 | 0.01 |
| 1 | 6 | 0.49 |
| 1 | 7 | 0.51 |
| 2 | 5 | 0.08 |
| 2 | 6 | 0.39 |
| 2 | 7 | 0.58 |
| 4 | 5 | −0.16 |
| 4 | 6 | 0.38 |
| 4 | 7 | 0.58 |

It may be seen from the above table that the group consisting of channels 1, 2, 4, and 7 demonstrates moderate correlation (e.g., correlation greater than 0.5 but less than 0.7). Accordingly, channels 1, 2, 4 and 7 are selected in step 1340. FIG. 24B shows an exemplary data set output by step 1340 including selected channels 1, 2, 4, and 7.

Referring now to FIGS. 25A and 25B, calculation of an EUM signal based on selected channels in accordance with step 1345 is shown. Channel data shown in FIG. 24B is received as input to step 1345 in order to produce output data shown in FIGS. 25A-25B. Referring to FIG. 25A, this figure shows an 80$^{th}$ percentile signal extracted from the signals shown in FIG. 24B. FIG. 25B shows a corrected signal obtained by applying wandering baseline removal to the signal shown in FIG. 25A.

Referring now to FIG. 26, calculation of a normalized EUM signal in accordance with step 1350 is shown. Corrected data as produced by step 1345 and as shown in FIG. 25B is received as input to step 1350 in order to produce a normalized EUM signal as shown in FIG. 26. FIG. 26 shows a normalized signal obtained by normalizing the signal shown in FIG. 25B and setting the baseline value to 30 visualization voltage units. It may be seen in FIG. 26 that three weak peaks are present in the signal.

Referring now to FIGS. 27A-27C, sharpening of an EUM signal in accordance with step 1355 is shown. An exemplary normalized signal as produced by step 1350, such as the exemplary normalized signal shown in FIG. 26 is received as input to step 1355 in order to produce a sharpened EUM signal. FIG. 27A shows an exemplary normalized EUM signal as produced by step 1350. FIG. 27B shows an exemplary enhancement mask generated in accordance with step 1355. FIG. 27C shows an exemplary sharpened EUM signal produced by adding the normalized EUM signal of FIG. 27A to the mask of FIG. 27B.

Referring now to FIG. 28, post-processing of an EUM signal in accordance with step 1360 is shown. The sharpened EUM signal as produced by step 1355 is received as input to step 1360 in order to produce a post-processed EUM signal. FIG. 28 shows an exemplary post-processed EUM signal after removing a wandering baseline as described above with reference to step 1360. It may be seen that the three weak peaks shown in FIG. 26 are more clearly visible in FIG. 28 following the sharpening of step 1355 and the post-processing of step 1360.

Referring now to FIG. 29, a tocograph signal corresponding to the exemplary EUM signal of FIG. 28 is shown. As previously noted, the exemplary EUM signal of FIG. 28 is produced in accordance with the method 1300. The representative tocograph signal of FIG. 29 was captured for the same subject during the same time interval as the data used to generate the exemplary EUM signal of FIG. 28. It may be seen that FIGS. 28 and 29 are substantial matches for one another and include the same three peaks as one another.

Figure 30:
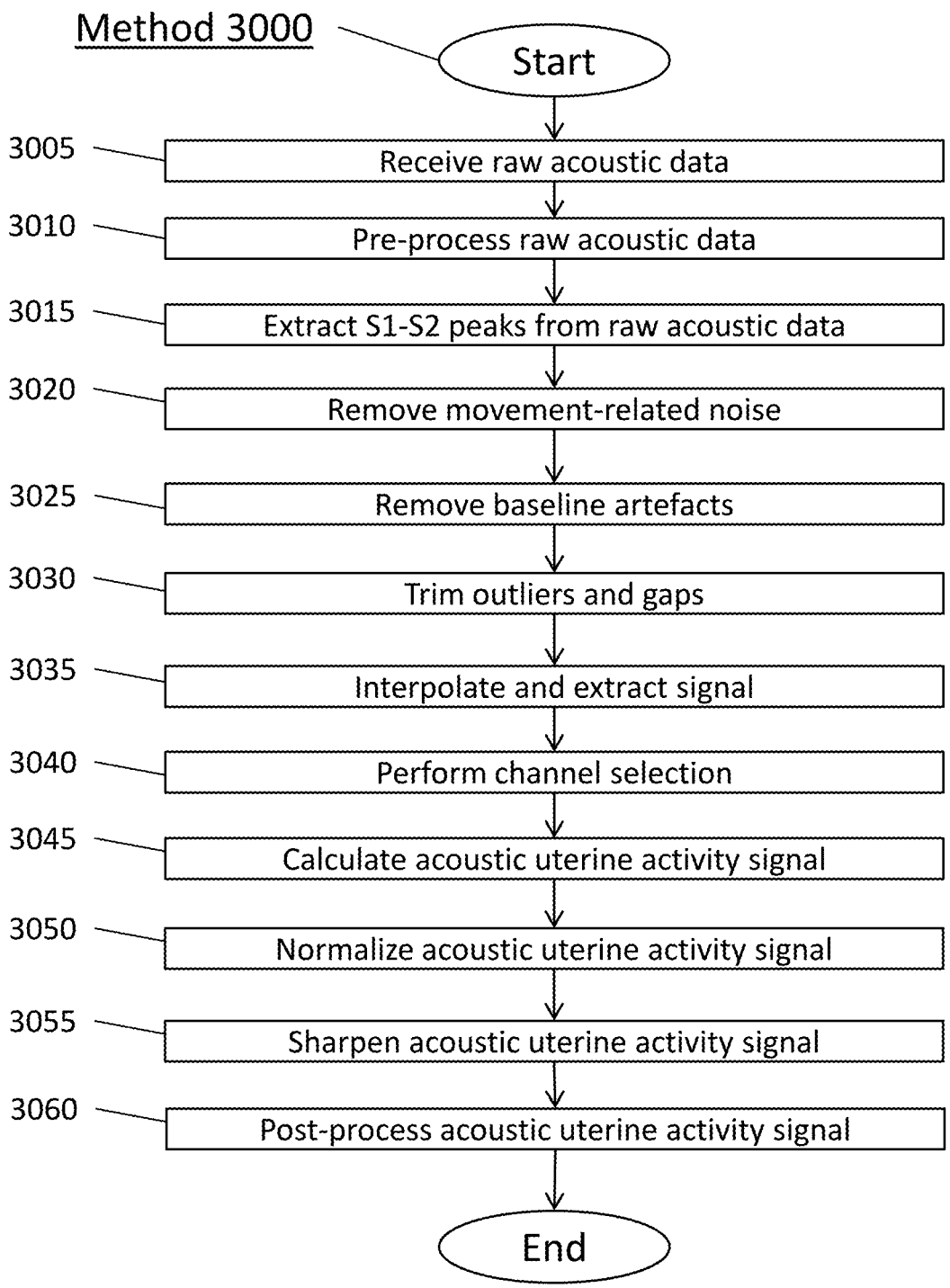
FIG. 30 shows a flowchart of a third exemplary method.

In some embodiments, uterine monitoring is performed based on acoustic data collected using one or more acoustic sensors such as the acoustic sensors 320 described above with reference to FIG. 3. In some embodiments, the process for uterine monitoring based on acoustic data is substantially similar to the process for uterine monitoring based on bio-potential data described above with reference to the method 1300 shown in FIG. 13, other than as will be described hereinafter. FIG. 30 shows an exemplary method 3000 for uterine monitoring based on acoustic data. In some embodiments, an exemplary inventive computing device is programmed/configured to execute the method 3000. In some embodiments, the exemplary inventive computing device is programmed/configured in accordance with the method 3000 via instructions stored in a non-transitory computer-readable medium. In some embodiments, the exemplary inventive computing device includes at least one computer processor, which, when executing the instructions, becomes a specifically-programmed computer processor programmed/configured in accordance with the method 3000. In some embodiments, the exemplary inventive computing device is specifically configured to solve the technical problems discussed below by the performance of the method 3000.

In step 3005, the exemplary inventive computing device is specifically configured to receive raw acoustic data as input. In some embodiments, one set of raw acoustic data (e.g., one raw acoustic input) is received from each of a plurality of acoustic sensors positioned in proximity to the abdomen of a pregnant human subject. In some embodiments, one set of raw acoustic data is received from each of two, or three, or four, or five, or six, or seven, or eight, or nine, or ten, or a greater number of acoustic sensors. In one specific exemplary embodiment that will be discussed in detail in the present description of the method 3000, one set of raw acoustic data is received from each of four acoustic sensors, as shown in FIG. 3.

Figure 31A:
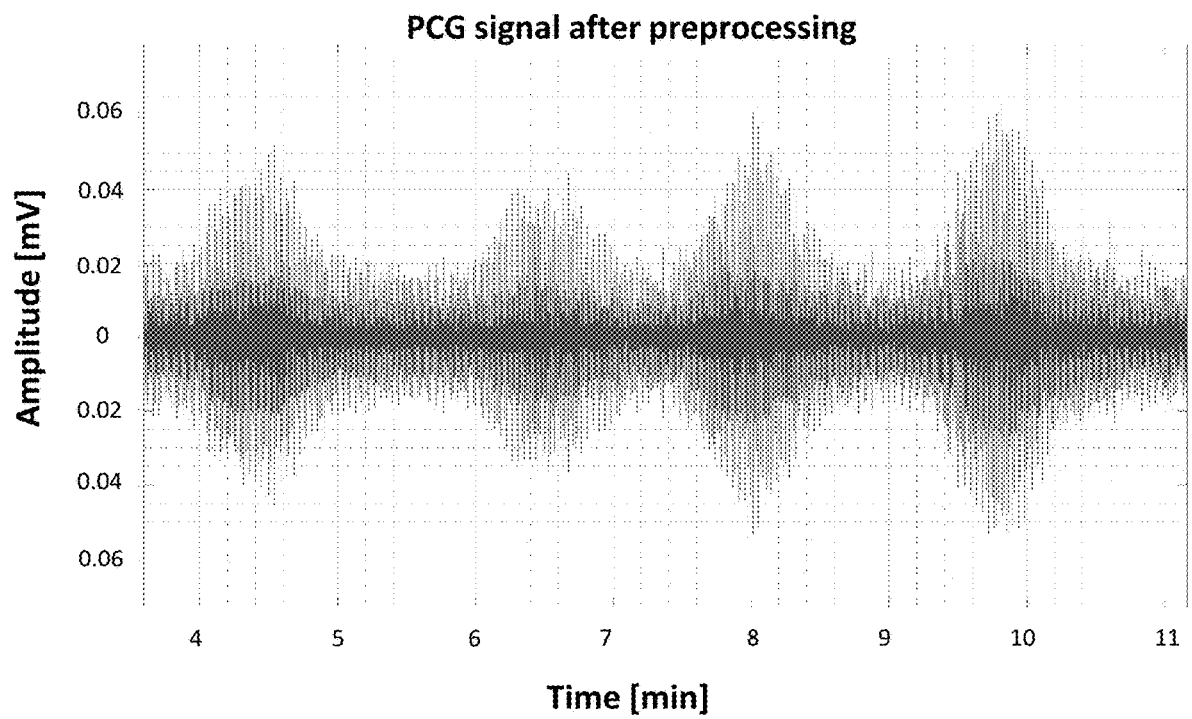
FIG. 31A shows an exemplary pre-processed data set.
Figure 31B:
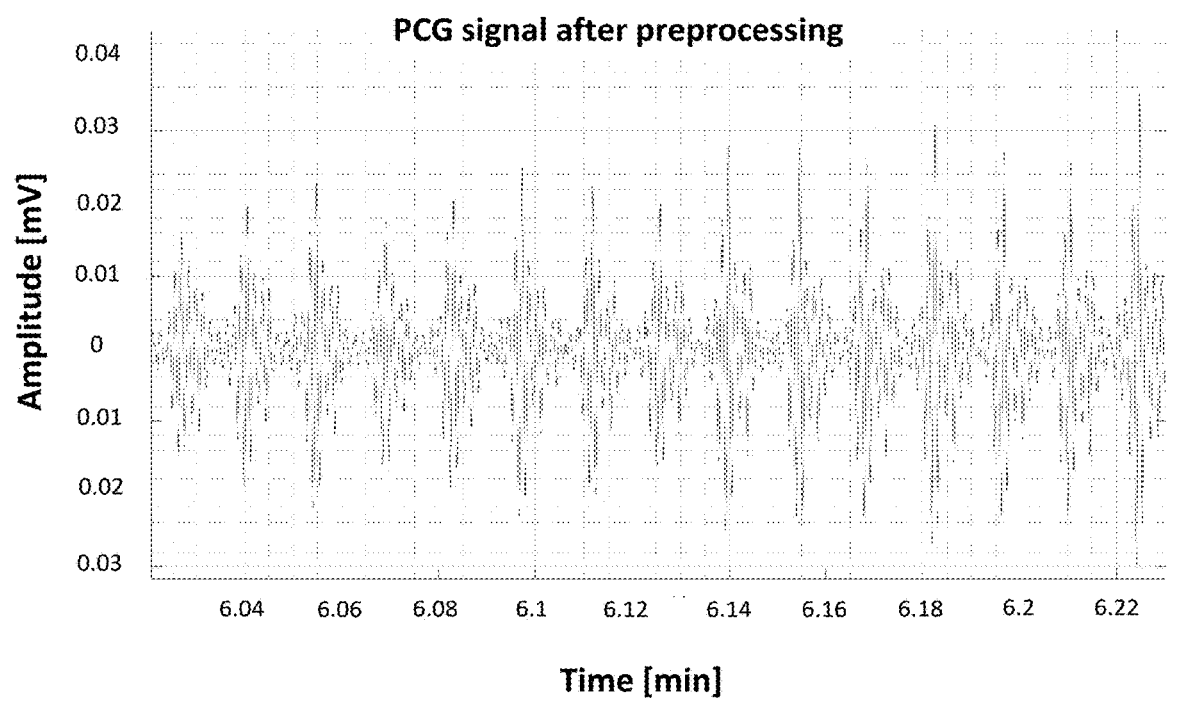
FIG. 31B shows a magnified view of a portion of the exemplary pre-processed data set of FIG. 31A.

In step 3010, the exemplary inventive computing device is specifically configured to pre-process the raw acoustic data to produce a plurality of channels of pre-processed acoustic data. In some embodiments, pre-processing includes applying at least one filter (e.g., one filter, or two filters, or three filters, or four filters, or five filters, or six filters, or seven filters, or eight filters, or nine filters, or ten filters, or a greater number of filters) to the raw acoustic data, e.g., applying each of a quantity X of filters to each of a quantity Y of channels of raw data to produce a quantity X times Y of preprocessed data channels. In some embodiments, the filters include bandpass filters. In some embodiments, the filters include DC filters. In some embodiments, the filters include finite impulse response filters, or infinite impulse response ("IIR") filters such as Butterworth filters or Chebyshev filters, or combinations thereof. In some embodiments, the filters include twelfth order Butterworth IIR filters, or third order Butterworth IIR filters, or fifth order Butterworth IIR filters. In one exemplary embodiment, the filters include five twelfth order Butterworth IIR filters having frequencies: 10-50 Hz, 15-50 Hz, 20-50 Hz, 25-50 Hz, and 30-50 Hz. In some embodiments, the application of five IIR filters to four raw data channels produces twenty (20) preprocessed data channels. FIG. 31A shows data in an exemplary preprocessed data channel following step 3010. FIG. 31B shows a magnified view of a small time window of the data shown in FIG. 31A.

Figure 32A:
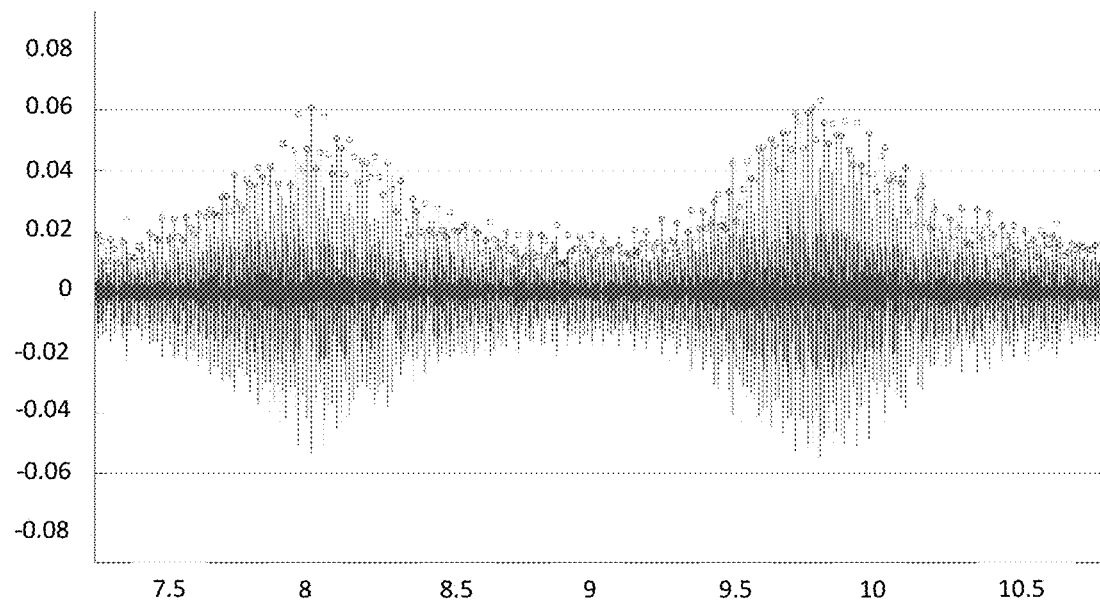
FIG. 32A shows extracted R-wave peaks in an exemplary pre-processed data set.
Figure 32B:
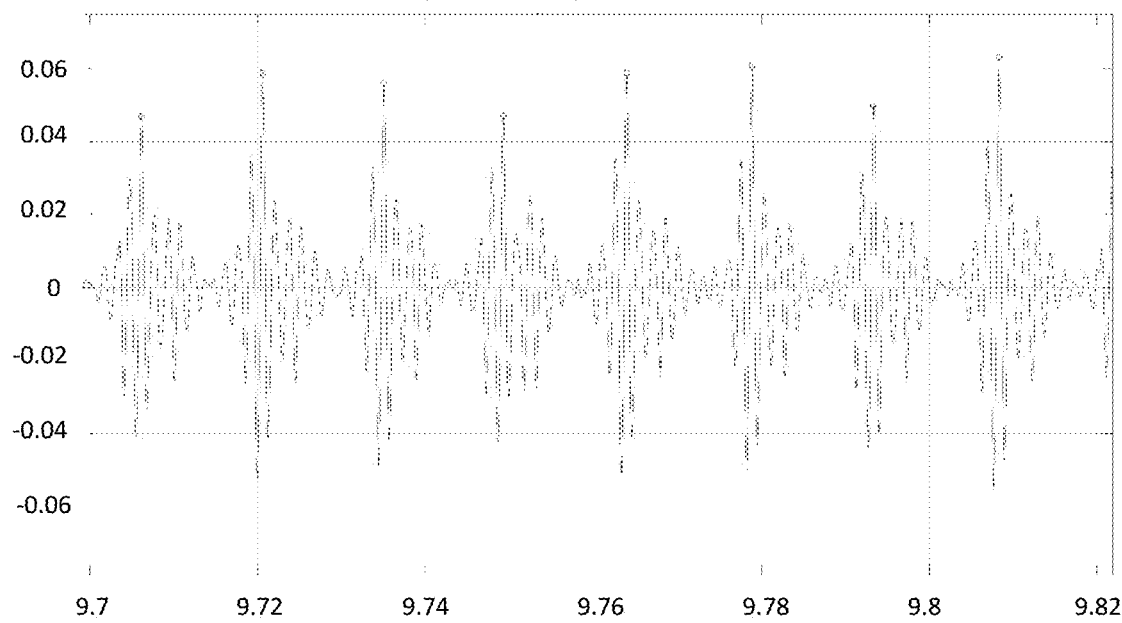
FIG. 32B shows a magnified view of extracted R-wave peaks in an exemplary pre-processed data set.
Figure 32C:
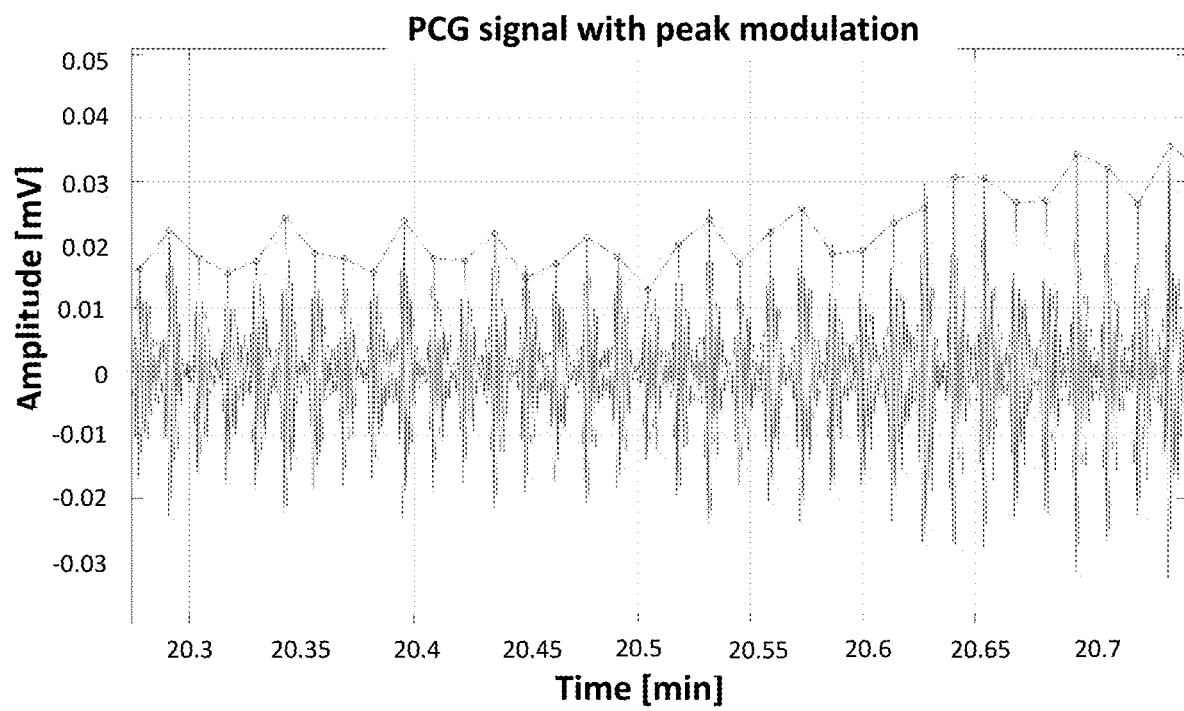
FIG. 32C shows an exemplary R-wave amplitude signal.
Figure 32D:
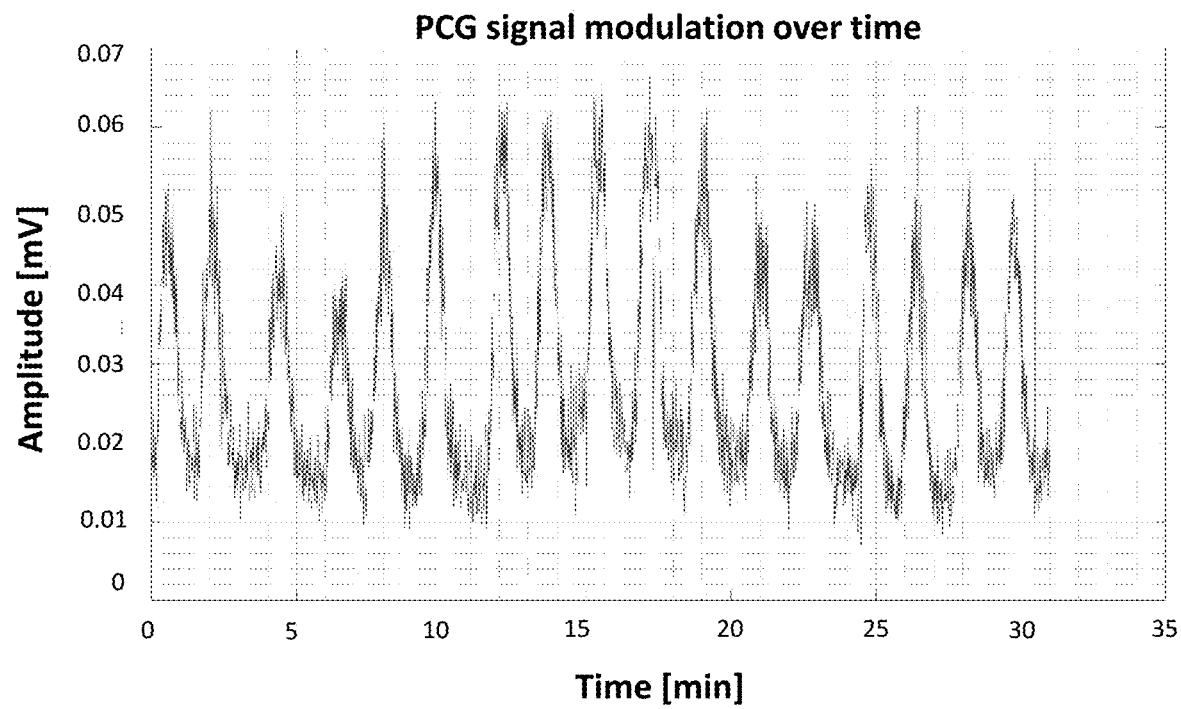
FIG. 32D shows an exemplary R-wave amplitude signal over a larger time window.

In step 3015, the exemplary inventive computing device is specifically configured to extract the peaks of the S1-S2 complexes from the pre-processed data channels. It will be known to those of skill in the art that S1 and S2 refer to the first and second sounds within the cardiac cycle. In some embodiments, the term "S1-S2 peak" refers to the maximal point within a given S1-S2 complex. In some embodiments, the S1-S2 peak extraction of step 3015 is performed in a manner substantially similar to the R-wave peak extraction of step 1315 of the method 1300 as described above. FIG. 32A shows data in an exemplary data channel with annotated S1-S2 peaks shown therein. FIG. 32B shows a magnified view of a small time window of the data shown in FIG. 32A. FIG. 32C shows an exemplary S1-S2 amplitude signal determined based on the S1-S2 peaks such as those shown in FIG. 32A. FIG. 32D shows an exemplary S1-S2 amplitude signal over a larger time window.

Figure 33:
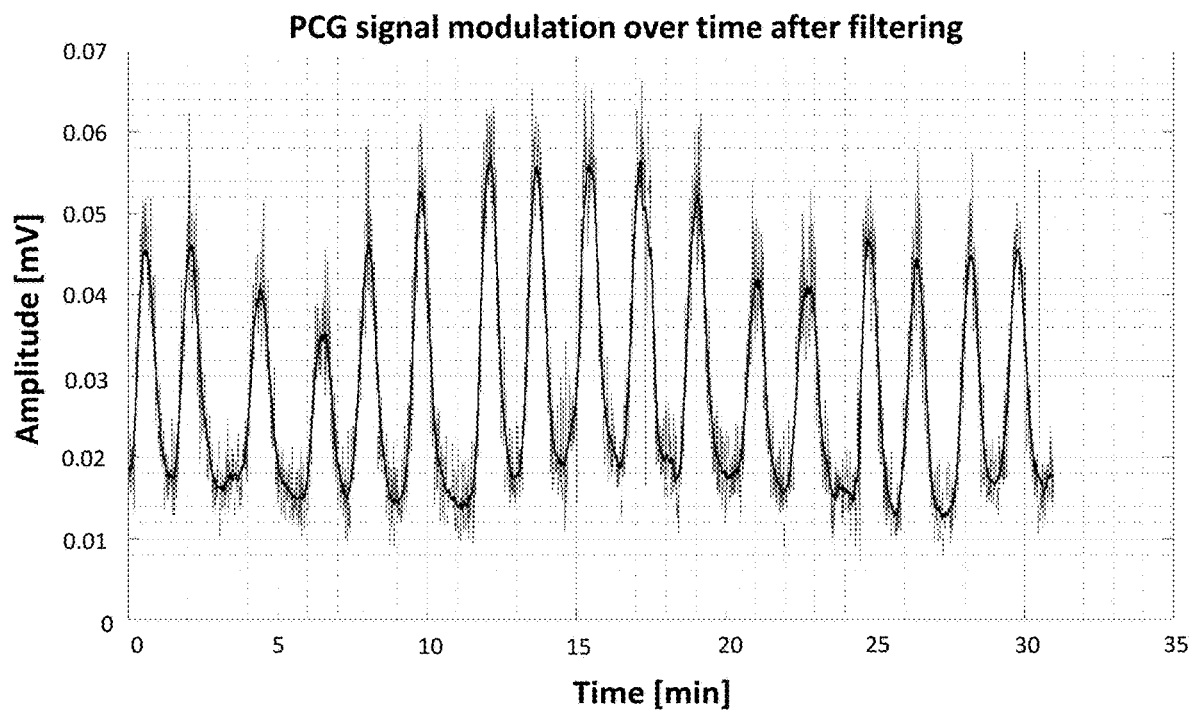
FIG. 33 shows an exemplary R-wave amplitude signal after filtering.

In steps 3020, 3025, and 3030, the exemplary inventive computing device is specifically configured to remove artifacts and outliers from the data sets produced in step 3015 in the same manner as described above with reference to steps 1320, 1325, and 1330 of the method 1300. It should be noted that the acoustic data that is analyzed by the exemplary method 3000 does not include electrical noise of the type discussed above with reference to step 1320, but, rather, may typically include movement-related noise that is recorded by the acoustic sensors. However, the process for removing such movement-related noise is substantially similar to the process for removing electrical noise described above. FIG. 33 shows an exemplary data set of an exemplary data channel following the performance of steps 3020, 3025, and 3030.

Figure 34:
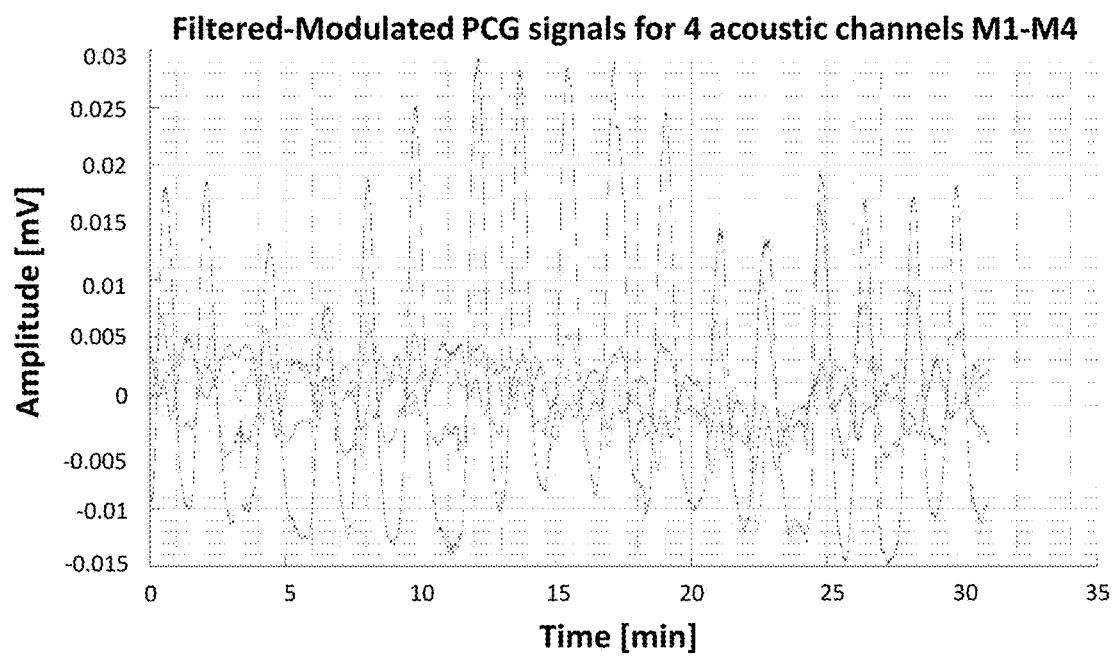
FIG. 34 shows four data channels of exemplary R-wave data.
Figure 35A:
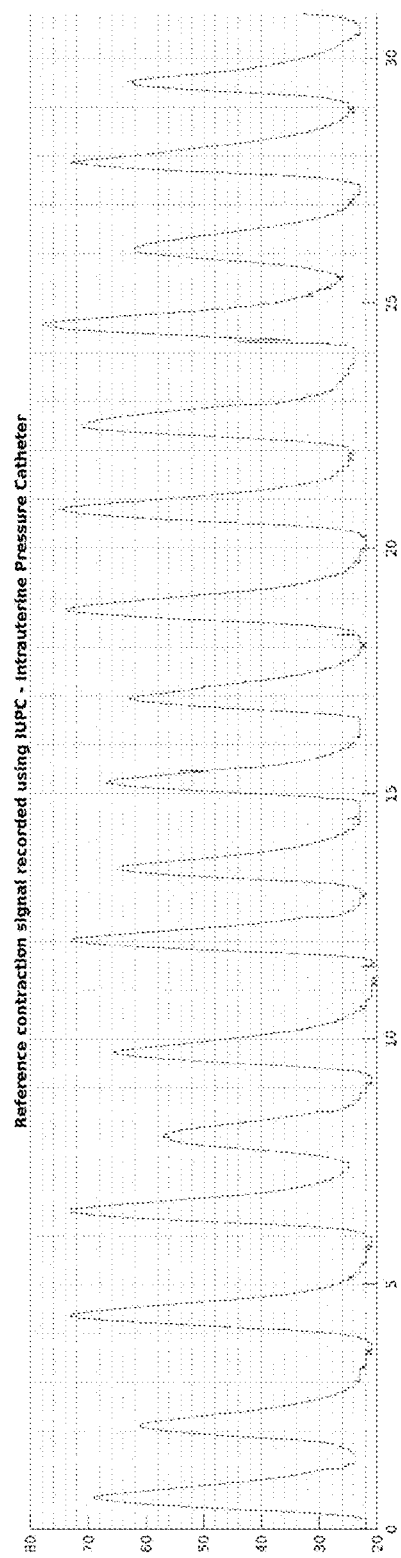
FIG. 35A shows a sixth tocograph signal.
Figure 35B:
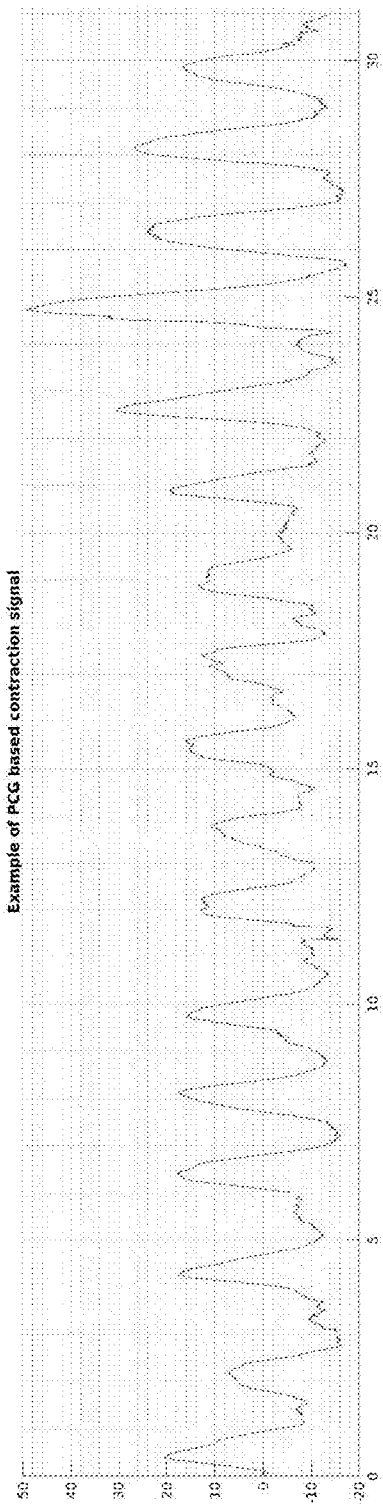
FIG. 35B shows a first exemplary acoustic uterine signal derived from acoustic data recorded during the same time period as that shown in FIG. 35A
Figure 36A:
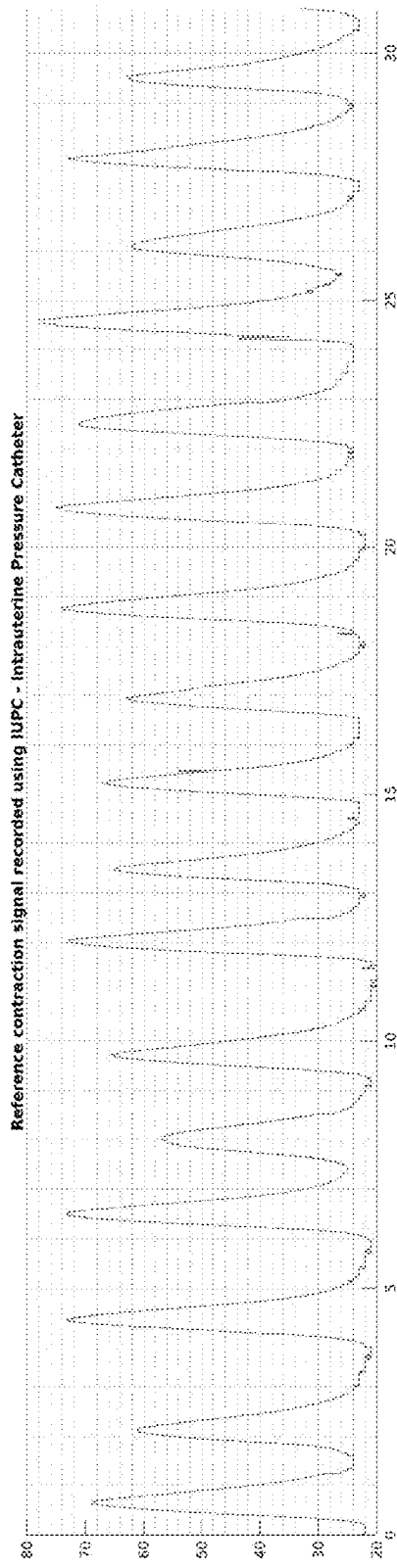
FIG. 36A shows a seventh tocograph signal.
Figure 36B:
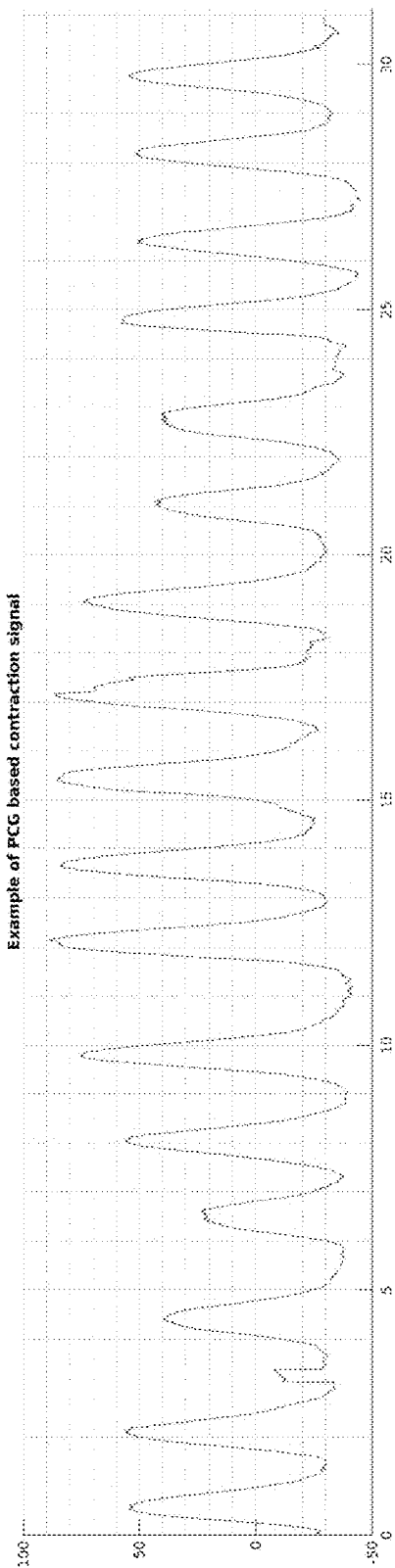
FIG. 36B shows a second exemplary acoustic uterine signal derived from acoustic data recorded during the same time period as that shown in FIG. 36A
Figure 37A:
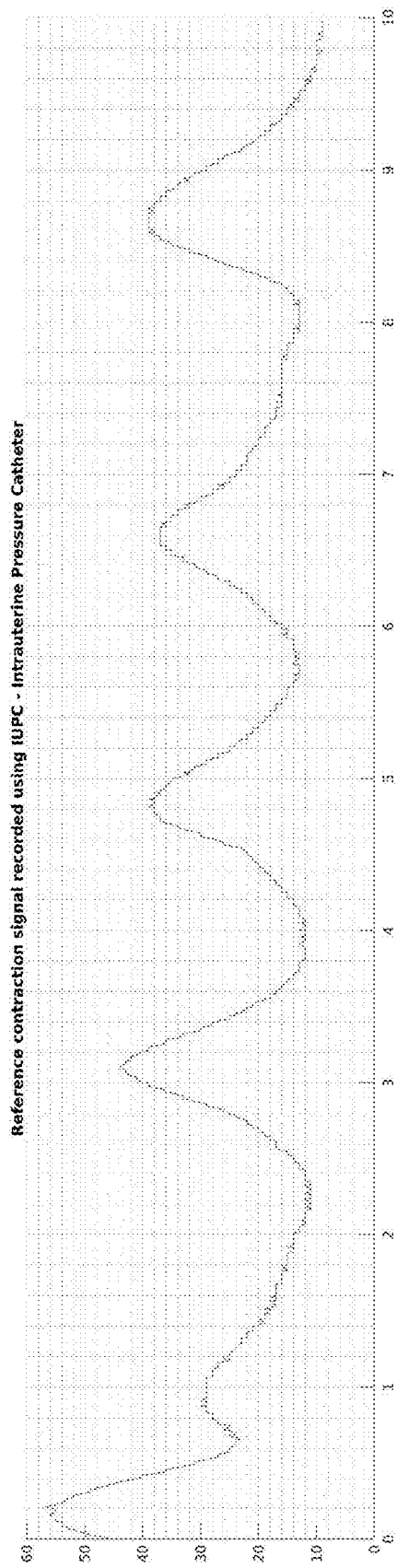
FIG. 37A shows an eighth tocograph signal.
Figure 37B:
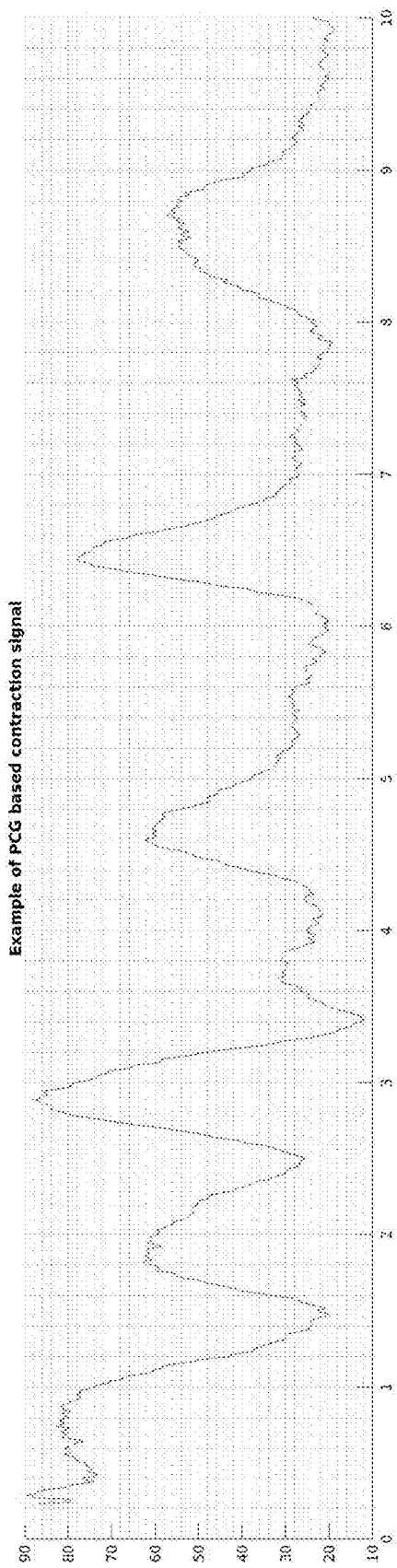
FIG. 37B shows a third exemplary acoustic uterine signal derived from acoustic data recorded during the same time period as that shown in FIG. 37A

In step 3035, the exemplary inventive computing device is specifically configured to interpolate and extract S1-S2 signal data from the data sets produced in step 3030 in a manner substantially similar to that described above with reference to step 1335 of the method 1300. FIG. 34 shows extracted S1-S2 data sets for a plurality of channels as calculated in step 3035.

In step 3040, the exemplary inventive computing device is specifically configured to perform channel selection in a manner substantially similar to that described above with reference to step 1340 of the method 1300. However, the channel selection of step 3040 differs from that of step 1340 in one aspect. As discussed above, some of the data channels used in step 1340 are not independent from one another due to the differential nature of the bio-potential sensors, as a result of which only some of the data channels used in step 1340 can be coupled with one another. In contrast, the acoustic sensors that collect the data used in the method 3000 are single-ended, i.e., independent from one another. Consequently, any two channels of data may be properly coupled with one another in step 3040. Thus, for example, in an embodiment in which four raw data channels are processed using five different bandpass filters to produce twenty filtered data channels, there are twenty times nineteen, i.e., 380 possible channel couples.

Following channel selection of step 3040, in step 3045, the exemplary inventive computing device is specifically configured to calculate an acoustic uterine activity signal in a manner substantially similar to that described with reference to step 1345 of the method 1300. In step 3050, the exemplary inventive computing device is specifically configured to normalize the acoustic uterine activity signal in a manner substantially similar to that described above with reference to step 1350 of the method 1300. In step 3055, the exemplary inventive computing device is specifically configured to sharpen the normalized acoustic uterine activity signal in a manner substantially similar to that described above with reference to step 1355 of the method 1300. In step 3060, the exemplary inventive computing device is specifically configured to post-process the sharpened acoustic uterine activity signal in a manner substantially similar to that described above with reference to step 1360 of the method 1300.

In some embodiments, the output of the exemplary method 3000 is an acoustic uterine monitoring signal that is determined non-invasively through the analysis of data that can be obtained by acoustic sensors positioned around the abdomen of a pregnant human subject. In some embodiments, the acoustic uterine monitoring signal generated by the exemplary method 3000 provides uterine monitoring data similar to that generated by a tocodynamometer and an ultrasound transducer, and can be used for monitoring uterine activity such as contractions.

FIGS. 35A-37B show examples of comparisons between tocograph data and the output of the exemplary method 3000. In each of FIGS. 35A, 36A, and 37A, a tocograph signal against time is shown. In each of FIGS. 35B, 36B, and 37B, the output of the performance exemplary method 3000 using acoustic data recorded during the same time intervals is shown. It can be seen that the peaks in the exemplary acoustic-based uterine monitoring signal correspond to the peaks in the tocograph data.

As discussed herein, a technical problem in the field of maternal/fetal care is that existing solutions for monitoring uterine activity (e.g., contractions) through the use of a tocodynamometer and an ultrasound transducer require an expectant mother to wear uncomfortable sensors, and can produce unreliable data when worn by obese expectant mothers (e.g., the sensors may not have sufficient sensitivity to produce usable data). As further discussed herein, the exemplary embodiments present technical solutions to this technical problem through the use of various sensors (e.g., bio-potential sensors and/or acoustic sensors) integrated into a comfortably wearable device and the analysis of data that can be obtained by such sensors (e.g., electrodes and/or acoustic sensors) to produce a signal that can be utilized to monitor uterine activity. A further technical problem in the field of maternal/fetal care is that existing solutions for analysis based on signals that can be obtained by sensors (e.g., bio-potential sensors and/or acoustic sensors) that can be integrated into a comfortably wearable device are limited to analyzing such signals to extract cardiac data. As discussed herein, the exemplary embodiments present a technical solution to this technical problem through the analysis of bio-potential data and/or acoustic data to produce a signal that can monitor uterine activity (e.g., contractions).

Publications cited throughout this document are hereby incorporated by reference in their entirety. Although the various aspects of the invention have been illustrated above by reference to examples and embodiments, it will be appreciated that the scope of the invention is defined not by the foregoing description but by the following claims properly construed under principles of patent law. Further, many modifications may become apparent to those of ordinary skill in the art, including that various embodiments of the inventive methodologies, the inventive systems, and the inventive devices described herein can be utilized in any combination with each other. Further still, the various steps may be carried out in any desired order (and any desired steps may be added and/or any undesired steps in a particular embodiment may be eliminated).

What is claimed is:

1. A computer-implemented method, comprising:
   receiving, by at least one computer processor, a plurality of raw acoustic inputs at a sampling rate that is between 100 samples per second and 10,000 samples per second,
      wherein each of the raw acoustic inputs being received from a corresponding one of a plurality of acoustic sensors, and
      wherein each of the plurality of acoustic sensors is positioned so as to measure a respective one of the raw acoustic inputs of a pregnant human subject;
   generating, by the at least one computer processor, a plurality of signal channels from the plurality of raw acoustic inputs,
      wherein the plurality of signal channels comprises at least three signal channels;
   pre-processing, by the at least one computer processor, respective signal channel data of each of the signal channels to produce a plurality of pre-processed signal channels,
      wherein each of the pre-processed signal channels comprises respective pre-processed signal channel data;
   extracting, by the at least one computer processor, a respective plurality of S1-S2 peaks from the pre-processed signal channel data of each of the pre-processed signal channels to produce a plurality of S1-S2 peak data sets,
      wherein each of the S1-S2 peak data sets comprises a respective plurality of S1-S2 peaks;
   removing, by the at least one computer processor, from the plurality of S1-S2 peak data sets, at least one of: (a) at least one signal artifact or (b) at least one outlier data point,
      wherein the at least one signal artifact is one of a movement-related artifact or a baseline artifact;
   replacing, by the at least one computer processor, the at least one signal artifact, the at least one outlier data point, or both, with at least one statistical value determined based on a corresponding one of the S1-S2 peak data sets from which the at least one signal artifact, the at least one outlier data point, or both was removed, to produce a plurality of updated S1-$\Omega$ peak data sets;
   executing, by the at least one computer processor, at least one interpolation algorithm on each of the plurality of updated S1-S2 peak data sets so as to generate a respective S1-S2 signal data set for a respective S1-S2 signal channel at a predetermined sampling rate so as to produce a plurality of S1-S2 signal channels;
   selecting, by the at least one computer processor, at least one first selected S1-S2 signal channel and at least one second selected S1-S2 signal channel from the plurality of S1-S2 signal channels based on at least one correlation between (a) a respective S1-S2 signal data set of at least one first particular S1-S2 signal channel and (b) a respective S1-S2 signal data set of at least one second particular S1-S2 signal channel; and
   generating, by the at least one computer processor, acoustic uterine contraction monitoring data representative of an acoustic uterine contraction monitoring signal utilizing at least the respective S1-S2 signal data set of the first selected S1-S2 signal channel and the respective S1-S2 signal data set of the second selected S1-S2 signal channel.

2. The computer-implemented method of claim 1, further comprising:
   sharpening, by the at least one computer processor, the acoustic uterine contraction monitoring data to produce a sharpened acoustic uterine contraction monitoring signal.

3. The computer-implemented method of claim 2, further comprising:
   determining, by the at least one computer processor, whether the acoustic uterine contraction monitoring data is calculated based on a selected one of the acoustic uterine contraction monitoring signal channels that is a corrupted acoustic uterine contraction monitoring signal channel,
   wherein the step of sharpening, by the at least one computer processor, the acoustic uterine contraction monitoring data is omitted if the acoustic uterine contraction monitoring data is calculated based on the selected one of the acoustic uterine contraction monitoring signal channels that is the corrupted acoustic uterine signal monitoring channel.

4. The computer-implemented method of claim 2, further comprising:
   post-processing the sharpened acoustic monitoring signal data to produce a post-processed acoustic uterine contraction monitoring signal.

5. The computer-implemented method of claim 2, wherein the step of sharpening, by the at least one computer processor, the acoustic uterine contraction monitoring data comprises:

identifying a set of peaks in the acoustic uterine contraction monitoring signal data;
determining a prominence of each of the peaks;
removing, from the set of peaks, peaks having a prominence that is less than at least one threshold prominence value;
calculating a mask based on remaining peaks of the set of peaks;
smoothing the mask based on a moving average window to produce a smoothed mask; and
adding the smoothed mask to the acoustic uterine contraction monitoring signal data to produce the sharpened acoustic uterine contraction monitoring signal data.

6. The computer-implemented method of claim 5, wherein the at least one threshold prominence value includes at least one threshold prominence value selected from a group consisting of an absolute prominence value and a relative prominence value calculated based on a maximal prominence of the peaks in the set of peaks.

7. The computer-implemented method of claim 5, wherein the mask includes zero values outside areas of the remaining peaks and nonzero values inside areas of the remaining peaks,
wherein the nonzero values are calculated based on a Gaussian function.

8. The computer-implemented method of claim 1, wherein the at least one filtering step of the pre-processing step includes applying at least one filter selected from a group consisting of a DC removal filter, a powerline filter, and a high pass filter.

9. The computer-implemented method of claim 1, wherein the step of extracting, by the at least one computer processor, the respective plurality of S1-S2 peaks comprises:
receiving a set of maternal ECG peaks for the pregnant human subject; and
identifying S1-S2 peaks in each of the pre-processed signal channels within a predetermined time window before and after each of the maternal ECG peaks in the set of maternal ECG peaks as a maximum absolute value in each of the pre-processed signal channels within the predetermined time window.

10. The computer-implemented method of claim 1, wherein the step of removing at least one of a signal artifact or an outlier data point comprises removing at least one movement artifact by a process comprising:
identifying at least one corrupted peak in one of the plurality of S1-S2 peak data sets based on the at least one corrupted peak having an inter-peaks root mean square value that is greater than a threshold; and
replacing the corrupted peak with a median value, wherein the median value is either a local median or a global median.

11. The computer-implemented method of claim 1, wherein the step of removing at least one of a signal artifact or an outlier data point comprises removing at least one baseline artifact by a process comprising:
identifying a change point in S1-S2 peaks in one of the plurality of S1-S2 peak data sets;
subdividing the one of the plurality of S1-S2 peak data sets into a first portion located prior to the change point and a second portion located subsequent to the change point;
determining a first root-mean-square value for the first portion;
determining a second root-mean-square value for the second portion;
determining an equalization factor based on the first root-mean-square value and the second root-mean-square value; and
modifying the first portion by multiplying S1-S2 peaks in the first portion by the equalization factor.

12. The computer-implemented method of claim 1, wherein the step of removing at least one of a signal artifact or an outlier point comprises removing at least one outlier in accordance with a Grubbs test for outliers.

13. The computer-implemented method of claim 1, wherein the step of generating a respective S1-S2 data set based on each respective S1-S2 peak data set comprises interpolating between the S1-S2 peaks of each respective S1-S2 peak data set, and wherein the interpolating between the S1-S2 peaks comprises interpolating using an interpolation algorithm that is selected from a group consisting of a cubic spline interpolation algorithm and a shape-preserving piecewise cubic interpolation algorithm.

14. The computer-implemented method of claim 1, wherein the step of selecting at least one first one of the S1-S2 signal channels and at least one second one of the S1-S2 signal channels from the plurality of S1-S2 signal channels comprises:
identifying contact issues in each of the plurality of S1-Ω signal channels;
determining a percentage of prior intervals in which each of the plurality of S1-S2 signal channels experienced contact issues;
selecting candidate S1-S2 signal channels from the plurality of S1-S2 signal channels based on the percentage of prior intervals in which each of the plurality of S1-S2 signal channels experienced contact issues;
grouping the selected candidate S1-S2 signal channels into a plurality of couples, wherein each of the couples includes two of the selected candidate S1-S2 channels that are independent from one another;
calculating a correlation value of each of the couples;
identifying at least one of the couples having a correlation value that exceeds a threshold correlation value;
selecting, as the selected at least one first one of the S1-S2 signal channels, the first candidate S1-S2 signal channel of each of the identified at least one of the couples; and
selecting, as the selected at least one second one of the S1-S2 signal channels, the second candidate S1-S2 signal channel of each of the identified at least one of the couples.

15. The computer-implemented method of claim 1, wherein the step of calculating the acoustic uterine contraction monitoring signal comprises calculating the acoustic uterine contraction monitoring signal that is, at each point in time, a predetermined percentile of all of the selected at least one first one of the S1-S2 signal channels and the selected at least one second one of the S1-S2 signal channels at that point in time.

16. The computer-implemented method of claim 15, wherein the predetermined percentile is an $80^{th}$ percentile.

17. The computer-implemented method of claim 1, wherein the statistical value is one of a local median, a global median, or a mean.

* * * * *

UNITED STATES PATENT AND TRADEMARK OFFICE
CERTIFICATE OF CORRECTION

PATENT NO. : 11,284,833 B2
APPLICATION NO. : 17/168771
DATED : March 29, 2022
INVENTOR(S) : Muhammad Mhajna Page 1 of 1

It is certified that error appears in the above-identified patent and that said Letters Patent is hereby corrected as shown below:

In the Claims

Column 36, Line 15, Claim 1 delete "S1-$\Omega$" and insert -- S1-S2 --
Column 38, Line 27, Claim 14 delete "S1-$\Omega$" and insert -- S1-S2 --

Signed and Sealed this
Twenty-seventh Day of September, 2022

Katherine Kelly Vidal
*Director of the United States Patent and Trademark Office*